(12) United States Patent
Rosazza et al.

(10) Patent No.: US 7,425,433 B2
(45) Date of Patent: Sep. 16, 2008

(54) CARBOXYLIC ACID REDUCTASE POLYPEPTIDE, NUCLEOTIDE SEQUENCE ENCODING SAME AND METHODS OF USE

(75) Inventors: John P. Rosazza, Iowa City, IA (US); Ian Fotherington, Edinburgh (GB); Tao Li, Union, NJ (US); Lacy Daniels, Iowa City, IA (US); Aimin He, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 11/431,321

(22) Filed: May 10, 2006

(65) Prior Publication Data

US 2006/0199254 A1    Sep. 7, 2006

Related U.S. Application Data

(63) Continuation of application No. 10/386,329, filed on Mar. 11, 2003, now Pat. No. 7,056,714.

(51) Int. Cl.
*C12N 9/02* (2006.01)
*C12N 15/00* (2006.01)
*C12P 21/04* (2006.01)
*C12P 7/00* (2006.01)
*C12Q 1/26* (2006.01)
*C07H 21/04* (2006.01)

(52) U.S. Cl. .................. 435/189; 435/440; 435/25; 435/69.1; 435/71.1; 435/132; 536/23.2

(58) Field of Classification Search .............. None
See application file for complete search history.

(56) References Cited

U.S. PATENT DOCUMENTS 5,795,759 A    8/1998   Rosazza et al.
6,261,814 B1   7/2001   Rosazza et al.
7,056,714 B2 * 6/2006   Rosazza et al. ............ 435/189

OTHER PUBLICATIONS

Cole et al. Deciphering the biology of Mycobacterium tuberculosis from the complete genome sequence.☐☐Nature. Jun. 11, 1998;393(6685):537-44. Erratum in: Nature Nov. 12, 1998;396(6707):190.*
Guo et al. Proc Natl Acad Sci USA. Jun. 22, 2004;101(25):9205-10.*
Branden et al. Introduction to Protein Structure, Garland Publishing Inc., New York, p. 247, 1991.*
Kita et al. "Cloning of the aldehyde reductase gene from a red yeast, *Sporobolomyces salmonicolor*, and characterization of the gene and its product." Appl. Environ. Microbiol. Jul. 1996;62(7):2303-10.
Venkitasubramanian et al., "Reduction of Carboxylic Acids by Nocardia Aldehyde Oxidoreductase Requires a Phosphopantetheinylated Enzyme", J. of Biol. Chem., 282(1)P478-485 (2007).

* cited by examiner

*Primary Examiner*—Yong D Pak
(74) *Attorney, Agent, or Firm*—McKee, Voorhees & Sease, P.L.C.

(57) ABSTRACT

The invention provides the nucleotide sequence and amino acid sequence for the enzyme carboxylic acid reductase isolated from bacteria. Expression cassettes, vectors, transformed cells, and variants are also provided as methods for use of recombinant biocatalytic reagents in production of synthetic, aromatic, aliphatic and alicyclic aldehydes and alcohols.

3 Claims, 8 Drawing Sheets

```
Nocardia    1   --AVDSPDERLQRRIAQLFAETEQVKAARPLEAVSAAVSAPGMRLAQIAATVMAGYADRP
MtfadD      1   ---MSINDQRLTRRVEDLYASLAQFAAASENEAITQAIDQPGVALPQLIRMVMEGYADRP
MBCG        1   ---MSINDQRLTRRVEDLYASLAQFAAASENEAITQAIDQPGVALPQLIRMVMEGYADRP
MlAcS       1   MSTTTKQEKQLARRVDDLTANLPQFAAAKPDPAVAAALAQPGLRLPQIIQTALDGYAERP
Msmeg       1   -MTIETREDRFNRRIDHLFETLPQFAAAREDEAISAAAADPELRLPAAVKQLLAGYADRP
consensus   1        v    d rl RRie Lfa D QfaAA P eAvs Av  Pgm Lpqii  vm GYAdRP Nocardia    59  AAGQRAFELNTLDATGRTSLRLLPRFETITYRELWQRVGEVAAAWHHDPENPLRAGLFVA
MtfadD      58  ALGQRALREVTLDPDSGRTMVELLPRFETITYRELWARAGTLATALSAEP--AIRPGDRVC
MBCG        58  ALGQRALREVTLDPDSGRTMVELLPRFETITYRELWARAGTLATALSAEP--AIRPGDRVC
MlAcS       61  ALGQRVAEFTKLPKTGRTSMELLPSFETITYROLGDRVGALARAWRHD---LLHAGYRVC
Msmeg       60  ALGKRAVEFVTL-EEGRTTAKLLPRFDTITYROLAGRIQAVTNAWHNH---PVNAGDRVA
consensus   61  AlGqRa   f  tD tGRT l LLPrFeTITYR L  R g va A     d  lr GdrV Nocardia    119 ILGFTSIDYATLDLADIHLGAVTVPLQASAAVSQLIATLTETSPRLLASTPEHLDAAVEC
MtfadD      116 VLGFNSVLDYTTIDLALIRLGAVSVPLQTSAPVTGLRPIVTETEPTMIATSIDNLGDAVEV
MBCG        116 VLGFNSVLDYTTIDLALIRLGAVSVPLQTSAPVTGLRPIVTETEPTMIATSIDNLGDAVEV
MlAcS       118 VLGFNSVDYAIIDMALGVITGAVAVPLQTSAAITQLQSIVTETEPSMIATSVNQLPDTVEL
Msmeg       116 ILGFTSVLYTTIDLALLPLGAVSVPLQTSAPVAQLQPIVAETEPKVIASSVDFLADAVAL
consensus   121 lLGF SvDY tiDlAli lGAVtVPLQtsA vs L  IvtETeP liAssie L daVev Nocardia    179 ILAGTTEERLVVFDYHPEDLDQAAFFSAPRRPLADAGSSVIVETLDAVRAPGRDLPAAPL
MtfadD      176 IAG-HAPARLVVFDYHGKVDTHREAVEAARARLAG---SVTIDTIAELIERGRALPAT--
MBCG        176 IAG-HAPARLVVFDYHGKVDTHREAVEAARARLAG---SVTIDTIAELIERGRALPAT--
MlAcS       178 ILSGQAPAKLVVFDTHPEVMEQHDAVATARARLADS--SVVVESLTEVLGRGKTLPATPI
Msmeg       176 VESGPAESRLVVFDLYSHEVDDQREAFEAAKGKLAGT--GVVVETITDALDRGRSLADAP-
consensus   181 l     aP rLVVFDYh  vD  reA e ArarLA   sV vetl evi RGr Lpa Nocardia    239 FVPLTDDPLALLIYTSGSTGTPKGAMYTNRLAATMWQG---NSMLQGNSQRVGLNLLYM
MtfadD      230 PIALSADLALALLIYTSGSTGAPKGAMYRESQVMSFWRK---SSGWFEPSGYPSITLHFM
MBCG        230 PIALSADLALALLIYTSGSTGAPKGAMYRESQVMSFWRK---SSGWFEPSGYPSITLHFM
MlAcS       236 PVALDSADPLALLIYTSGSTGAPKGAMILQSNVGKMWRR---SDGNWFGPTAASITLNFM
Msmeg       233 LYVPDEALPPLTLLIYTSGSTGTPKGAMYPESKTAIMWQAGSKARWDETLGVMPSITLHFM
consensus   241  v d   D LaLLIYTSGSTG PKGAMY   s   t W          sItLNfM Nocardia    296 PMSHIAGRISLEGVLARGGTAYFAAKSDMSTLFEDIGLVRPTEIFFVPRVCDMVFQRYQS
MtfadD      287 PMSHVGGPQVLYGTLSNGGTAYFVAKSDLSTLFEDLALVRPTELCFVPRIVDMVFAEFHS
MBCG        287 PMSHVGGPQVLYGTLSNGGTAYYVAKSDLSTLFEDLALVRPTELCFVPRIWDMVFAEFHS
MlAcS       293 PMSHVMGPGILYGTLGNGGTAYFAARSDLSTLLEDLKLVRPTELNFVPRIWETLYDESKR
Msmeg       293 PMSHVMGRGILCSTLASGGTAYFAARSDLSTFLEDLAVVRPTQLNFVPRIWDMLEQEYQS
consensus   301 PMSHv GR vLfgtL  GGTAYf AksDlSTl EDlgLVRPTel FVPRiwdmvf ey s Nocardia    356 ELDRRSVAG---ALLDTLDREVKADLRQNYLGGRFLVAVVGSAPLAAEMKTFMES-VLDLP
MtfadD      347 EVDRRLVDG---ADRAALEAQVKAELPENVLGGRFVMALTGSAPISAEMTAWVESLLADVH
MBCG        347 EVDRRLVDG---ADRAALEAQVKAELPENVLGGRFVMALTGSAPISAEMTAWVESLLADVH
MlAcS       353 AVDRPLANSGSALRAAIKAEVMDEQRQSLLGGRYIAAMTGSAPTSPELKHGVES-LLEMH
Msmeg       353 RLDNRRAEG---S-EDRAEAAVLEEVRTQLLGGRFVSALTGSAPISAEMKSWVED-LLDMH
consensus   361 lDrR   g    ad   lda V  elR nvLGGRfl AvtGSAPlsaEm  fvEs l dlh Nocardia    413 LHDGYGSTEAGASVLLDNQIQRPPVLDYKLVDVPELGYFRTLRPHPRGELLLKAETTIPG
MtfadD      405 LVEGYGSTEAG-MVLNDGMVRRPAVIDYKLVDVPELGYFGTDQPYPRGELLVKTQTMFPG
MBCG        405 IVEGYGSTEAG-MVLNDGMVRRPAVIDYKLVDVPELGYFGTDQPYPRGELLVKTQTMFPG
MlAcS       412 LLEGYGSTEAG-MVLFDGEVQRPPVIDYKLVDVPDLGYFSTDQPYPRGELLLKTQNMFPG
Msmeg       409 LLEGYGSTEAG-AVFIDGQIQRPPVIDYKLVDVPDLGYFATDRPYPRGELLVKSEQMFPG
consensus   421 LveGYGSTEAG  Vl Dg i RP ViDYKLVDVPeLGYF TD PyPRGELLlKt  mfPG
```

FIG.1A

```
Nocardia  473 YYKRPEVTAEIFDEDGFYKTGDIVAELEHDRLVYVDRRHIIVLKLSQGEFVTVAHLEAVFA
MtfadD    464 YTQRPDVTAEVFDPDGFYRTGDIMAKVGPDQFVYLDRRHIIVLKLSQGEFIAVSKLEAVFG
MBCG      464 YTQRPDVTAEVFDPDGFYRTGDIMAKVGPDQFVYLDRRHIIVLKLSQGEFIAVSKLEAVFG
MlAcS     471 YYKRPEVTATVFDSDGYIQTGDIVAEVGPIRLVIVDRRHNVLKLAQGQFVTVAKLEAAFS
Msmeg     468 YYKREEITAEMFDEDGYYRTGDIVAELGPDHLEYLDRRNHVLKLSQGEFVTVSKLEAVFG
consensus 481 YY RPevTAeiFD DGfYkTGDIvA lgpD  vYvDRRNNVLKLsQGeFv V kLEAvFa Nocardia  533 SSPLIRQIFIYGSSERSYLLAVIVPTDDALRGRDTATLKSALAESIQRIAKDANLQPYEI
MtfadD    524 DSPLVRQIFIYGNSARAYPLAVVVPSGDALSRHGIENLKPVISESLQEVARAAGLQSYEI
MBCG      524 DSPLVRQIFIYGNSARAYPLAVVVPSGDALSRHGIENLKPVISESLQEVARAAGLQSYEI
MlAcS     531 NSPLVRQIYIYGNSAHPYLLAVVVPTEDALATNDIEVLKPLIIDSLQKVAKEADLQSYEV
Msmeg     528 DSPLVRQIYVYGNSAPSYLLAVVVPTEEALSRWDGDELKSRISDSLQDAARAAGLQSYEI
consensus 541  SPLvRQIfiYGnSar Y LAVvVPt dAL   e LK  i eSlQ iAk A LQsYEi Nocardia  593 PRDFLIETEPFTIANGLLSGIAKLLRENLKERYGAQLEQMYTDLATGQADELLALRREAA
MtfadD    584 PRDFIIETTPFTLENGLLTGIRKLARPQLKKFYGERLERLYTELADSQSNELRELRQSGP
MBCG      584 PRDFIIETTPFTLENGLLTGIRKLARPQLKKFYGERLERLYTELADSQSNELRELRQSGP
MlAcS     591 PRDLIVETTPFSLENGLLTGIRKLAWPKLKQHYGARLEQLIADLVEGQANLHVLKQSVA
Msmeg     588 PRDFLVETTPFTLENGLLTGIRKLAPPKLKAHYGERLEQLYTDLAEGQANELRELPRNGA
consensus 601 PRDfliETtPFtleNGLLtGIrKLarP LK  YG rLE lYtdLad Q  neLr Lr  a Nocardia  653 DLPVLETVSRAAKAMLGVASADMRPDAHFTDLGGDSLSALSFSLLHEIFGVEVPVGVV
MtfadD    644 DAPVIPTLCRAAAALLGSTAADVRPDAHFADLGGDSLSALSLANLLHEIFGVDVPVGVIV
MBCG      644 DAPVIPTLCRAAAALLGSTAADVRPDAHFADLGGDSLSALSLANLLHEIFGVDVPVGVIV
MlAcS     651 NAPVLQTVSRAVGTILGVATTDLPSNAHFTDLGGDSLSALTFGSLLRELFDIDVPVGVIV
Msmeg     648 DRPVVETVSRAAVALLGASVTDLRSDAHFTDLGGDSLSALSFSLLHEIFDVDVPVGVIV
consensus 661 d PVl Tv RAa amLG   Dmr dAHF DLGGDSLSALs  nLLhEiF vdVPVGViV Nocardia  713 SPANELRDLANYIEAERNSGAKRPTFTSVHG-GGSEIRAADLTLDKFIDARTIAAADSIP
MtfadD    704 SPASDIRALADHIEAAR-TGVRRPSFASIHGRSATEVHASDLTLDKFIDAATIAAAPNLP
MBCG      704 SPASDIRALADHIEAAR-TGVRRPSFASIHGRSATEVHASDLTLDKFIDAATIAAAPNLP
MlAcS     711 SPVNNIVAIADYIFRER-QGTKRPTFIAIHGRDAGKVHASDLTLDKFIDVSTLTAAPVLA
Msmeg     708 SPATDLAGVAAYIEGEL-RGSKRPTYASVHGRDATEVRARDLALGKFIDAKTLSAAPGLP
consensus 721 SPa eL alA  IEa r  G kRPtf svHGr asevrA DLtLdKFIDa TL AAp lp Nocardia  772 HAPVPAQTVLLTGANGYLGRFLCLEWLERLDKTGGTLICVVRGSDAAARKRLDSAFDSG
MtfadD    763 APSAQVRTVLLTGATGFLGRYLALEWLDRMDLVNGKLICLVRARSDEEAQARLDATFDSG
MBCG      763 APSAQVRTVLLTGATGFLGRYLALEWLDRMDLVNGKLICLVRARSDEEAQARLDATFDSG
MlAcS     770 QPGTERTVLLTGATGFLGRYLALKWLERMDLVEGKMIALVRAKSNEDARARLDKTFDSG
Msmeg     767 RSGTERTVLLTGATGFLGRYLALEWLERMDLVDGKVICLVRARSDDEARARLDATFDTG
consensus 781   vrTVLLTGAtGfLGRyLaLeWLeRmDlv GklIclVRars eeA aRLD tFDsG Nocardia  832 DPGIEHYQQLAARTLEVIAGDIGDPNLGLDDATWQRLAETVDLIVHPAALVHVLPYTQ
MtfadD    823 DPYLVRHYRELGAGRLEVLAGDKGEADLGLDRVTWQRLADTVDLIVDPAALVHVLPYSQ
MBCG      823 DPYLVRHYRELGAGRLEVLAGDKGEADLGLDRVTWQRLADTVDLIVDPAALVHVLPYSQ
MlAcS     830 DPKLLAHYQELATDHLEVIAGDKGEVDLELDRQTWRRLADTVDLIVDPAALVHVLPYSE
Msmeg     827 DATLLEHYRALADHLEVIAGDKGEADLGLDHDTWQRLADTVDLIVDPAALVHVLPYSQ
consensus 841 Dp Ll HY  Laa rLEVlAGDkGe dLgLDr TWqRLAdTVDLIVdPAALVNHVLPYsq Nocardia  892 LFGPNVVGTAEIVRLAITARRKPVTYLSTVGVADQVDPAEYQEDSDVPEMSAVPVVRESY
MtfadD    883 LFGHAAGTAELLRLALTGKRKPYIYTSTIAVGEQIPPEAFTELADIRALSPTRRIDDSY
MBCG      883 LFGHAAGTAELLRLALTGKRKPYIYTSTIAVGEQIPPEAFTELADIRALSPTRRIDDSY
MlAcS     890 LFGNTLGTAELIRIALTSKQKPYIYVSTIGVGNQIEPAKFTELSDIPVESPTRNINNNY
Msmeg     887 MFGHIALGTAELIRIALTTIKPYMIVSTIGVGQGISPEAVELADIRELSAFRRVDDSY
consensus 901 lFGPN  GTAElvRlAlT r KPyiY STigVg qi P  f ED DiR iS tR v esY
```

FIG.1B

```
Nocardia    952  ANGYGNSKWAGEVLLREAHDLCGLPVAVFRSDMILAHSRYAGQLNVQLVFTRLILSIVAT
MtfadD      943  AHGYANSKWAGEVLLREAHEQCGLPVTVFRCDMILADTSYTGQLNLPDMFTRLMLSLAAT
MBCG        943  AHGYANSKWAGEVLLREAHEQCGLPVTVFRCDMILADTSYTGQLNLPDMFTRLMLSLAAT
MlAcS       950  ANGYGNSKWAGEVLLREAHDLCGLPVTVFRCDMILADTSYAGQLNVPDMFTPMMLSLAAT
Msmeg       947  ANGYGNSKWAGEVLLREAHDWCGLPVSVFRCDMILADTTYSGQLNLPDMFTRLMLSLVAT
consensus   961  ANGYgNSKWAGEVLLREAHd CGLPVtVFRcDMILAdtsY GQLNvpDmFTRlmLSL AT Nocardia    1012 GIAPYSFYRTDADGNRQRAHYDGLPADFTAAAITALG---IQATEGERTYDVLNPYDDGI
MtfadD      1003 GIAPGSFYELDAHGNRQRAHYDGLPVEFVAEAICTLG---THSPLREVTYHVMNPYDDGI
MBCG        1003 GIAPGSFYELDAHGNRQPAHYDGLPVEFVAEAICTLG---THSPLREV------------
MlAcS       1010 GIAPGSFYELDAESNRQRAHYDGLPVEFIAEAISTLGDQSLHDRDGFTTYHVMNPHDDGI
Msmeg       1007 GIAPGSFYELDADGNRQRAHTDGLPVEFIAEAISTIG---SQVTLGEETEHVMNPYDDGI
consensus   1021 GIAPgSFYelDA gNRQRAHYDGLPveFvAeAI tlG        d F ty vlnp ddgi Nocardia    1069 SLDEFVDWLVESG----HPIQRITDYSDWFHRFETAIRALPEKQRQASVLPLLDAMRNEC
MtfadD      1060 GLDEFVDWLNSPTSGSGCTIQRIALYGEWLQRFETSLRALPDRQHASLLPLLHNYREPA
MBCG             ------------------------------------------------------------
MlAcS       1070 GMDEFVDWLID----AGCPIQRINDYDEWLRRFEISLRALPERQHSSLLPLLHNYQKPE
Msmeg       1064 GLDEYVDWLIEAG----YPVHPVDDYATWLSRFETALRALPERQQASLLPLLHNYQQPS
consensus   1081      ldefvdwl        i ri dy  w  rfe  iralpekqr svlpll   y  p Nocardia    1125 PAVRGAILEAKEFQAAVQTAKIGPEQDIPHLSAPLIDKYVSDLELLQLL (SEQ ID NO:81)
MtfadD      1120 KPICGSIAPTDQFRAAVQEAKIGPDKDIPHLTAAIIAKYISNLRLLGLL (SEQ ID NO:32)
MBCG             ------------------------------------------------ (SEQ ID NO:33)
MlAcS       1126 KPLHGSLAPTIRFRTAVQNANIGQDKDIPHISPATIAKYVSDLQLLGLV (SEQ ID NO:34)
Msmeg       1120 PPVCGAMAPTDRFRAAVQDAKIGPDKDIPHVTADVIVKYISNLQMLGLL (SEQ ID NO:35)
consensus   1141    v  gip   f   avq a ig e diphls  li kyvs l ll ll (SEQ ID NO:36)
```

FIG.1C

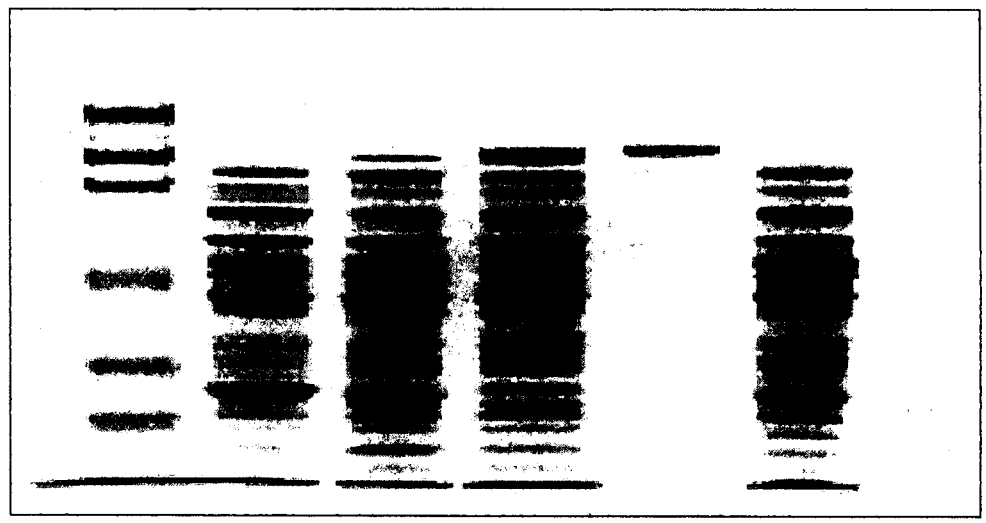
FIG.2

| | | |
|---|---|---|
| Car-C | LIYTSGSTGTPKGAMY | (SEQ ID NO:40) |
| FadD9 | LIYTSGSTGAPKGAMY | (SEQ ID NO:41) |
| yeast AAR | LSFTSGSEGIPKGVLG | (SEQ ID NO:42) |
| motif-Pc | ---TSGSEGRPKG--- | (SEQ ID NO:43) |
| consensus | l yTSGS G PKG m | (SEQ ID NO:44) |
| | | |
| Car-D | DLPLHDGYGSTEAG | (SEQ ID NO:45) |
| FadD9 | DVHLVEGYGSTEAG | (SEQ ID NO:46) |
| yeast | NCRIVNMYGTTETQ | (SEQ ID NO:47) |
| motif-Pc | ---IVNMYGTT--- | (SEQ ID NO:48) |
| consensus | lv YGsTe | (SEQ ID NO:49) |
| | | |
| Car-F | DEDGFYKTGDIVAE | (SEQ ID NO:50) |
| FadD9 | DPDGFYRTGDIMAK | (SEQ ID NO:51) |
| yeast | PRDRLYRTGDLGRY | (SEQ ID NO:52) |
| motif-Pc | ---RLYRSGDL--- | (SEQ ID NO:53) |
| consensus | d YrtGDl | (SEQ ID NO:54) |
| | | |
| Car-H | DANLQPYEIPRDF- | (SEQ ID NO:55) |
| FadD9 | AAGLQSYEIPRDF- | (SEQ ID NO:56) |
| yeast | EPTLITFMVPR-FD | (SEQ ID NO:57) |
| motif-Pc | ---LVSYFVP---- | (SEQ ID NO:58) |
| consensus | L sy iPr f | (SEQ ID NO:59) |
| | | |
| Car-I | NGLLSGIAKLLRPNLKER | (SEQ ID NO:60) |
| FadD9 | NGLLTGIRKLARPQLKKF | (SEQ ID NO:61) |
| yeast | KLPLNPNGKVDKPKLQFP | (SEQ ID NO:62) |
| motif-Pc | ---LNPNGKIDKPAL--- | (SEQ ID NO:63) |
| consensus | L gKv kP L | (SEQ ID NO:64) |
| | | |
| Car-J | FTDLGGDSLSALSF | (SEQ ID NO:65) |
| FadD9 | FADLGGDSLSALSL | (SEQ ID NO:66) |
| yeast | FFDLGGHSILATKM | (SEQ ID NO:67) |
| motif-Pc | ---LGGHSILAQ-- | (SEQ ID NO:68) |
| consensus | f dLGG Si A | (SEQ ID NO:69) |
| | | |
| Car-NADP | LLTGANGYLGRFL | (SEQ ID NO:70) |
| FadD9 | LLTGATGFLGRYL | (SEQ ID NO:71) |
| yeast | FVTGVTGFLGSYI | (SEQ ID NO:72) |
| motif-Pc | ---GATGFLGAHI | (SEQ ID NO:73) |
| consensus | vtGatGfLG yi | (SEQ ID NO:74) |
| | | |
| Car-Reduct | YANGYGNSKWAGE | (SEQ ID NO:75) |
| FadD9 | YANGYANSKWAGE | (SEQ ID NO:76) |
| yeast | LTGGYGQSKWAAE | (SEQ ID NO:77) |
| motif-Pc | ---GYGQSKW--- | (SEQ ID NO:78) |
| consensus | GYgqSKWaae | (SEQ ID NO:79) |

*FIG.3*

```
AVDSPDERLQ  RRIAQLFAED  EQVKAARPLE  AVSAAVSAPG  MRLAQIAATV
MAGYADRPAA  GQRAFELNTD  DATGRTSLRL  LPRFETITYR  ELWQRVGEVA           100
AAWHHDPENP  LRAGDFVALL  GFTSIDYATL  DLADIHLGAV  TVPLQASAAV
SQLIAILTET  SPRLLASTPE  HLDAAVECLL  AGTTPERLVV  FDYHPEDDDQ           200
RAAFESARRR  LADAGSLVIV  ETLDAVRARG  RDLPAAPLFV  PDTDDDPLAL
LIYTSGSTGT  PKGAMYTNRL  AATMWQGNSM  LQGNSQRVGI  NLNYMPMSHI   C       300
AGRISLFGVL  ARGGTAYFAA  KSDMSTLFED  IGLVRPTEIF  FVPRVCDMVF
QRYQSELDRR  SVAGADLDTL  DREVKADLRQ  NYLGGRFLVA  VVGSAPLAAE           400
MKTFMESVLD  LPLHDGYGST  EAGASVLLDN  QIQRPPVLDY  KLVDVPELGY   D
FRTDRPHPRG  ELLLKAETTI  PGYYKRPEVT  AEIFDEDGFY  KTGDIVAELE   F       500
HDRLVYVDRR  NNVLKLSQGE  FVTVAHLEAV  FASSPLIRQI  FIYGSSERSY
LLAVIVPTDD  ALRGRDTATL  KSALAESIQR  IAKDANLQPY  EIPRDFLIET   H       600
EPFTIANGLL  SGIAKLLRPN  LKERYGAQLE  QMYTDLATGQ  ADELLALRRE   I
AADLPVLETV  SRAAKAMLGV  ASADMRPDAH  FTDLGGDSLS  ALSFSNLLHE   J       700
IFGVEVPVGV  VVSPANELRD  LANYIEAERN  SGAKRPTFTS  VHGGGSEIRA
ADLTLDKFID  ARTLAAADSI  PHAPVPAQTV  LLTGANGYLG  RFLCLEWLER  NADP bind. 800
LDKTGGTLIC  VVRGSDAAAA  RKRLDSAFDS  GDPGLLEHYQ  QLAARTLEVL
AGDIGDPNLG  LDDATWQRLA  ETVDLIVHPA  ALVNHVLPYT  QLFGPNVVGT           900
AEIVRLAITA  RRKPVTYLST  VGVADQVDPA  EYQEDSDVRE  MSAVRVVRES
YANGYGNSKW  AGEVLLREAH  DLCGLPVAVF  RSDMILAHSR  YAGQLNVQDV   Reduction 1000
FTRLILSLVA  TGIAPYSFYR  TDADGNRQRA  HYDGLPADFT  AAAITALGIQ
ATEGFRTYDV  LNPYDDGISL  DEFVDWLVES  GHPIQRITDY  SDWFHRFETA          1100
IRALPEKQRQ  ASVLPLLDAY  RNPCPAVRGA  ILPAKEFQAA  VQTAKIGPEQ          1150
DIPHLSAPLI  DKYVSDLELL  QLL  (SEQ ID NO:81)
```

FIG.4

| | | | | | |
|---|---|---|---|---|---|
| SINDQRLTRR | VEDLYASDAQ | FAAASPNEAI | TQAIDQPGVA | LPQLIRMVME | |
| GYADRPALGQ | RALRFVTDPD | SGRTMVELLP | RFETITYREL | WARAGTLATA | 100 |
| LSAEPAIRPG | DRVCVLGFNS | VDYTTIDIAL | IRLGAVSVPL | QTSAPVTGLR | |
| PIVTETEPTM | IATSIDNLGD | AVEVLAGHAP | ARLVVFDYHG | KVDTHREAVE | 200 |
| AARARLAGSV | TIDTLAELIE | RGRALPATPI | ADSADDALAL | LIYTSGSTGA | C |
| PKGAMYRESQ | VMSFWRKSSG | WFEPSGYPSI | TLNFMPMSHV | GGRQVLYGTL | 300 |
| SNGGTAYFVA | KSDLSTLFED | LALVRPTELC | FVPRIWDMVF | AEFHSEVDRR | |
| LVDGADRAAL | EAQVKAELRE | NVLGGRFVMA | LTGSAPISAE | MTAWVESLLA | 400 |
| DVHLVEGYGS | TEAGMVLNDG | MVRRPAVIDY | KLVDVPELGY | FGTDQPYPRG | D |
| ELLVKTQTMF | PGYYQRPDVT | AEVFDPDGFY | RTGDIMAKVG | PDQFVYLDRR | F  500 |
| NNVLKLSQGE | FIAVSKLEAV | FGDSPLVRQI | FIYGNSARAY | PLAVVVPSGD | H |
| ALSRHGIENL | KPVISESLQE | VARAAGLQSY | EIPRDFIIET | TPFTLENGLL | 600 |
| TGIRKLARPQ | LKKFYGERLE | RLYTELADSQ | SNELRELRQS | GPDAPVLPT | I |
| CRAAAALLGS | TAADVRPDAH | FADLGGDSLS | ALSLANLLHE | IFGVDVPVGV | J  700 |
| IVSPASDLRA | LADHIEAART | GVRRPSFASI | HGRSATEVHA | SDLTLDKFID | |
| AATLAAAPNL | PAPSAQVRTV | LLTGATGFLG | RYLALEWLDR | MDLVNGKLIC | NADP |
| LVRARSDEEA | QARLDATFDS | GDPYLVRHYR | ELGAGRLEVL | AGDKGEADLG | |
| LDRVTWQRLA | DTVDLIVDPA | ALVNHVLPYS | QLFGPNAAGT | AELLRLALTG | 900 |
| KRKPYIYTST | IAVGEQIPPE | AFTEDADIRA | ISPTRRIDDS | YANGYANSKW | Reduction |
| AGEVLLREAH | EQCGLPVTVF | RCDMILADTS | YTGQLNLPDM | FTRLMLSLAA | |
| TGIAPGSFYE | LDAHGNRQRA | HYDGLPVEFV | AEAICTLGTH | SPDRFVTYHV | |
| MNPYDDGIGL | DEFVDWLNSP | TSGSGCTIQR | IADYGEWLQR | FETSLRALPD | 1100 |
| RQRHASLLPL | LHNYREPAKP | ICGSIAPTDQ | FRAAVQEAKI | GPDKDIPHLT | 1150 |
| AAIIAKYISN | LRLLGLL (SEQ ID NO:82) | | | | |

FIG.5

```
TNEKVWIEKL DNPTLSVLPH DFLRPQQEPY TKQATYSLQL PQLDVPHDSF
SNKYAVALSV WAALIYRVTG DDDIVLYIAN NKILRFNIQP TWSFNELYST            100
INNELNKLNS IEANFSFDEL AEKIQSCQDL ERTPQLFRLA FLENQDFKLD
EFKHHLVDFA LNLDTSNNAH VLNLIYNSLL YSNERVTIVA DQFTQYLTAA            200
LSDPSNCITK ISLITASSKD SLPDPTKNLG WCDFVGCIHD IFQDNAEAFP
ERTCVVETPT LNSDKSRSFT YRDINRTSNI VAHYLIKTGI KRGDVVMIYS            300
SRGVDLMVCV MGVLKAGATF SVIDPAYPPA RQTIYLGVAK PRGLIVIRAA
GQLDQLVEDY INDELEIVSR INSIAIQENG TIEGGKLDNG EDVLAPYDHY            400
KDTRTGVVVG PDSNPTLSFT SGSEGIPKGV LGRHFSLAYY FNWMSKRFNL  C
TENDKFTMLS GIAHDPIQRD MFTPLFLGAQ LYVPTQDDIG TPGRLAEWMS            500
KYGCTVTHLT PAMGQLLTAQ ATTPFPKLHH AFFVGDILTK RDCLRLQTLA
ENCRIVNMYG TTETQRAVSY FEVKSKNDDP NFLKKLKDVM PAGKGMLNVQ  D         600
LLVVNRNDRT QICGIGEIGE IYVRAGGLAE GYRGLPELNK EKFVNNWFVE
KDHWNYLDKD NGEPWRQFWL GPRDRLYRTG DLGRYLPNGD CECCGRADDQ  F         700
VKIRGFRIEL GEIDTHISQH PLVRENITLV RKNADNEPTL ITFMVPRFDK  H
PDDLSKFQSD VPKEVETDPI VKGLIGYHLL SKDIRTFLKK RLASYAMPSL            800
IVVMDKLPLN PNGKVDKPKL QFPTPKQLNL VAENTVSETD DSQFTNVERE
VRDLWLSILP TKPASVSPDD SFFDLGGHSI LATKMIFTLK KKLQVDLPLG  J         900
TIFKYPTIKA FAAEIDRIKS SGGSSQGEVV ENVTANYAED AKKLVETLPS
SYPSREYFVE PNSAEGKTTI NVFVTGVTGF LGSYILADLL GRSPKNYSFK  NADP bind.  1000
VFAHVRAKDE EAAFARLQKA GITYGTWNEK FASNIKVVLG DLSKSQFGLS
DEKWMDLANT VDIIIHNGAL VHWVYPYAKL RDPNVISTIN VMSLAAVGKP            1100
KFFDFVSSTS TLDTEYYFNL SDKLVSEGKP GILESDDLMN SASGLTGGYG
QSKWAAEYII RRAGERGLRG CIVRPGYVTG ASANGSSNTD DFLLRFLKGS  Reduction  1200
VQLGKIPDIE NSVNMVPVDH VARVVVATSL NPPKENELAV AQVTGHPRIL
FKDYLYTLHD YGYDVEIESY SKWKKSLEAS VIDRNEENAL YPLLHMVLDN            1300
LPESTKAPEL DDRNAVASLK KDTAWTGVDW SNGIGVTPEE VGIYIAFLNK            1350
VGFLPPPTHN DKLPLPSIEL TQAQISLVAS GAGARGSSAA A (SEQ ID NO:80)
```

FIG.6

SEQUENCE LISTING

```
<160> NUMBER OF SEQ ID NOS: 80

<210> SEQ ID NO 1
<211> LENGTH: 4600
<212> TYPE: DNA
<213> ORGANISM: Nocardia
<220> FEATURE:
<221> NAME/KEY: CDS
<222> LOCATION: (189)..(4598)

<400> SEQUENCE: 1
ggtaccggca atacctggat aagcggtcgg atcctgggcc gctgcggtgg agtggccgcc      60
gttccggccc gatgtgccca agaccactcg agtcaccgcc gcgtatcacc ttcccggaag     120
tatttactta ggctaacgtg ttttacgggt tgcagggctt ttcctactta tgacaaggga     180 ggcttgcc atg gca gtg gat tca ccg gat gag cgg cta cag cgc cgc att      230
         Met Ala Val Asp Ser Pro Asp Glu Arg Leu Gln Arg Arg Ile
```

-continued

|  | 1 |  |  |  | 5 |  |  |  |  | 10 |  |  |  |  |
|---|---|---|---|---|---|---|---|---|---|---|---|---|---|---|
| gca | cag | ttg | ttt | gca | gaa | gat | gag | cag | gtc | aag | gcc | gca | cgt | ccg | ctc | 278 |
| Ala | Gln | Leu | Phe | Ala | Glu | Asp | Glu | Gln | Val | Lys | Ala | Ala | Arg | Pro | Leu |
| 15 |  |  |  |  | 20 |  |  |  | 25 |  |  |  |  | 30 |

```
gca cag ttg ttt gca gaa gat gag cag gtc aag gcc gca cgt ccg ctc      278
Ala Gln Leu Phe Ala Glu Asp Glu Gln Val Lys Ala Ala Arg Pro Leu
 15              20                  25                  30 gaa gcg gtg agc gcg gcg gtg agc gcg ccc ggt atg cgg ctg gcg cag      326
Glu Ala Val Ser Ala Ala Val Ser Ala Pro Gly Met Arg Leu Ala Gln
                 35                  40                  45 atc gcc gcc act gtt atg gcg ggt tac gcc gac cgc ccg gcc gcc ggg      374
Ile Ala Ala Thr Val Met Ala Gly Tyr Ala Asp Arg Pro Ala Ala Gly
                     50                  55                  60 cag cgt gcg ttc gaa ctg aac acc gac gac gcg acg ggc cgc acc tcg      422
Gln Arg Ala Phe Glu Leu Asn Thr Asp Asp Ala Thr Gly Arg Thr Ser
                 65                  70                  75 ctg cgg tta ctt ccc cga ttc gag acc atc acc tat cgc gaa ctg tgg      470
Leu Arg Leu Leu Pro Arg Phe Glu Thr Ile Thr Tyr Arg Glu Leu Trp
 80                  85                  90 cag cga gtc ggc gag gtt gcc gcg gcc tgg cat cat gat ccc gag aac      518
Gln Arg Val Gly Glu Val Ala Ala Ala Trp His His Asp Pro Glu Asn
 95                 100                 105                 110 ccc ttg cgc gca ggt gat ttc gtc gcc ctg ctc ggc ttc acc agc atc      566
Pro Leu Arg Ala Gly Asp Phe Val Ala Leu Leu Gly Phe Thr Ser Ile
                115                 120                 125 gac tac gcc acc ctc gac ctg gcc gat atc cac ctc ggc gcg gtt acc      614
Asp Tyr Ala Thr Leu Asp Leu Ala Asp Ile His Leu Gly Ala Val Thr
                130                 135                 140 gtg ccg ttg cag gcc agc gcg gcg gtg tcc cag ctg atc gct atc ctc      662
Val Pro Leu Gln Ala Ser Ala Ala Val Ser Gln Leu Ile Ala Ile Leu
                145                 150                 155 acc gag act tcg ccg cgg ctg ctc gcc tcg acc ccg gag cac ctc gat      710
Thr Glu Thr Ser Pro Arg Leu Leu Ala Ser Thr Pro Glu His Leu Asp
160                 165                 170 gcg gcg gtc gag tgc cta ctc gcg ggc acc aca ccg gaa cga ctg gtg      758
Ala Ala Val Glu Cys Leu Leu Ala Gly Thr Thr Pro Glu Arg Leu Val
175                 180                 185                 190 gtc ttc gac tac cac ccc gag gac gac gac cag cgt gcg gcc ttc gaa      806
Val Phe Asp Tyr His Pro Glu Asp Asp Asp Gln Arg Ala Ala Phe Glu
                195                 200                 205 tcc gcc cgc cgc cgc ctt gcc gac gcg ggc agc tcg gtg atc gtc gaa      854
Ser Ala Arg Arg Arg Leu Ala Asp Ala Gly Ser Ser Val Ile Val Glu
                210                 215                 220 acg ctc gat gcc gtg cgt gcc cgg ggc cgc gac tta ccg gcc gcg cca      902
Thr Leu Asp Ala Val Arg Ala Arg Gly Arg Asp Leu Pro Ala Ala Pro
                225                 230                 235 ctg ttc gtt ccc gac acc gac gac ccg ctg gcc ctg ctg atc tac          950
Leu Phe Val Pro Asp Thr Asp Asp Asp Pro Leu Ala Leu Leu Ile Tyr
240                 245                 250 acc tcc ggc agc acc gga acg ccg aag ggc gcg atg tac acc aat cgg      998
Thr Ser Gly Ser Thr Gly Thr Pro Lys Gly Ala Met Tyr Thr Asn Arg
255                 260                 265                 270 ttg gcc gcc acg atg tgg cag ggg aac tcg atg ctg cag ggg aac tcg     1046
Leu Ala Ala Thr Met Trp Gln Gly Asn Ser Met Leu Gln Gly Asn Ser
                275                 280                 285 caa cgg gtc ggg atc aat ctc aac tac atg ccg atg agc cac atc gcc     1094
Gln Arg Val Gly Ile Asn Leu Asn Tyr Met Pro Met Ser His Ile Ala
                290                 295                 300 ggt cgc ata tcg ctg ttc ggc gtg ctc gct cgc ggt ggc acc gca tac     1142
Gly Arg Ile Ser Leu Phe Gly Val Leu Ala Arg Gly Gly Thr Ala Tyr
                305                 310                 315 ttc gcg gcc aag agc gac atg tcg aca ctg ttc gaa gac atc ggc ttg     1190
```

```
                Phe Ala Ala Lys Ser Asp Met Ser Thr Leu Phe Glu Asp Ile Gly Leu
                    320                 325                 330 gta cgt ccc acc gag atc ttc ttc gtc ccg cgc gtg tgc gac atg gtc          1238
Val Arg Pro Thr Glu Ile Phe Phe Val Pro Arg Val Cys Asp Met Val
335                 340                 345                 350 ttc cag cgc tat cag agc gag ctg gac cgg cgc tcg gtg gcg ggc gcc          1286
Phe Gln Arg Tyr Gln Ser Glu Leu Asp Arg Arg Ser Val Ala Gly Ala
                355                 360                 365 gac ctg gac acg ctc gat cgg gaa gtg aaa gcc gac ctc cgg cag aac          1334
Asp Leu Asp Thr Leu Asp Arg Glu Val Lys Ala Asp Leu Arg Gln Asn
            370                 375                 380 tac ctc ggt ggg cgc ttc ctg gtg gcg gtc gtc ggc agc gcg ccg ctg          1382
Tyr Leu Gly Gly Arg Phe Leu Val Ala Val Val Gly Ser Ala Pro Leu
        385                 390                 395 gcc gcg gag atg aag acg ttc atg gag tcc gtc ctc gat ctg cca ctg          1430
Ala Ala Glu Met Lys Thr Phe Met Glu Ser Val Leu Asp Leu Pro Leu
    400                 405                 410 cac gac ggg tac ggg tcg acc gag gcg ggc gca agc gtg ctg ctc gac          1478
His Asp Gly Tyr Gly Ser Thr Glu Ala Gly Ala Ser Val Leu Leu Asp
415                 420                 425                 430 aac cag atc cag cgg ccg ccg gtg ctc gat tac aag ctc gtc gac gtg          1526
Asn Gln Ile Gln Arg Pro Pro Val Leu Asp Tyr Lys Leu Val Asp Val
                435                 440                 445 ccc gaa ctg ggt tac ttc cgc acc gac cgg ccg cat ccg cgc ggt gag          1574
Pro Glu Leu Gly Tyr Phe Arg Thr Asp Arg Pro His Pro Arg Gly Glu
            450                 455                 460 ctg ttg ttg aag gcg gag acc acg att ccg ggc tac tac aag cgg ccc          1622
Leu Leu Leu Lys Ala Glu Thr Thr Ile Pro Gly Tyr Tyr Lys Arg Pro
        465                 470                 475 gag gtc acc gcg gag atc ttc gac gag gac ggc ttc tac aag acc ggc          1670
Glu Val Thr Ala Glu Ile Phe Asp Glu Asp Gly Phe Tyr Lys Thr Gly
    480                 485                 490 gat atc gtg gcc gag ctc gag cac gat cgg ctg gtc tat gtc gac cgt          1718
Asp Ile Val Ala Glu Leu Glu His Asp Arg Leu Val Tyr Val Asp Arg
495                 500                 505                 510 cgc aac aat gtg ctc aaa ctg tcg cag ggc gag ttc gtg acc gtc gcc          1766
Arg Asn Asn Val Leu Lys Leu Ser Gln Gly Glu Phe Val Thr Val Ala
                515                 520                 525 cat ctc gag gcc gtg ttc gcc agc agc ccg ctg atc cgg cag atc ttc          1814
His Leu Glu Ala Val Phe Ala Ser Ser Pro Leu Ile Arg Gln Ile Phe
            530                 535                 540 atc tac ggc agc agc gaa cgt tcc tat ctg ctc gcg gtg atc gtc ccc          1862
Ile Tyr Gly Ser Ser Glu Arg Ser Tyr Leu Leu Ala Val Ile Val Pro
        545                 550                 555 acc gac gac gcg ctg cgc ggc cgc gac acc gcc acc ttg aaa tcg gca          1910
Thr Asp Asp Ala Leu Arg Gly Arg Asp Thr Ala Thr Leu Lys Ser Ala
    560                 565                 570 ctg gcc gaa tcg att cag cgc atc gcc aag gac gcg aac ctg cag ccc          1958
Leu Ala Glu Ser Ile Gln Arg Ile Ala Lys Asp Ala Asn Leu Gln Pro
575                 580                 585                 590 tac gag att ccg cgc gat ttc ctg atc gag acc gag ccg ttc acc atc          2006
Tyr Glu Ile Pro Arg Asp Phe Leu Ile Glu Thr Glu Pro Phe Thr Ile
                595                 600                 605 gcc aac gga ctg ctc tcc ggc atc gcg aag ctg ctg cgc ccc aat ctg          2054
Ala Asn Gly Leu Leu Ser Gly Ile Ala Lys Leu Leu Arg Pro Asn Leu
            610                 615                 620 aag gaa cgc tac ggc gct cag ctg gag cag atg tac acc gat ctc gcg          2102
Lys Glu Arg Tyr Gly Ala Gln Leu Glu Gln Met Tyr Thr Asp Leu Ala
        625                 630                 635
```

```
aca ggc cag gcc gat gag ctg ctc gcc ctg cgc cgc gaa gcc gcc gac    2150
Thr Gly Gln Ala Asp Glu Leu Leu Ala Leu Arg Arg Glu Ala Ala Asp
        640                 645                 650 ctg ccg gtg ctc gaa acc gtc agc cgg gca gcg aaa gcg atg ctc ggc    2198
Leu Pro Val Leu Glu Thr Val Ser Arg Ala Ala Lys Ala Met Leu Gly
655                 660                 665                 670 gtc gcc tcc gcc gat atg cgt ccc gac gcg cac ttc acc gac ctg ggc    2246
Val Ala Ser Ala Asp Met Arg Pro Asp Ala His Phe Thr Asp Leu Gly
                675                 680                 685 ggc gat tcc ctt tcc gcg ctg tcg ttc tcg aac ctg ctg cac gag atc    2294
Gly Asp Ser Leu Ser Ala Leu Ser Phe Ser Asn Leu Leu His Glu Ile
                690                 695                 700 ttc ggg gtc gag gtg ccg gtg ggt gtc gtc gtc agc ccg gcg aac gag    2342
Phe Gly Val Glu Val Pro Val Gly Val Val Val Ser Pro Ala Asn Glu
            705                 710                 715 ctg cgc gat ctg gcg aat tac att gag gcg gaa cgc aac tcg ggc gcg    2390
Leu Arg Asp Leu Ala Asn Tyr Ile Glu Ala Glu Arg Asn Ser Gly Ala
720                 725                 730 aag cgt ccc acc ttc acc tcg gtg cac ggc ggc ggt tcc gag atc cgc    2438
Lys Arg Pro Thr Phe Thr Ser Val His Gly Gly Gly Ser Glu Ile Arg
735                 740                 745                 750 gcc gcc gat ctg acc ctc gac aag ttc atc gat gcc cgc acc ctg gcc    2486
Ala Ala Asp Leu Thr Leu Asp Lys Phe Ile Asp Ala Arg Thr Leu Ala
                755                 760                 765 gcc gcc gac agc att ccg cac gcg ccg gtg cca gcg cag acg gtg ctg    2534
Ala Ala Asp Ser Ile Pro His Ala Pro Val Pro Ala Gln Thr Val Leu
                770                 775                 780 ctg acc ggc gcg aac ggc tac ctc ggc cgg ttc ctg tgc ctg gaa tgg    2582
Leu Thr Gly Ala Asn Gly Tyr Leu Gly Arg Phe Leu Cys Leu Glu Trp
            785                 790                 795 ctg gag cgg ctg gac aag acg ggt ggc acg ctg atc tgc gtc gtg cgc    2630
Leu Glu Arg Leu Asp Lys Thr Gly Gly Thr Leu Ile Cys Val Val Arg
800                 805                 810 ggt agt gac gcg gcc gcg gcc cgt aaa cgg ctg gac tcg gcg ttc gac    2678
Gly Ser Asp Ala Ala Ala Ala Arg Lys Arg Leu Asp Ser Ala Phe Asp
815                 820                 825                 830 agc ggc gat ccc ggc ctg ctc gag cac tac cag caa ctg gcc gca cgg    2726
Ser Gly Asp Pro Gly Leu Leu Glu His Tyr Gln Gln Leu Ala Ala Arg
                835                 840                 845 acc ctg gaa gtc ctc gcc ggt gat atc ggc gac ccg aat ctc ggt ctg    2774
Thr Leu Glu Val Leu Ala Gly Asp Ile Gly Asp Pro Asn Leu Gly Leu
                850                 855                 860 gac gac gcg act tgg cag cgg ttg gcc gaa acc gtc gac ctg atc gtc    2822
Asp Asp Ala Thr Trp Gln Arg Leu Ala Glu Thr Val Asp Leu Ile Val
            865                 870                 875 cat ccc gcc gcg ttg gtc aac cac gtc ctt ccc tac acc cag ctg ttc    2870
His Pro Ala Ala Leu Val Asn His Val Leu Pro Tyr Thr Gln Leu Phe
880                 885                 890 ggc ccc aat gtc gtc ggc acc gcc gaa atc gtc cgg ttg gcg atc acg    2918
Gly Pro Asn Val Val Gly Thr Ala Glu Ile Val Arg Leu Ala Ile Thr
895                 900                 905                 910 gcg cgg cgc aag ccg gtc acc tac ctg tcg acc gtc gga gtg gcc gac    2966
Ala Arg Arg Lys Pro Val Thr Tyr Leu Ser Thr Val Gly Val Ala Asp
                915                 920                 925 cag gtc gac ccg gcg gag tat cag gag gac agc gac gtc cgc gag atg    3014
Gln Val Asp Pro Ala Glu Tyr Gln Glu Asp Ser Asp Val Arg Glu Met
                930                 935                 940 agc gcg gtg cgc gtc gtg cgc gag agt tac gcc aac ggc tac ggc aac    3062
Ser Ala Val Arg Val Val Arg Glu Ser Tyr Ala Asn Gly Tyr Gly Asn
            945                 950                 955
```

-continued

| | |
|---|---|
| agc aag tgg gcg ggg gag gtc ctg ctg cgc gaa gca cac gat ctg tgt<br>Ser Lys Trp Ala Gly Glu Val Leu Leu Arg Glu Ala His Asp Leu Cys<br>960                        965                    970 | 3110 |
| ggc ttg ccg gtc gcg gtg ttc cgt tcg gac atg atc ctg gcg cac agc<br>Gly Leu Pro Val Ala Val Phe Arg Ser Asp Met Ile Leu Ala His Ser<br>975                        980                    985                    990 | 3158 |
| cgg tac gcg ggt cag ctc aac gtc cag gac gtg ttc acc cgg ctg atc<br>Arg Tyr Ala Gly Gln Leu Asn Val Gln Asp Val Phe Thr Arg Leu Ile<br>                        995                    1000                  1005 | 3206 |
| ctc agc ctg gtc gcc acc ggc atc gcg ccg tac tcg ttc tac cga<br>Leu Ser Leu Val Ala Thr Gly Ile Ala Pro Tyr Ser Phe Tyr Arg<br>          1010                    1015                  1020 | 3251 |
| acc gac gcg gac ggc aac cgg cag cgg gcc cac tac gac ggt ctg<br>Thr Asp Ala Asp Gly Asn Arg Gln Arg Ala His Tyr Asp Gly Leu<br>          1025                    1030                  1035 | 3296 |
| ccc gcc gat ttc acg gcg gcg gcg atc acc gcg ctc ggc atc caa<br>Pro Ala Asp Phe Thr Ala Ala Ala Ile Thr Ala Leu Gly Ile Gln<br>          1040                    1045                  1050 | 3341 |
| gcc acc gaa ggc ttc cgg acc tac gac gtg ctc aat ccg tac gac<br>Ala Thr Glu Gly Phe Arg Thr Tyr Asp Val Leu Asn Pro Tyr Asp<br>          1055                    1060                  1065 | 3386 |
| gat ggc atc tcc ctc gat gaa ttc gtc gac tgg ctc gtc gaa tcc<br>Asp Gly Ile Ser Leu Asp Glu Phe Val Asp Trp Leu Val Glu Ser<br>          1070                    1075                  1080 | 3431 |
| ggc cac ccg atc cag cgc atc acc gac tac agc gac tgg ttc cac<br>Gly His Pro Ile Gln Arg Ile Thr Asp Tyr Ser Asp Trp Phe His<br>          1085                    1090                  1095 | 3476 |
| cgt ttc gag acg gcg atc cgc gcg ctg ccg gaa aag caa cgc cag<br>Arg Phe Glu Thr Ala Ile Arg Ala Leu Pro Glu Lys Gln Arg Gln<br>          1100                    1105                  1110 | 3521 |
| gcc tcg gtg ctg ccg ttg ctg gac gcc tac cgc aac ccc tgc ccg<br>Ala Ser Val Leu Pro Leu Leu Asp Ala Tyr Arg Asn Pro Cys Pro<br>          1115                    1120                  1125 | 3566 |
| gcg gtc cgc ggc gcg ata ctc ccg gcc aag gag ttc caa gcg gcg<br>Ala Val Arg Gly Ala Ile Leu Pro Ala Lys Glu Phe Gln Ala Ala<br>          1130                    1135                  1140 | 3611 |
| gtg caa aca gcc aaa atc ggt ccg gaa cag gac atc ccg cat ttg<br>Val Gln Thr Ala Lys Ile Gly Pro Glu Gln Asp Ile Pro His Leu<br>          1145                    1150                  1155 | 3656 |
| tcc gcg cca ctg atc gat aag tac gtc agc gat ctg gaa ctg ctt<br>Ser Ala Pro Leu Ile Asp Lys Tyr Val Ser Asp Leu Glu Leu Leu<br>          1160                    1165                  1170 | 3701 |
| cag ctg ctc tga cgg ata tca ggc cgc cgc gcg cac ctc gtc ggt<br>Gln Leu Leu     Arg Ile Ser Gly Arg Arg Ala His Leu Val Gly<br>                        1175                    1180                  1185 | 3746 |
| gcg ttc ggc gcc ttc gcg ccg gag gcg aaa cag gaa tac cgc cga<br>Ala Phe Gly Ala Phe Ala Pro Glu Ala Lys Gln Glu Tyr Arg Arg<br>          1190                    1195                  1200 | 3791 |
| gcc acc cag gac agc ggc gta gac gat gac gaa gct gtt gat cag<br>Ala Thr Gln Asp Ser Gly Val Asp Asp Asp Glu Ala Val Asp Gln<br>          1205                    1210                  1215 | 3836 |
| gac ctg ggc gac cgg cca cca cgg cgg gaa cag gaa cag ccc gac<br>Asp Leu Gly Asp Arg Pro Pro Arg Arg Glu Gln Glu Gln Pro Asp<br>          1220                    1225                  1230 | 3881 |
| gac aac gta gtc cgg gct gta ttc cca cgt cca cgc gcc gat cga<br>Asp Asn Val Val Arg Ala Val Phe Pro Arg Pro Arg Ala Asp Arg<br>          1235                    1240                  1245 | 3926 |
| gac gaa gag cgc ggc cga ggc aag cca cca cca cgg ctg cga ctg<br>Asp Glu Glu Arg Gly Arg Gly Lys Pro Pro Pro Arg Leu Arg Leu | 3971 |

-continued

```
                1250                    1255                    1260
cgc  cct  gtg  cag  tag  ata  gac  gaa  cag  ggg  aac  gaa  cca  cac  cca        4016
Arg  Pro  Val  Gln       Ile  Asp  Glu  Gln  Gly  Asn  Glu  Pro  His  Pro
                         1265                              1270 gtg  gtg  gtc  cca  gga  gaa  cgg  cga  gac  cgc  gca  ggc  ggt  gag  gcc        4061
Val  Val  Val  Pro  Gly  Glu  Arg  Arg  Asp  Arg  Ala  Gly  Gly  Glu  Ala
1275                     1280                         1285 ggc  gag  ggt  gac  cgc  gag  gag  ctg  ttc  gcc  acg  ccg  ata  cag  gcc        4106
Gly  Glu  Gly  Asp  Arg  Glu  Glu  Leu  Phe  Ala  Thr  Pro  Ile  Gln  Ala
1290                     1295                         1300 gat  ggt  gac  ggc  cag  act  cgc  cag  cgc  gac  gga  gcc  cgc  gat  gag        4151
Asp  Gly  Asp  Gly  Gln  Thr  Arg  Gln  Arg  Asp  Gly  Ala  Arg  Asp  Glu
1305                     1310                         1315 cag  cca  cag  cca  cac  cgg  cgc  cgg  gtg  atg  ggt  cag  gtg  cgc  gat        4196
Gln  Pro  Gln  Pro  His  Arg  Arg  Arg  Val  Met  Gly  Gln  Val  Arg  Asp
1320                     1325                         1330 ggc  gcc  gcg  gat  gga  ttg  att  gga  cgg  gtg  cat  atc  gtc  cgc  gat        4241
Gly  Ala  Ala  Asp  Gly  Leu  Ile  Gly  Arg  Val  His  Ile  Val  Arg  Asp
1335                     1340                         1345 ccg  att  gga  ctg  gaa  gaa  cgt  cga  ggt  cca  gta  ctg  ccg  gga  atc        4286
Pro  Ile  Gly  Leu  Glu  Glu  Arg  Arg  Gly  Pro  Val  Leu  Pro  Gly  Ile
1350                     1355                         1360 ggc  ggg  cag  cac  gat  cca  ggc  gag  gac  gat  gga  cgc  gat  gaa  cac        4331
Gly  Gly  Gln  His  Asp  Pro  Gly  Glu  Asp  Asp  Gly  Arg  Asp  Glu  His
1365                     1370                         1375 cgc  cac  ggc  ggt  gca  cgc  gga  ccg  cca  ctg  ccg  caa  cgc  gag  gaa        4376
Arg  His  Gly  Gly  Ala  Arg  Gly  Pro  Pro  Leu  Pro  Gln  Arg  Glu  Glu
1380                     1385                         1390 ttg  cac  gac  gaa  gta  gcc  agg  gac  gag  ctt  gat  gcc  cgc  cgc  cac        4421
Leu  His  Asp  Glu  Val  Ala  Arg  Asp  Glu  Leu  Asp  Ala  Arg  Arg  His
1395                     1400                         1405 ccc  gac  gcc  gag  gcc  gcg  cag  ctt  gct  gcg  gtc  ggg  ccg  gga  gaa        4466
Pro  Asp  Ala  Glu  Ala  Ala  Gln  Leu  Ala  Ala  Val  Gly  Pro  Gly  Glu
1410                     1415                         1420 gtc  cca  cag  cac  cag  cag  cat  cag  cat  cag  gtt  gat  ctg  gcc  gta        4511
Val  Pro  Gln  His  Gln  Gln  His  Gln  His  Gln  Val  Asp  Leu  Ala  Val
1425                     1430                         1435 gaa  cag  cgt  tgt  ccg  gac  ggg  ctc  gat  gaa  cgc  gca  ggt  gag  cgc        4556
Glu  Gln  Arg  Cys  Pro  Asp  Gly  Leu  Asp  Glu  Arg  Ala  Gly  Glu  Arg
1440                     1445                         1450 cag  tag  ggc  gct  gac  gac  ggc  cag  tct  ggc  gtt  gat  ccg  gta  cc         4600
Gln       Gly  Ala  Asp  Asp  Gly  Gln  Ser  Gly  Val  Asp  Pro  Val
1455           1460                         1465
```

<210> SEQ ID NO 2
<211> LENGTH: 1174
<212> TYPE: PRT
<213> ORGANISM: Nocardia

<400> SEQUENCE: 2

Met Ala Val Asp Ser Pro Asp Glu Arg Leu Gln Arg Arg Ile Ala Gln
1               5                   10                  15

Leu Phe Ala Glu Asp Glu Gln Val Lys Ala Ala Arg Pro Leu Glu Ala
            20                  25                  30

Val Ser Ala Ala Val Ser Ala Pro Gly Met Arg Leu Ala Gln Ile Ala
        35                  40                  45

Ala Thr Val Met Ala Gly Tyr Ala Asp Arg Pro Ala Ala Gly Gln Arg
    50                  55                  60

Ala Phe Glu Leu Asn Thr Asp Asp Ala Thr Gly Arg Thr Ser Leu Arg

-continued

```
            65                  70                  75                  80
Leu Leu Pro Arg Phe Glu Thr Ile Thr Tyr Arg Glu Leu Trp Gln Arg
                    85                  90                  95
Val Gly Glu Val Ala Ala Ala Trp His His Asp Pro Glu Asn Pro Leu
                    100                 105                 110
Arg Ala Gly Asp Phe Val Ala Leu Leu Gly Phe Thr Ser Ile Asp Tyr
                    115                 120                 125
Ala Thr Leu Asp Leu Ala Asp Ile His Leu Gly Ala Val Thr Val Pro
                    130                 135                 140
Leu Gln Ala Ser Ala Ala Val Ser Gln Leu Ile Ala Ile Leu Thr Glu
145                 150                 155                 160
Thr Ser Pro Arg Leu Leu Ala Ser Thr Pro Glu His Leu Asp Ala Ala
                    165                 170                 175
Val Glu Cys Leu Leu Ala Gly Thr Thr Pro Glu Arg Leu Val Val Phe
                    180                 185                 190
Asp Tyr His Pro Glu Asp Asp Gln Arg Ala Ala Phe Glu Ser Ala
                    195                 200                 205
Arg Arg Arg Leu Ala Asp Ala Gly Ser Ser Val Ile Val Glu Thr Leu
                    210                 215                 220
Asp Ala Val Arg Ala Arg Gly Arg Asp Leu Pro Ala Ala Pro Leu Phe
225                 230                 235                 240
Val Pro Asp Thr Asp Asp Pro Leu Ala Leu Leu Ile Tyr Thr Ser
                    245                 250                 255
Gly Ser Thr Gly Thr Pro Lys Gly Ala Met Tyr Thr Asn Arg Leu Ala
                    260                 265                 270
Ala Thr Met Trp Gln Gly Asn Ser Met Leu Gln Gly Asn Ser Gln Arg
                    275                 280                 285
Val Gly Ile Asn Leu Asn Tyr Met Pro Met Ser His Ile Ala Gly Arg
                    290                 295                 300
Ile Ser Leu Phe Gly Val Leu Ala Arg Gly Gly Thr Ala Tyr Phe Ala
305                 310                 315                 320
Ala Lys Ser Asp Met Ser Thr Leu Phe Glu Asp Ile Gly Leu Val Arg
                    325                 330                 335
Pro Thr Glu Ile Phe Phe Val Pro Arg Val Cys Asp Met Val Phe Gln
                    340                 345                 350
Arg Tyr Gln Ser Glu Leu Asp Arg Arg Ser Val Ala Gly Ala Asp Leu
                    355                 360                 365
Asp Thr Leu Asp Arg Glu Val Lys Ala Asp Leu Arg Gln Asn Tyr Leu
                    370                 375                 380
Gly Gly Arg Phe Leu Val Ala Val Val Gly Ser Ala Pro Leu Ala Ala
385                 390                 395                 400
Glu Met Lys Thr Phe Met Glu Ser Val Leu Asp Leu Pro Leu His Asp
                    405                 410                 415
Gly Tyr Gly Ser Thr Glu Ala Gly Ala Ser Val Leu Leu Asp Asn Gln
                    420                 425                 430
Ile Gln Arg Pro Pro Val Leu Asp Tyr Lys Leu Val Asp Val Pro Glu
                    435                 440                 445
Leu Gly Tyr Phe Arg Thr Asp Arg Pro His Pro Arg Gly Glu Leu Leu
                    450                 455                 460
Leu Lys Ala Glu Thr Thr Ile Pro Gly Tyr Tyr Lys Arg Pro Glu Val
465                 470                 475                 480
Thr Ala Glu Ile Phe Asp Glu Asp Gly Phe Tyr Lys Thr Gly Asp Ile
                    485                 490                 495
```

```
Val Ala Glu Leu Glu His Asp Arg Leu Val Tyr Val Asp Arg Arg Asn
            500                 505                 510

Asn Val Leu Lys Leu Ser Gln Gly Glu Phe Val Thr Val Ala His Leu
            515                 520                 525

Glu Ala Val Phe Ala Ser Ser Pro Leu Ile Arg Gln Ile Phe Ile Tyr
            530                 535                 540

Gly Ser Ser Glu Arg Ser Tyr Leu Leu Ala Val Ile Val Pro Thr Asp
545                 550                 555                 560

Asp Ala Leu Arg Gly Arg Asp Thr Ala Thr Leu Lys Ser Ala Leu Ala
                565                 570                 575

Glu Ser Ile Gln Arg Ile Ala Lys Asp Ala Asn Leu Gln Pro Tyr Glu
            580                 585                 590

Ile Pro Arg Asp Phe Leu Ile Glu Thr Glu Pro Phe Thr Ile Ala Asn
            595                 600                 605

Gly Leu Leu Ser Gly Ile Ala Lys Leu Leu Arg Pro Asn Leu Lys Glu
            610                 615                 620

Arg Tyr Gly Ala Gln Leu Glu Gln Met Tyr Thr Asp Leu Ala Thr Gly
625                 630                 635                 640

Gln Ala Asp Glu Leu Leu Ala Leu Arg Arg Glu Ala Ala Asp Leu Pro
                645                 650                 655

Val Leu Glu Thr Val Ser Arg Ala Ala Lys Ala Met Leu Gly Val Ala
            660                 665                 670

Ser Ala Asp Met Arg Pro Asp Ala His Phe Thr Asp Leu Gly Gly Asp
            675                 680                 685

Ser Leu Ser Ala Leu Ser Phe Ser Asn Leu Leu His Glu Ile Phe Gly
            690                 695                 700

Val Glu Val Pro Val Gly Val Val Ser Pro Ala Asn Glu Leu Arg
705                 710                 715                 720

Asp Leu Ala Asn Tyr Ile Glu Ala Glu Arg Asn Ser Gly Ala Lys Arg
                725                 730                 735

Pro Thr Phe Thr Ser Val His Gly Gly Gly Ser Glu Ile Arg Ala Ala
            740                 745                 750

Asp Leu Thr Leu Asp Lys Phe Ile Asp Ala Arg Thr Leu Ala Ala Ala
            755                 760                 765

Asp Ser Ile Pro His Ala Pro Val Pro Ala Gln Thr Val Leu Leu Thr
            770                 775                 780

Gly Ala Asn Gly Tyr Leu Gly Arg Phe Leu Cys Leu Glu Trp Leu Glu
785                 790                 795                 800

Arg Leu Asp Lys Thr Gly Gly Thr Leu Ile Cys Val Val Arg Gly Ser
                805                 810                 815

Asp Ala Ala Ala Arg Lys Arg Leu Asp Ser Ala Phe Asp Ser Gly
            820                 825                 830

Asp Pro Gly Leu Leu Glu His Tyr Gln Gln Leu Ala Ala Arg Thr Leu
            835                 840                 845

Glu Val Leu Ala Gly Asp Ile Gly Asp Pro Asn Leu Gly Leu Asp Asp
850                 855                 860

Ala Thr Trp Gln Arg Leu Ala Glu Thr Val Asp Leu Ile Val His Pro
865                 870                 875                 880

Ala Ala Leu Val Asn His Val Leu Pro Tyr Thr Gln Leu Phe Gly Pro
                885                 890                 895

Asn Val Val Gly Thr Ala Glu Ile Val Arg Leu Ala Ile Thr Ala Arg
            900                 905                 910
```

```
Arg Lys Pro Val Thr Tyr Leu Ser Thr Val Gly Val Ala Asp Gln Val
        915                 920                 925

Asp Pro Ala Glu Tyr Gln Glu Asp Ser Asp Val Arg Glu Met Ser Ala
        930                 935                 940

Val Arg Val Val Arg Glu Ser Tyr Ala Asn Gly Tyr Gly Asn Ser Lys
945                 950                 955                 960

Trp Ala Gly Glu Val Leu Leu Arg Glu Ala His Asp Leu Cys Gly Leu
        965                 970                 975

Pro Val Ala Val Phe Arg Ser Asp Met Ile Leu Ala His Ser Arg Tyr
        980                 985                 990

Ala Gly Gln Leu Asn Val Gln Asp Val Phe Thr Arg Leu Ile Leu Ser
        995                 1000                1005

Leu Val Ala Thr Gly Ile Ala Pro Tyr Ser Phe Tyr Arg Thr Asp
        1010                1015                1020

Ala Asp Gly Asn Arg Gln Ala His Tyr Asp Gly Leu Pro Ala
        1025                1030                1035

Asp Phe Thr Ala Ala Ala Ile Thr Ala Leu Gly Ile Gln Ala Thr
        1040                1045                1050

Glu Gly Phe Arg Thr Tyr Asp Val Leu Asn Pro Tyr Asp Asp Gly
        1055                1060                1065

Ile Ser Leu Asp Glu Phe Val Asp Trp Leu Val Glu Ser Gly His
        1070                1075                1080

Pro Ile Gln Arg Ile Thr Asp Tyr Ser Asp Trp Phe His Arg Phe
        1085                1090                1095

Glu Thr Ala Ile Arg Ala Leu Pro Glu Lys Gln Arg Gln Ala Ser
        1100                1105                1110

Val Leu Pro Leu Leu Asp Ala Tyr Arg Asn Pro Cys Pro Ala Val
        1115                1120                1125

Arg Gly Ala Ile Leu Pro Ala Lys Glu Phe Gln Ala Ala Val Gln
        1130                1135                1140

Thr Ala Lys Ile Gly Pro Glu Gln Asp Ile Pro His Leu Ser Ala
        1145                1150                1155

Pro Leu Ile Asp Lys Tyr Val Ser Asp Leu Glu Leu Leu Gln Leu
        1160                1165                1170

Leu

<210> SEQ ID NO 3
<211> LENGTH: 90
<212> TYPE: PRT
<213> ORGANISM: Nocardia

<400> SEQUENCE: 3

Arg Ile Ser Gly Arg Ala His Leu Val Gly Ala Phe Gly Ala Phe
1               5                   10                  15

Ala Pro Glu Ala Lys Gln Glu Tyr Arg Arg Ala Thr Gln Asp Ser Gly
                20                  25                  30

Val Asp Asp Asp Glu Ala Val Asp Gln Asp Leu Gly Asp Arg Pro Pro
            35                  40                  45

Arg Arg Glu Gln Glu Gln Pro Asp Asp Asn Val Val Arg Ala Val Phe
        50                  55                  60

Pro Arg Pro Arg Ala Asp Arg Asp Glu Glu Arg Gly Arg Gly Lys Pro
65                  70                  75                  80

Pro Pro Arg Leu Arg Leu Arg Pro Val Gln
                85                  90
```

<210> SEQ ID NO 4
<211> LENGTH: 191
<212> TYPE: PRT
<213> ORGANISM: Nocardia

<400> SEQUENCE: 4

Ile Asp Glu Gln Gly Asn Glu Pro His Pro Val Val Pro Gly Glu
1               5                   10                  15

Arg Arg Asp Arg Ala Gly Gly Glu Ala Gly Gly Asp Arg Glu Glu
                20                  25                  30

Leu Phe Ala Thr Pro Ile Gln Ala Asp Gly Asp Gly Gln Thr Arg Gln
                35                  40                  45

Arg Asp Gly Ala Arg Asp Glu Gln Pro Gln Pro His Arg Arg Arg Val
    50                  55                  60

Met Gly Gln Val Arg Asp Gly Ala Ala Asp Gly Leu Ile Gly Arg Val
65                  70                  75                  80

His Ile Val Arg Asp Pro Ile Gly Leu Glu Glu Arg Arg Gly Pro Val
                85                  90                  95

Leu Pro Gly Ile Gly Gly Gln His Asp Pro Gly Glu Asp Asp Gly Arg
                100                 105                 110

Asp Glu His Arg His Gly Gly Ala Arg Gly Pro Pro Leu Pro Gln Arg
                115                 120                 125

Glu Glu Leu His Asp Glu Val Ala Arg Asp Glu Leu Asp Ala Arg Arg
    130                 135                 140

His Pro Asp Ala Glu Ala Ala Gln Leu Ala Ala Val Gly Pro Gly Glu
145                 150                 155                 160

Val Pro Gln His Gln Gln His Gln His Gln Val Asp Leu Ala Val Glu
                165                 170                 175

Gln Arg Cys Pro Asp Gly Leu Asp Glu Arg Ala Gly Glu Arg Gln
                180                 185                 190

<210> SEQ ID NO 5
<211> LENGTH: 12
<212> TYPE: PRT
<213> ORGANISM: Nocardia

<400> SEQUENCE: 5

Gly Ala Asp Asp Gly Gln Ser Gly Val Asp Pro Val
1               5                   10

<210> SEQ ID NO 6
<211> LENGTH: 16
<212> TYPE: PRT
<213> ORGANISM: Nocardia

<400> SEQUENCE: 6

Ala Val Asp Ser Pro Asp Glu Arg Leu Gln Arg Arg Ile Ala Gln Leu
1               5                   10                  15

<210> SEQ ID NO 7
<211> LENGTH: 16
<212> TYPE: PRT
<213> ORGANISM: Nocardia

<400> SEQUENCE: 7

Lys Leu Ser Gln Gly Glu Phe Val Thr Val Ala His Leu Glu Ala Val
1               5                   10                  15

<210> SEQ ID NO 8

```
<211> LENGTH: 8
<212> TYPE: PRT
<213> ORGANISM: hypothetical
<220> FEATURE:
<221> NAME/KEY: MISC_FEATURE
<222> LOCATION: (4)..(4)
<223> OTHER INFORMATION: "X" can ba any animo acid
<220> FEATURE:
<221> NAME/KEY: MISC_FEATURE
<222> LOCATION: (6)..(6)
<223> OTHER INFORMATION: "X" can ba any animo acid
<220> FEATURE:
<221> NAME/KEY: MISC_FEATURE
<222> LOCATION: (7)..(7)
<223> OTHER INFORMATION: "X" can ba any animo acid

<400> SEQUENCE: 8

Leu Gly Gly Xaa Ser Xaa Xaa Ala
1               5

<210> SEQ ID NO 9
<211> LENGTH: 7
<212> TYPE: PRT
<213> ORGANISM: hypothetical
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (4)..(4)
<223> OTHER INFORMATION: X can be any amino acid

<400> SEQUENCE: 9

Gly Tyr Xaa Xaa Ser Lys Trp
1               5

<210> SEQ ID NO 10
<211> LENGTH: 7
<212> TYPE: PRT
<213> ORGANISM: hypothetical
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (5)..(5)
<223> OTHER INFORMATION: X can be any amino acid

<400> SEQUENCE: 10

Gly Xaa Xaa Gly Xaa Leu Gly
1               5

<210> SEQ ID NO 11
<211> LENGTH: 18
<212> TYPE: DNA
<213> ORGANISM: Nocardia

<400> SEQUENCE: 11
gtsgattcac csgatgag                                                 18

<210> SEQ ID NO 12
<211> LENGTH: 18
<212> TYPE: DNA
<213> ORGANISM: Nocardia
```

-continued

```
<400> SEQUENCE: 12
ccsgatgarc gsctacag                                                   18

<210> SEQ ID NO 13
<211> LENGTH: 18
<212> TYPE: DNA
<213> ORGANISM: Nocardia

<400> SEQUENCE: 13
tgsgcsacsg tsacgaac                                                   18

<210> SEQ ID NO 14
<211> LENGTH: 19
<212> TYPE: DNA
<213> ORGANISM: Nocardia

<400> SEQUENCE: 14
sacgaaytcs ccctgsgac                                                  19

<210> SEQ ID NO 15
<211> LENGTH: 25
<212> TYPE: DNA
<213> ORGANISM: Nocardia

<400> SEQUENCE: 15
ggtcgggatc aatctcaact acatg                                           25

<210> SEQ ID NO 16
<211> LENGTH: 26
<212> TYPE: DNA
<213> ORGANISM: Nocardia

<400> SEQUENCE: 16
cttcagctgc tctgacggat atcagc                                          26

<210> SEQ ID NO 17
<211> LENGTH: 24
<212> TYPE: DNA
<213> ORGANISM: Nocardia

<400> SEQUENCE: 17
ctgctcatct tctgcaaaca actg                                            24

<210> SEQ ID NO 18
<211> LENGTH: 31
<212> TYPE: DNA
<213> ORGANISM: Nocardia

<400> SEQUENCE: 18
cgcggatccg cagtggattc accggatgag c                                    31

<210> SEQ ID NO 19
<211> LENGTH: 32
<212> TYPE: DNA
<213> ORGANISM: Nocardia

<400> SEQUENCE: 19
cggggtaccc ctgatatccg tcagagcagc tg                                   32

<210> SEQ ID NO 20
<211> LENGTH: 20
<212> TYPE: DNA
<213> ORGANISM: Nocardia
```

```
<400> SEQUENCE: 20
taatacgact cactataggg                                            20

<210> SEQ ID NO 21
<211> LENGTH: 24
<212> TYPE: DNA
<213> ORGANISM: Nocardia

<400> SEQUENCE: 21
catacgattt aggtgacact atag                                       24

<210> SEQ ID NO 22
<211> LENGTH: 18
<212> TYPE: DNA
<213> ORGANISM: Nocardia

<400> SEQUENCE: 22
caggaaacag ctatgacc                                              18

<210> SEQ ID NO 23
<211> LENGTH: 21
<212> TYPE: DNA
<213> ORGANISM: Nocardia

<400> SEQUENCE: 23
ctcgacctgg ccgatatcca c                                          21

<210> SEQ ID NO 24
<211> LENGTH: 20
<212> TYPE: DNA
<213> ORGANISM: Nocardia

<400> SEQUENCE: 24
gaggacggct tctacaagac                                            20

<210> SEQ ID NO 25
<211> LENGTH: 21
<212> TYPE: DNA
<213> ORGANISM: Nocardia

<400> SEQUENCE: 25
gacgcgcact tcaccgacct g                                          21

<210> SEQ ID NO 26
<211> LENGTH: 20
<212> TYPE: DNA
<213> ORGANISM: Nocardia

<400> SEQUENCE: 26
gtcgacctga tcgtccatcc                                            20

<210> SEQ ID NO 27
<211> LENGTH: 19
<212> TYPE: DNA
<213> ORGANISM: Nocardia

<400> SEQUENCE: 27
acctacgacg tgctcaatc                                             19

<210> SEQ ID NO 28
<211> LENGTH: 19
<212> TYPE: DNA
```

<213> ORGANISM: Nocardia

<400> SEQUENCE: 28
cgtacgacga tggcatctc                                                       19

<210> SEQ ID NO 29
<211> LENGTH: 21
<212> TYPE: DNA
<213> ORGANISM: Nocardia

<400> SEQUENCE: 29
gtggatatcg gccaggtcga g                                                    21

<210> SEQ ID NO 30
<211> LENGTH: 19
<212> TYPE: DNA
<213> ORGANISM: Nocardia

<400> SEQUENCE: 30
ggtggcagga tggaatcgg                                                       19

<210> SEQ ID NO 31
<211> LENGTH: 20
<212> TYPE: DNA
<213> ORGANISM: Nocardia

<400> SEQUENCE: 31
cgtcgattcg cgattccctg                                                      20

<210> SEQ ID NO 32
<211> LENGTH: 1168
<212> TYPE: PRT
<213> ORGANISM: M. tuberculosis

<400> SEQUENCE: 32

Met Ser Ile Asn Asp Gln Arg Leu Thr Arg Arg Val Glu Asp Leu Tyr
1               5                   10                  15

Ala Ser Asp Ala Gln Phe Ala Ala Ala Ser Pro Asn Glu Ala Ile Thr
            20                  25                  30

Gln Ala Ile Asp Gln Pro Gly Val Ala Leu Pro Gln Leu Ile Arg Met
        35                  40                  45

Val Met Glu Gly Tyr Ala Asp Arg Pro Ala Leu Gly Gln Arg Ala Leu
    50                  55                  60

Arg Phe Val Thr Asp Pro Asp Ser Gly Arg Thr Met Val Glu Leu Leu
65                  70                  75                  80

Pro Arg Phe Glu Thr Ile Thr Tyr Arg Glu Leu Trp Ala Arg Ala Gly
                85                  90                  95

Thr Leu Ala Thr Ala Leu Ser Ala Glu Pro Ala Ile Arg Pro Gly Asp
            100                 105                 110

Arg Val Cys Val Leu Gly Phe Asn Ser Val Asp Tyr Thr Thr Ile Asp
        115                 120                 125

Ile Ala Leu Ile Arg Leu Gly Ala Val Ser Val Pro Leu Gln Thr Ser
    130                 135                 140

Ala Pro Val Thr Gly Leu Arg Pro Ile Val Thr Glu Thr Glu Pro Thr
145                 150                 155                 160

Met Ile Ala Thr Ser Ile Asp Asn Leu Gly Asp Ala Val Glu Val Leu
                165                 170                 175

Ala Gly His Ala Pro Ala Arg Leu Val Val Phe Asp Tyr His Gly Lys
            180                 185                 190

-continued

```
Val Asp Thr His Arg Glu Ala Val Glu Ala Arg Ala Arg Leu Ala
        195                 200                 205
Gly Ser Val Thr Ile Asp Thr Leu Ala Glu Leu Ile Glu Arg Gly Arg
    210                 215                 220
Ala Leu Pro Ala Thr Pro Ile Ala Asp Ser Ala Asp Asp Ala Leu Ala
225                 230                 235                 240
Leu Leu Ile Tyr Thr Ser Gly Ser Thr Gly Ala Pro Lys Gly Ala Met
                245                 250                 255
Tyr Arg Glu Ser Gln Val Met Ser Phe Trp Arg Lys Ser Ser Gly Trp
            260                 265                 270
Phe Glu Pro Ser Gly Tyr Pro Ser Ile Thr Leu Asn Phe Met Pro Met
        275                 280                 285
Ser His Val Gly Gly Arg Gln Val Leu Tyr Gly Thr Leu Ser Asn Gly
    290                 295                 300
Gly Thr Ala Tyr Phe Val Ala Lys Ser Asp Leu Ser Thr Leu Phe Glu
305                 310                 315                 320
Asp Leu Ala Leu Val Arg Pro Thr Glu Leu Cys Phe Val Pro Arg Ile
                325                 330                 335
Trp Asp Met Val Phe Ala Glu Phe His Ser Glu Val Asp Arg Arg Leu
            340                 345                 350
Val Asp Gly Ala Asp Arg Ala Ala Leu Glu Ala Gln Val Lys Ala Glu
        355                 360                 365
Leu Arg Glu Asn Val Leu Gly Gly Arg Phe Val Met Ala Leu Thr Gly
    370                 375                 380
Ser Ala Pro Ile Ser Ala Glu Met Thr Ala Trp Val Glu Ser Leu Leu
385                 390                 395                 400
Ala Asp Val His Leu Val Glu Gly Tyr Gly Ser Thr Glu Ala Gly Met
                405                 410                 415
Val Leu Asn Asp Gly Met Val Arg Arg Pro Ala Val Ile Asp Tyr Lys
            420                 425                 430
Leu Val Asp Val Pro Glu Leu Gly Tyr Phe Gly Thr Asp Gln Pro Tyr
        435                 440                 445
Pro Arg Gly Glu Leu Leu Val Lys Thr Gln Thr Met Phe Pro Gly Tyr
    450                 455                 460
Tyr Gln Arg Pro Asp Val Thr Ala Glu Val Phe Asp Pro Asp Gly Phe
465                 470                 475                 480
Tyr Arg Thr Gly Asp Ile Met Ala Lys Val Gly Pro Asp Gln Phe Val
                485                 490                 495
Tyr Leu Asp Arg Arg Asn Asn Val Leu Lys Leu Ser Gln Gly Glu Phe
            500                 505                 510
Ile Ala Val Ser Lys Leu Glu Ala Val Phe Gly Asp Ser Pro Leu Val
        515                 520                 525
Arg Gln Ile Phe Ile Tyr Gly Asn Ser Ala Arg Ala Tyr Pro Leu Ala
    530                 535                 540
Val Val Val Pro Ser Gly Asp Ala Leu Ser Arg His Gly Ile Glu Asn
545                 550                 555                 560
Leu Lys Pro Val Ile Ser Glu Ser Leu Gln Glu Val Ala Arg Ala Ala
                565                 570                 575
Gly Leu Gln Ser Tyr Glu Ile Pro Arg Asp Phe Ile Ile Glu Thr Thr
            580                 585                 590
Pro Phe Thr Leu Glu Asn Gly Leu Leu Thr Gly Ile Arg Lys Leu Ala
        595                 600                 605
```

```
Arg Pro Gln Leu Lys Lys Phe Tyr Gly Glu Arg Leu Glu Arg Leu Tyr
    610                 615                 620

Thr Glu Leu Ala Asp Ser Gln Ser Asn Glu Leu Arg Glu Leu Arg Gln
625                 630                 635                 640

Ser Gly Pro Asp Ala Pro Val Leu Pro Thr Leu Cys Arg Ala Ala Ala
                645                 650                 655

Ala Leu Leu Gly Ser Thr Ala Ala Asp Val Arg Pro Asp Ala His Phe
            660                 665                 670

Ala Asp Leu Gly Gly Asp Ser Leu Ser Ala Leu Ser Leu Ala Asn Leu
        675                 680                 685

Leu His Glu Ile Phe Gly Val Asp Val Pro Val Gly Val Ile Val Ser
    690                 695                 700

Pro Ala Ser Asp Leu Arg Ala Leu Ala Asp His Ile Glu Ala Ala Arg
705                 710                 715                 720

Thr Gly Val Arg Arg Pro Ser Phe Ala Ser Ile His Gly Arg Ser Ala
                725                 730                 735

Thr Glu Val His Ala Ser Asp Leu Thr Leu Asp Lys Phe Ile Asp Ala
            740                 745                 750

Ala Thr Leu Ala Ala Ala Pro Asn Leu Pro Ala Pro Ser Ala Gln Val
        755                 760                 765

Arg Thr Val Leu Leu Thr Gly Ala Thr Gly Phe Leu Gly Arg Tyr Leu
    770                 775                 780

Ala Leu Glu Trp Leu Asp Arg Met Asp Leu Val Asn Gly Lys Leu Ile
785                 790                 795                 800

Cys Leu Val Arg Ala Arg Ser Asp Glu Glu Ala Gln Ala Arg Leu Asp
                805                 810                 815

Ala Thr Phe Asp Ser Gly Asp Pro Tyr Leu Val Arg His Tyr Arg Glu
            820                 825                 830

Leu Gly Ala Gly Arg Leu Glu Val Leu Ala Gly Asp Lys Gly Glu Ala
        835                 840                 845

Asp Leu Gly Leu Asp Arg Val Thr Trp Gln Arg Leu Ala Asp Thr Val
    850                 855                 860

Asp Leu Ile Val Asp Pro Ala Ala Leu Val Asn His Val Leu Pro Tyr
865                 870                 875                 880

Ser Gln Leu Phe Gly Pro Asn Ala Ala Gly Thr Ala Glu Leu Leu Arg
                885                 890                 895

Leu Ala Leu Thr Gly Lys Arg Lys Pro Tyr Ile Tyr Thr Ser Thr Ile
            900                 905                 910

Ala Val Gly Glu Gln Ile Pro Pro Glu Ala Phe Thr Glu Asp Ala Asp
        915                 920                 925

Ile Arg Ala Ile Ser Pro Thr Arg Arg Ile Asp Asp Ser Tyr Ala Asn
    930                 935                 940

Gly Tyr Ala Asn Ser Lys Trp Ala Gly Glu Val Leu Leu Arg Glu Ala
945                 950                 955                 960

His Glu Gln Cys Gly Leu Pro Val Thr Val Phe Arg Cys Asp Met Ile
                965                 970                 975

Leu Ala Asp Thr Ser Tyr Thr Gly Gln Leu Asn Leu Pro Asp Met Phe
            980                 985                 990

Thr Arg Leu Met Leu Ser Leu Ala Ala Thr Gly Ile Ala Pro Gly Ser
        995                 1000                1005

Phe Tyr Glu Leu Asp Ala His Gly Asn Arg Gln Arg Ala His Tyr
    1010                1015                1020

Asp Gly Leu Pro Val Glu Phe Val Ala Glu Ala Ile Cys Thr Leu
```

-continued 1025 1030 1035

Gly Thr His Ser Pro Asp Arg Phe Val Thr Tyr His Val Met Asn
1040 1045 1050

Pro Tyr Asp Asp Gly Ile Gly Leu Asp Glu Phe Val Asp Trp Leu
1055 1060 1065

Asn Ser Pro Thr Ser Gly Ser Gly Cys Thr Ile Gln Arg Ile Ala
1070 1075 1080

Asp Tyr Gly Glu Trp Leu Gln Arg Phe Glu Thr Ser Leu Arg Ala
1085 1090 1095

Leu Pro Asp Arg Gln Arg His Ala Ser Leu Leu Pro Leu Leu His
1100 1105 1110

Asn Tyr Arg Glu Pro Ala Lys Pro Ile Cys Gly Ser Ile Ala Pro
1115 1120 1125

Thr Asp Gln Phe Arg Ala Ala Val Gln Glu Ala Lys Ile Gly Pro
1130 1135 1140

Asp Lys Asp Ile Pro His Leu Thr Ala Ala Ile Ile Ala Lys Tyr
1145 1150 1155

Ile Ser Asn Leu Arg Leu Leu Gly Leu Leu
1160 1165

<210> SEQ ID NO 33
<211> LENGTH: 1047
<212> TYPE: PRT
<213> ORGANISM: M. bovis BCG

<400> SEQUENCE: 33

Met Ser Ile Asn Asp Gln Arg Leu Thr Arg Arg Val Glu Asp Leu Tyr
1 5 10 15

Ala Ser Asp Ala Gln Phe Ala Ala Ala Ser Pro Asn Glu Ala Ile Thr
20 25 30

Gln Ala Ile Asp Gln Pro Gly Val Ala Leu Pro Gln Leu Ile Arg Met
35 40 45

Val Met Glu Gly Tyr Ala Asp Arg Pro Ala Leu Gly Gln Arg Ala Leu
50 55 60

Arg Phe Val Thr Asp Pro Asp Ser Gly Arg Thr Met Val Glu Leu Leu
65 70 75 80

Pro Arg Phe Glu Thr Ile Thr Tyr Arg Glu Leu Trp Ala Arg Ala Gly
85 90 95

Thr Leu Ala Thr Ala Leu Ser Ala Glu Pro Ala Ile Arg Pro Gly Asp
100 105 110

Arg Val Cys Val Leu Gly Phe Asn Ser Val Asp Tyr Thr Thr Ile Asp
115 120 125

Ile Ala Leu Ile Arg Leu Gly Ala Val Ser Val Pro Leu Gln Thr Ser
130 135 140

Ala Pro Val Thr Gly Leu Arg Pro Ile Val Thr Glu Thr Glu Pro Thr
145 150 155 160

Met Ile Ala Thr Ser Ile Asp Asn Leu Gly Asp Ala Val Glu Val Leu
165 170 175

Ala Gly His Ala Pro Ala Arg Leu Val Val Phe Asp Tyr His Gly Lys
180 185 190

Val Asp Thr His Arg Glu Ala Val Glu Ala Ala Arg Ala Arg Leu Ala
195 200 205

Gly Ser Val Thr Ile Asp Thr Leu Ala Glu Leu Ile Glu Arg Gly Arg
210 215 220

-continued

```
Ala Leu Pro Ala Thr Pro Ile Ala Asp Ser Ala Asp Ala Leu Ala
225                 230                 235                 240

Leu Leu Ile Tyr Thr Ser Gly Ser Thr Gly Ala Pro Lys Gly Ala Met
            245                 250                 255

Tyr Arg Glu Ser Gln Val Met Ser Phe Trp Arg Lys Ser Gly Trp
        260                 265                 270

Phe Glu Pro Ser Gly Tyr Pro Ser Ile Thr Leu Asn Phe Met Pro Met
        275                 280                 285

Ser His Val Gly Gly Arg Gln Val Leu Tyr Gly Thr Leu Ser Asn Gly
        290                 295                 300

Gly Thr Ala Tyr Tyr Val Ala Lys Ser Asp Leu Ser Thr Leu Phe Glu
305                 310                 315                 320

Asp Leu Ala Leu Val Arg Pro Thr Glu Leu Cys Phe Val Pro Arg Ile
                325                 330                 335

Trp Asp Met Val Phe Ala Glu Phe His Ser Glu Val Asp Arg Arg Leu
                340                 345                 350

Val Asp Gly Ala Asp Arg Ala Ala Leu Glu Ala Gln Val Lys Ala Glu
            355                 360                 365

Leu Arg Glu Asn Val Leu Gly Gly Arg Phe Val Met Ala Leu Thr Gly
        370                 375                 380

Ser Ala Pro Ile Ser Ala Glu Met Thr Ala Trp Val Glu Ser Leu Leu
385                 390                 395                 400

Ala Asp Val His Leu Val Glu Gly Tyr Gly Ser Thr Glu Ala Gly Met
                405                 410                 415

Val Leu Asn Asp Gly Met Val Arg Arg Pro Ala Val Ile Asp Tyr Lys
                420                 425                 430

Leu Val Asp Val Pro Glu Leu Gly Tyr Phe Gly Thr Asp Gln Pro Tyr
            435                 440                 445

Pro Arg Gly Glu Leu Leu Val Lys Thr Gln Thr Met Phe Pro Gly Tyr
        450                 455                 460

Tyr Gln Arg Pro Asp Val Thr Ala Glu Val Phe Asp Pro Asp Gly Phe
465                 470                 475                 480

Tyr Arg Thr Gly Asp Ile Met Ala Lys Val Gly Pro Asp Gln Phe Val
                485                 490                 495

Tyr Leu Asp Arg Arg Asn Asn Val Leu Lys Leu Ser Gln Gly Glu Phe
            500                 505                 510

Ile Ala Val Ser Lys Leu Glu Ala Val Phe Gly Asp Ser Pro Leu Val
        515                 520                 525

Arg Gln Ile Phe Ile Tyr Gly Asn Ser Ala Arg Ala Tyr Pro Leu Ala
530                 535                 540

Val Val Val Pro Ser Gly Asp Ala Leu Ser Arg His Gly Ile Glu Asn
545                 550                 555                 560

Leu Lys Pro Val Ile Ser Glu Ser Leu Gln Glu Val Ala Arg Ala Ala
            565                 570                 575

Gly Leu Gln Ser Tyr Glu Ile Pro Arg Asp Phe Ile Ile Glu Thr Thr
        580                 585                 590

Pro Phe Thr Leu Glu Asn Gly Leu Thr Gly Ile Arg Lys Leu Ala
        595                 600                 605

Arg Pro Gln Leu Lys Lys Phe Tyr Gly Glu Arg Leu Glu Arg Leu Tyr
        610                 615                 620

Thr Glu Leu Ala Asp Ser Gln Ser Asn Glu Leu Arg Glu Leu Arg Gln
625                 630                 635                 640

Ser Gly Pro Asp Ala Pro Val Leu Pro Thr Leu Cys Arg Ala Ala Ala
```

```
                    645                 650                 655
Ala Leu Leu Gly Ser Thr Ala Ala Asp Val Arg Pro Asp Ala His Phe
                660                 665                 670
Ala Asp Leu Gly Gly Asp Ser Leu Ser Ala Leu Ser Leu Ala Asn Leu
            675                 680                 685
Leu His Glu Ile Phe Gly Val Asp Val Pro Val Gly Val Ile Val Ser
        690                 695                 700
Pro Ala Ser Asp Leu Arg Ala Leu Ala Asp His Ile Glu Ala Ala Arg
705                 710                 715                 720
Thr Gly Val Arg Arg Pro Ser Phe Ala Ser Ile His Gly Arg Ser Ala
                725                 730                 735
Thr Glu Val His Ala Ser Asp Leu Thr Leu Asp Lys Phe Ile Asp Ala
                740                 745                 750
Ala Thr Leu Ala Ala Ala Pro Asn Leu Pro Ala Pro Ser Ala Gln Val
            755                 760                 765
Arg Thr Val Leu Leu Thr Gly Ala Thr Gly Phe Leu Gly Arg Tyr Leu
        770                 775                 780
Ala Leu Glu Trp Leu Asp Arg Met Asp Leu Val Asn Gly Lys Leu Ile
785                 790                 795                 800
Cys Leu Val Arg Ala Arg Ser Asp Glu Glu Ala Gln Ala Arg Leu Asp
                805                 810                 815
Ala Thr Phe Asp Ser Gly Asp Pro Tyr Leu Val Arg His Tyr Arg Glu
                820                 825                 830
Leu Gly Ala Gly Arg Leu Glu Val Leu Ala Gly Asp Lys Gly Glu Ala
            835                 840                 845
Asp Leu Gly Leu Asp Arg Val Thr Trp Gln Arg Leu Ala Asp Thr Val
        850                 855                 860
Asp Leu Ile Val Asp Pro Ala Ala Leu Val Asn His Val Leu Pro Tyr
865                 870                 875                 880
Ser Gln Leu Phe Gly Pro Asn Ala Ala Gly Thr Ala Glu Leu Leu Arg
                885                 890                 895
Leu Ala Leu Thr Gly Lys Arg Lys Pro Tyr Ile Tyr Thr Ser Thr Ile
                900                 905                 910
Ala Val Gly Glu Gln Ile Pro Pro Glu Ala Phe Thr Glu Asp Ala Asp
            915                 920                 925
Ile Arg Ala Ile Ser Pro Thr Arg Arg Ile Asp Asp Ser Tyr Ala Asn
        930                 935                 940
Gly Tyr Ala Asn Ser Lys Trp Ala Gly Glu Val Leu Leu Arg Glu Ala
945                 950                 955                 960
His Glu Gln Cys Gly Leu Pro Val Thr Val Phe Arg Cys Asp Met Ile
                965                 970                 975
Leu Ala Asp Thr Ser Tyr Thr Gly Gln Leu Asn Leu Pro Asp Met Phe
            980                 985                 990
Thr Arg Leu Met Leu Ser Leu Ala  Ala Thr Gly Ile Ala  Pro Gly Ser
        995                 1000                1005
Phe Tyr  Glu Leu Asp Ala His  Gly Asn Arg Gln Arg  Ala His Tyr
    1010                1015                1020
Asp Gly  Leu Pro Val Glu Phe  Val Ala Glu Ala Ile  Cys Thr Leu
    1025                1030                1035
Gly Thr  His Ser Pro Asp Arg  Phe Val
    1040                1045

<210> SEQ ID NO 34
```

```
<211> LENGTH: 1174
<212> TYPE: PRT
<213> ORGANISM: M. leprae

<400> SEQUENCE: 34

Met Ser Thr Ile Thr Lys Gln Glu Lys Gln Leu Ala Arg Arg Val Asp
1               5                   10                  15

Asp Leu Thr Ala Asn Asp Pro Gln Phe Ala Ala Lys Pro Asp Pro
            20                  25                  30

Ala Val Ala Ala Ala Leu Ala Gln Pro Gly Leu Arg Leu Pro Gln Ile
        35                  40                  45

Ile Gln Thr Ala Leu Asp Gly Tyr Ala Glu Arg Pro Ala Leu Gly Gln
    50                  55                  60

Arg Val Ala Glu Phe Thr Lys Asp Pro Lys Thr Gly Arg Thr Ser Met
65                  70                  75                  80

Glu Leu Leu Pro Ser Phe Glu Thr Ile Thr Tyr Arg Gln Leu Gly Asp
                85                  90                  95

Arg Val Gly Ala Leu Ala Arg Ala Trp Arg His Asp Leu Leu His Ala
            100                 105                 110

Gly Tyr Arg Val Cys Val Leu Gly Phe Asn Ser Val Asp Tyr Ala Ile
        115                 120                 125

Ile Asp Met Ala Leu Gly Val Ile Gly Ala Val Ala Val Pro Leu Gln
130                 135                 140

Thr Ser Ala Ala Ile Thr Gln Leu Gln Ser Ile Val Thr Glu Thr Glu
145                 150                 155                 160

Pro Ser Met Ile Ala Thr Ser Val Asn Gln Leu Pro Asp Thr Val Glu
                165                 170                 175

Leu Ile Leu Ser Gly Gln Ala Pro Ala Lys Leu Val Val Phe Asp Tyr
            180                 185                 190

His Pro Glu Val Asp Glu Gln His Asp Ala Val Ala Thr Ala Arg Ala
        195                 200                 205

Arg Leu Ala Asp Ser Ser Val Val Glu Ser Leu Thr Glu Val Leu
    210                 215                 220

Gly Arg Gly Lys Thr Leu Pro Ala Thr Pro Ile Pro Val Ala Asp Asp
225                 230                 235                 240

Ser Ala Asp Pro Leu Ala Leu Leu Ile Tyr Thr Ser Gly Ser Thr Gly
                245                 250                 255

Ala Pro Lys Gly Ala Met Tyr Leu Gln Ser Asn Val Gly Lys Met Trp
            260                 265                 270

Arg Arg Ser Asp Gly Asn Trp Phe Gly Pro Thr Ala Ala Ser Ile Thr
        275                 280                 285

Leu Asn Phe Met Pro Met Ser His Val Met Gly Arg Gly Ile Leu Tyr
    290                 295                 300

Gly Thr Leu Gly Asn Gly Gly Thr Ala Tyr Phe Ala Ala Arg Ser Asp
305                 310                 315                 320

Leu Ser Thr Leu Leu Glu Asp Leu Lys Leu Val Arg Pro Thr Glu Leu
                325                 330                 335

Asn Phe Val Pro Arg Ile Trp Glu Thr Leu Tyr Asp Glu Ser Lys Arg
            340                 345                 350

Ala Val Asp Arg Arg Leu Ala Asn Ser Gly Ser Ala Asp Arg Ala Ala
        355                 360                 365

Ile Lys Ala Glu Val Met Asp Glu Gln Arg Gln Ser Leu Leu Gly Gly
    370                 375                 380

Arg Tyr Ile Ala Ala Met Thr Gly Ser Ala Pro Thr Ser Pro Glu Leu
```

-continued

```
            385                 390                 395                 400
Lys His Gly Val Glu Ser Leu Leu Glu Met His Leu Leu Glu Gly Tyr
                    405                 410                 415
Gly Ser Thr Glu Ala Gly Met Val Leu Phe Asp Gly Glu Val Gln Arg
                    420                 425                 430
Pro Pro Val Ile Asp Tyr Lys Leu Val Asp Val Pro Asp Leu Gly Tyr
                    435                 440                 445
Phe Ser Thr Asp Gln Pro Tyr Pro Arg Gly Glu Leu Leu Leu Lys Thr
        450                 455                 460
Gln Asn Met Phe Pro Gly Tyr Tyr Lys Arg Pro Glu Val Thr Ala Thr
465                 470                 475                 480
Val Phe Asp Ser Asp Gly Tyr Tyr Gln Thr Gly Asp Ile Val Ala Glu
                    485                 490                 495
Val Gly Pro Asp Arg Leu Val Tyr Val Asp Arg Arg Asn Asn Val Leu
                    500                 505                 510
Lys Leu Ala Gln Gly Gln Phe Val Thr Val Ala Lys Leu Glu Ala Ala
                    515                 520                 525
Phe Ser Asn Ser Pro Leu Val Arg Gln Ile Tyr Ile Tyr Gly Asn Ser
        530                 535                 540
Ala His Pro Tyr Leu Leu Ala Val Val Pro Thr Glu Asp Ala Leu
545                 550                 555                 560
Ala Thr Asn Asp Ile Glu Val Leu Lys Pro Leu Ile Ile Asp Ser Leu
                    565                 570                 575
Gln Lys Val Ala Lys Glu Ala Asp Leu Gln Ser Tyr Glu Val Pro Arg
                    580                 585                 590
Asp Leu Ile Val Glu Thr Thr Pro Phe Ser Leu Glu Asn Gly Leu Leu
                    595                 600                 605
Thr Gly Ile Arg Lys Leu Ala Trp Pro Lys Leu Lys Gln His Tyr Gly
                    610                 615                 620
Ala Arg Leu Glu Gln Leu Tyr Ala Asp Leu Val Glu Gly Gln Ala Asn
625                 630                 635                 640
Ala Leu His Val Leu Lys Gln Ser Val Ala Asn Ala Pro Val Leu Gln
                    645                 650                 655
Thr Val Ser Arg Ala Val Gly Thr Ile Leu Gly Val Ala Thr Thr Asp
                    660                 665                 670
Leu Pro Ser Asn Ala His Phe Thr Asp Leu Gly Gly Asp Ser Leu Ser
                    675                 680                 685
Ala Leu Thr Phe Gly Ser Leu Leu Arg Glu Leu Phe Asp Ile Asp Val
                    690                 695                 700
Pro Val Gly Val Ile Val Ser Pro Val Asn Asn Leu Val Ala Ile Ala
705                 710                 715                 720
Asp Tyr Ile Glu Arg Glu Arg Gln Gly Thr Lys Arg Pro Thr Phe Ile
                    725                 730                 735
Ala Ile His Gly Arg Asp Ala Gly Lys Val His Ala Ser Asp Leu Thr
                    740                 745                 750
Leu Asp Lys Phe Ile Asp Val Ser Thr Leu Thr Ala Ala Pro Val Leu
                    755                 760                 765
Ala Gln Pro Gly Thr Glu Val Arg Thr Val Leu Leu Thr Gly Ala Thr
                    770                 775                 780
Gly Phe Leu Gly Arg Tyr Leu Ala Leu Lys Trp Leu Glu Arg Met Asp
785                 790                 795                 800
Leu Val Glu Gly Lys Val Ile Ala Leu Val Arg Ala Lys Ser Asn Glu
                    805                 810                 815
```

Asp Ala Arg Ala Arg Leu Asp Lys Thr Phe Asp Ser Gly Asp Pro Lys
           820                 825                 830

Leu Leu Ala His Tyr Gln Glu Leu Ala Thr Asp His Leu Glu Val Ile
           835                 840                 845

Ala Gly Asp Lys Gly Glu Val Asp Leu Glu Leu Asp Arg Gln Thr Trp
           850                 855                 860

Arg Arg Leu Ala Asp Thr Val Asp Leu Ile Val Asp Pro Ala Ala Leu
865                 870                 875                 880

Val Asn His Val Leu Pro Tyr Ser Glu Leu Phe Gly Pro Asn Thr Leu
                885                 890                 895

Gly Thr Ala Glu Leu Ile Arg Ile Ala Leu Thr Ser Lys Gln Lys Pro
            900                 905                 910

Tyr Ile Tyr Val Ser Thr Ile Gly Val Gly Asn Gln Ile Glu Pro Ala
            915                 920                 925

Lys Phe Thr Glu Asp Ser Asp Ile Arg Val Ile Ser Pro Thr Arg Asn
            930                 935                 940

Ile Asn Asn Asn Tyr Ala Asn Gly Tyr Gly Asn Ser Lys Trp Ala Gly
945                 950                 955                 960

Glu Val Leu Leu Arg Glu Ala His Asp Leu Cys Gly Leu Pro Val Thr
                965                 970                 975

Val Phe Arg Cys Asp Met Ile Leu Ala Asp Thr Ser Tyr Ala Gly Gln
            980                 985                 990

Leu Asn Val Pro Asp Met Phe Thr Arg Met Met Leu Ser Leu Ala Ala
            995                 1000                1005

Thr Gly Ile Ala Pro Gly Ser Phe Tyr Glu Leu Asp Ala Glu Ser
            1010            1015            1020

Asn Arg Gln Arg Ala His Tyr Asp Gly Leu Pro Val Glu Phe Ile
            1025            1030            1035

Ala Glu Ala Ile Ser Thr Leu Gly Asp Gln Ser Leu His Asp Arg
            1040            1045            1050

Asp Gly Phe Thr Thr Tyr His Val Met Asn Pro His Asp Asp Gly
            1055            1060            1065

Ile Gly Met Asp Glu Phe Val Asp Trp Leu Ile Asp Ala Gly Cys
            1070            1075            1080

Pro Ile Gln Arg Ile Asn Asp Tyr Asp Glu Trp Leu Arg Arg Phe
            1085            1090            1095

Glu Ile Ser Leu Arg Ala Leu Pro Glu Arg Gln Arg His Ser Ser
            1100            1105            1110

Leu Leu Pro Leu Leu His Asn Tyr Gln Lys Pro Glu Lys Pro Leu
            1115            1120            1125

His Gly Ser Leu Ala Pro Thr Ile Arg Phe Arg Thr Ala Val Gln
            1130            1135            1140

Asn Ala Asn Ile Gly Gln Asp Lys Asp Ile Pro His Ile Ser Pro
            1145            1150            1155

Ala Ile Ile Ala Lys Tyr Val Ser Asp Leu Gln Leu Leu Gly Leu
            1160            1165            1170

Val

<210> SEQ ID NO 35
<211> LENGTH: 1168
<212> TYPE: PRT
<213> ORGANISM: M. smegmatis MBCG

<400> SEQUENCE: 35

```
Met Thr Ile Glu Thr Arg Glu Asp Arg Phe Asn Arg Arg Ile Asp His
1               5                   10                  15

Leu Phe Glu Thr Asp Pro Gln Phe Ala Ala Arg Pro Asp Glu Ala
            20                  25                  30

Ile Ser Ala Ala Ala Asp Pro Glu Leu Arg Leu Pro Ala Ala Val
        35                  40                  45

Lys Gln Ile Leu Ala Gly Tyr Ala Asp Arg Pro Ala Leu Gly Lys Arg
50                      55                  60

Ala Val Glu Phe Val Thr Asp Glu Gly Arg Thr Thr Ala Lys Leu
65                  70                  75              80

Leu Pro Arg Phe Asp Thr Ile Thr Tyr Arg Gln Leu Ala Gly Arg Ile
                85                  90                  95

Gln Ala Val Thr Asn Ala Trp His Asn His Pro Val Asn Ala Gly Asp
                100                 105                 110

Arg Val Ala Ile Leu Gly Phe Thr Ser Val Asp Tyr Thr Thr Ile Asp
            115                 120                 125

Ile Ala Leu Leu Glu Leu Gly Ala Val Ser Val Pro Leu Gln Thr Ser
130                 135                 140

Ala Pro Val Ala Gln Leu Gln Pro Ile Val Ala Glu Thr Glu Pro Lys
145                 150                 155                 160

Val Ile Ala Ser Ser Val Asp Phe Leu Ala Asp Ala Val Ala Leu Val
            165                 170                 175

Glu Ser Gly Pro Ala Pro Ser Arg Leu Val Val Phe Asp Tyr Ser His
            180                 185                 190

Glu Val Asp Asp Gln Arg Glu Ala Phe Glu Ala Ala Lys Gly Lys Leu
            195                 200                 205

Ala Gly Thr Gly Val Val Glu Thr Ile Thr Asp Ala Leu Asp Arg
210                 215                 220

Gly Arg Ser Leu Ala Asp Ala Pro Leu Tyr Val Pro Asp Glu Ala Asp
225                 230                 235                 240

Pro Leu Thr Leu Leu Ile Tyr Thr Ser Gly Ser Thr Gly Thr Pro Lys
                245                 250                 255

Gly Ala Met Tyr Pro Glu Ser Lys Thr Ala Thr Met Trp Gln Ala Gly
            260                 265                 270

Ser Lys Ala Arg Trp Asp Glu Thr Leu Gly Val Met Pro Ser Ile Thr
275                 280                 285

Leu Asn Phe Met Pro Met Ser His Val Met Gly Arg Gly Ile Leu Cys
    290                 295                 300

Ser Thr Leu Ala Ser Gly Gly Thr Ala Tyr Phe Ala Ala Arg Ser Asp
305                 310                 315                 320

Leu Ser Thr Phe Leu Glu Asp Leu Ala Leu Val Arg Pro Thr Gln Leu
            325                 330                 335

Asn Phe Val Pro Arg Ile Trp Asp Met Leu Phe Gln Glu Tyr Gln Ser
            340                 345                 350

Arg Leu Asp Asn Arg Arg Ala Glu Gly Ser Glu Asp Arg Ala Glu Ala
        355                 360                 365

Ala Val Leu Glu Glu Val Arg Thr Gln Leu Leu Gly Gly Arg Phe Val
        370                 375                 380

Ser Ala Leu Thr Gly Ser Ala Pro Ile Ser Ala Glu Met Lys Ser Trp
385                 390                 395                 400

Val Glu Asp Leu Leu Asp Met His Leu Leu Glu Gly Tyr Gly Ser Thr
            405                 410                 415
```

-continued

```
Glu Ala Gly Ala Val Phe Ile Asp Gly Gln Ile Gln Arg Pro Pro Val
            420                 425                 430

Ile Asp Tyr Lys Leu Val Asp Val Pro Asp Leu Gly Tyr Phe Ala Thr
            435                 440                 445

Asp Arg Pro Tyr Pro Arg Gly Glu Leu Leu Val Lys Ser Glu Gln Met
450                 455                 460

Phe Pro Gly Tyr Tyr Lys Arg Pro Glu Ile Thr Ala Glu Met Phe Asp
465                 470                 475                 480

Glu Asp Gly Tyr Tyr Arg Thr Gly Asp Ile Val Ala Glu Leu Gly Pro
                485                 490                 495

Asp His Leu Glu Tyr Leu Asp Arg Arg Asn Asn Val Leu Lys Leu Ser
                500                 505                 510

Gln Gly Glu Phe Val Thr Val Ser Lys Leu Glu Ala Val Phe Gly Asp
            515                 520                 525

Ser Pro Leu Val Arg Gln Ile Tyr Val Tyr Gly Asn Ser Ala Arg Ser
530                 535                 540

Tyr Leu Leu Ala Val Val Val Pro Thr Glu Glu Ala Leu Ser Arg Trp
545                 550                 555                 560

Asp Gly Asp Glu Leu Lys Ser Arg Ile Ser Ser Leu Gln Asp Ala
                565                 570                 575

Ala Arg Ala Ala Gly Leu Gln Ser Tyr Glu Ile Pro Arg Asp Phe Leu
            580                 585                 590

Val Glu Thr Thr Pro Phe Thr Leu Glu Asn Gly Leu Leu Thr Gly Ile
                595                 600                 605

Arg Lys Leu Ala Arg Pro Lys Leu Lys Ala His Tyr Gly Glu Arg Leu
610                 615                 620

Glu Gln Leu Tyr Thr Asp Leu Ala Glu Gly Gln Ala Asn Glu Leu Arg
625                 630                 635                 640

Glu Leu Arg Arg Asn Gly Ala Asp Arg Pro Val Val Glu Thr Val Ser
                645                 650                 655

Arg Ala Ala Val Ala Leu Leu Gly Ala Ser Val Thr Asp Leu Arg Ser
            660                 665                 670

Asp Ala His Phe Thr Asp Leu Gly Gly Asp Ser Leu Ser Ala Leu Ser
            675                 680                 685

Phe Ser Asn Leu Leu His Glu Ile Phe Asp Val Asp Val Pro Val Gly
690                 695                 700

Val Ile Val Ser Pro Ala Thr Asp Leu Ala Gly Val Ala Ala Tyr Ile
705                 710                 715                 720

Glu Gly Glu Leu Arg Gly Ser Lys Arg Pro Thr Tyr Ala Ser Val His
                725                 730                 735

Gly Arg Asp Ala Thr Glu Val Arg Ala Arg Asp Leu Ala Leu Gly Lys
            740                 745                 750

Phe Ile Asp Ala Lys Thr Leu Ser Ala Pro Gly Leu Pro Arg Ser
            755                 760                 765

Gly Thr Glu Ile Arg Thr Val Leu Leu Thr Gly Ala Thr Gly Phe Leu
770                 775                 780

Gly Arg Tyr Leu Ala Leu Glu Trp Leu Glu Arg Met Asp Leu Val Asp
785                 790                 795                 800

Gly Lys Val Ile Cys Leu Val Arg Ala Arg Ser Asp Asp Glu Ala Arg
                805                 810                 815

Ala Arg Leu Asp Ala Thr Phe Asp Thr Gly Asp Ala Thr Leu Leu Glu
            820                 825                 830

His Tyr Arg Ala Leu Ala Ala Asp His Leu Glu Val Ile Ala Gly Asp
```

```
            835                 840                 845
Lys Gly Glu Ala Asp Leu Gly Leu Asp His Asp Thr Trp Gln Arg Leu
    850                 855                 860

Ala Asp Thr Val Asp Leu Ile Val Asp Pro Ala Ala Leu Val Asn His
865                 870                 875                 880

Val Leu Pro Tyr Ser Gln Met Phe Gly Pro Asn Ala Leu Gly Thr Ala
                885                 890                 895

Glu Leu Ile Arg Ile Ala Leu Thr Thr Thr Ile Lys Pro Tyr Val Tyr
            900                 905                 910

Val Ser Thr Ile Gly Val Gly Gln Gly Ile Ser Pro Glu Ala Phe Val
            915                 920                 925

Glu Asp Ala Asp Ile Arg Glu Ile Ser Ala Thr Arg Arg Val Asp Asp
930                 935                 940

Ser Tyr Ala Asn Gly Tyr Gly Asn Ser Lys Trp Ala Gly Glu Val Leu
945                 950                 955                 960

Leu Arg Glu Ala His Asp Trp Cys Gly Leu Pro Val Ser Val Phe Arg
                965                 970                 975

Cys Asp Met Ile Leu Ala Asp Thr Thr Tyr Ser Gly Gln Leu Asn Leu
            980                 985                 990

Pro Asp Met Phe Thr Arg Leu Met Leu Ser Leu Val Ala Thr Gly Ile
            995                 1000                1005

Ala Pro Gly Ser Phe Tyr Glu Leu Asp Ala Asp Gly Asn Arg Gln
    1010                1015                1020

Arg Ala His Tyr Asp Gly Leu Pro Val Glu Phe Ile Ala Glu Ala
    1025                1030                1035

Ile Ser Thr Ile Gly Ser Gln Val Thr Asp Gly Phe Glu Thr Phe
    1040                1045                1050

His Val Met Asn Pro Tyr Asp Asp Gly Ile Gly Leu Asp Glu Tyr
    1055                1060                1065

Val Asp Trp Leu Ile Glu Ala Gly Tyr Pro Val His Arg Val Asp
    1070                1075                1080

Asp Tyr Ala Thr Trp Leu Ser Arg Phe Glu Thr Ala Leu Arg Ala
    1085                1090                1095

Leu Pro Glu Arg Gln Arg Gln Ala Ser Leu Leu Pro Leu Leu His
    1100                1105                1110

Asn Tyr Gln Gln Pro Ser Pro Val Cys Gly Ala Met Ala Pro
    1115                1120                1125

Thr Asp Arg Phe Arg Ala Ala Val Gln Asp Ala Lys Ile Gly Pro
    1130                1135                1140

Asp Lys Asp Ile Pro His Val Thr Ala Asp Val Ile Val Lys Tyr
    1145                1150                1155

Ile Ser Asn Leu Gln Met Leu Gly Leu Leu
    1160                1165

<210> SEQ ID NO 36
<211> LENGTH: 869
<212> TYPE: PRT
<213> ORGANISM: hypothetical

<400> SEQUENCE: 36

Val Asp Arg Leu Arg Arg Ile Glu Leu Phe Ala Asp Gln Phe Ala Ala
1               5                   10                  15

Ala Pro Glu Ala Val Ser Ala Val Pro Gly Met Leu Pro Gln Ile Ile
            20                  25                  30
```

-continued

```
Val Met Gly Tyr Ala Asp Arg Pro Ala Leu Gly Gln Arg Ala Phe Thr
    35                  40                  45

Asp Thr Gly Arg Leu Leu Gly Phe Ser Val Asp Tyr Thr Ile Asp Leu
        50                  55                  60

Ala Leu Ile Leu Gly Ala Val Thr Val Pro Leu Gln Thr Ser Ala Val
 65                 70                  75                  80

Ser Leu Ile Val Thr Glu Thr Glu Pro Leu Ile Ala Ser Ser Ile Glu
                85                  90                  95

Leu Asp Ala Val Glu Val Leu Ala Pro Arg Leu Val Val Phe Asp Tyr
            100                 105                 110

His Val Asp Arg Glu Ala Glu Ala Arg Ala Arg Leu Ala Ser Val Val
            115                 120                 125

Glu Thr Leu Glu Val Ile Arg Gly Arg Leu Pro Ala Val Asp Asp Leu
        130                 135                 140

Ala Leu Leu Ile Tyr Thr Ser Gly Ser Thr Gly Pro Lys Gly Ala Met
145                 150                 155                 160

Tyr Ser Thr Trp Ser Ile Thr Leu Asn Phe Met Pro Met Ser His Val
                165                 170                 175

Gly Arg Val Leu Phe Gly Thr Leu Gly Gly Thr Ala Tyr Phe Ala Lys
            180                 185                 190

Ser Asp Leu Ser Thr Leu Glu Asp Leu Gly Leu Val Arg Pro Thr Glu
            195                 200                 205

Leu Phe Val Pro Arg Ile Trp Asp Met Val Phe Glu Tyr Ser Leu Asp
        210                 215                 220

Arg Arg Gly Ala Asp Leu Asp Ala Val Glu Leu Arg Asn Val Leu Gly
225                 230                 235                 240

Gly Arg Phe Leu Ala Val Thr Gly Ser Ala Pro Leu Ser Ala Glu Met
                245                 250                 255

Phe Val Glu Ser Leu Asp Leu His Leu Val Glu Gly Tyr Gly Ser Thr
            260                 265                 270

Glu Ala Gly Val Leu Asp Gly Ile Arg Pro Val Ile Asp Tyr Lys Leu
        275                 280                 285

Val Asp Val Pro Glu Leu Gly Tyr Phe Thr Asp Pro Tyr Pro Arg Gly
    290                 295                 300

Glu Leu Leu Leu Lys Thr Met Phe Pro Gly Tyr Tyr Arg Pro Glu Val
305                 310                 315                 320

Thr Ala Glu Ile Phe Asp Asp Gly Phe Tyr Lys Thr Gly Asp Ile Val
                325                 330                 335

Ala Leu Gly Pro Asp Val Tyr Val Asp Arg Arg Asn Asn Val Leu Lys
            340                 345                 350

Leu Ser Gln Gly Glu Phe Val Val Lys Leu Glu Ala Val Phe Ala Ser
            355                 360                 365

Pro Leu Val Arg Gln Ile Phe Ile Tyr Gly Asn Ser Ala Arg Tyr Leu
        370                 375                 380

Ala Val Val Val Pro Thr Asp Ala Leu Glu Leu Lys Ile Glu Ser Leu
385                 390                 395                 400

Gln Ile Ala Lys Ala Leu Gln Ser Tyr Glu Ile Pro Arg Asp Phe Leu
                405                 410                 415

Ile Glu Thr Thr Pro Phe Thr Leu Glu Asn Gly Leu Leu Thr Gly Ile
            420                 425                 430

Arg Lys Leu Ala Arg Pro Leu Lys Tyr Gly Arg Leu Glu Leu Tyr Thr
        435                 440                 445

Asp Leu Ala Asp Gln Asn Glu Leu Arg Leu Arg Ala Asp Pro Val Leu
```

-continued

```
            450                 455                 460
Thr Val Arg Ala Ala Met Leu Gly Asp Met Arg Asp Ala His Phe
465                 470                 475                 480

Asp Leu Gly Gly Asp Ser Leu Ser Ala Leu Ser Asn Leu Leu His Glu
                485                 490                 495

Ile Phe Val Asp Val Pro Val Gly Val Ile Val Ser Pro Ala Glu Leu
                500                 505                 510

Ala Leu Ala Ile Glu Ala Arg Gly Lys Arg Pro Thr Phe Ser Val His
            515                 520                 525

Gly Arg Ala Ser Glu Val Arg Ala Asp Leu Thr Leu Asp Lys Phe Ile
530                 535                 540

Asp Ala Thr Leu Ala Ala Pro Leu Pro Val Arg Thr Val Leu Leu Thr
545                 550                 555                 560

Gly Ala Thr Gly Phe Leu Gly Arg Tyr Leu Ala Leu Glu Trp Leu Glu
                565                 570                 575

Arg Met Asp Leu Val Gly Lys Leu Ile Cys Leu Val Arg Ala Arg Ser
                580                 585                 590

Glu Glu Ala Ala Arg Leu Asp Thr Phe Asp Ser Gly Asp Pro Leu Leu
            595                 600                 605

His Tyr Leu Ala Ala Arg Leu Glu Val Leu Ala Gly Asp Lys Gly Glu
            610                 615                 620

Asp Leu Gly Leu Asp Arg Thr Trp Gln Arg Leu Ala Asp Thr Val Asp
625                 630                 635                 640

Leu Ile Val Asp Pro Ala Ala Leu Val Asn His Val Leu Pro Tyr Ser
                645                 650                 655

Gln Leu Phe Gly Pro Asn Gly Thr Ala Glu Leu Val Arg Leu Ala Leu
                660                 665                 670

Thr Arg Lys Pro Tyr Ile Tyr Ser Thr Ile Gly Val Gly Gln Ile Pro
            675                 680                 685

Phe Glu Asp Asp Ile Arg Ile Ser Thr Arg Val Glu Ser Tyr Ala Asn
            690                 695                 700

Gly Tyr Gly Asn Ser Lys Trp Ala Gly Glu Val Leu Leu Arg Glu Ala
705                 710                 715                 720

His Asp Cys Gly Leu Pro Val Thr Val Phe Arg Cys Asp Met Ile Leu
                725                 730                 735

Ala Asp Thr Ser Tyr Gly Gln Leu Asn Val Pro Asp Met Phe Thr Arg
                740                 745                 750

Leu Met Leu Ser Leu Ala Thr Gly Ile Ala Pro Gly Ser Phe Tyr Glu
            755                 760                 765

Leu Asp Ala Gly Asn Arg Gln Arg Ala His Tyr Asp Gly Leu Pro Val
770                 775                 780

Glu Phe Val Ala Glu Ala Ile Thr Leu Gly Asp Phe Thr Tyr Val Leu
785                 790                 795                 800

Asn Pro Asp Asp Gly Ile Leu Asp Glu Phe Val Asp Trp Leu Ile Arg
                805                 810                 815

Ile Asp Tyr Trp Arg Phe Glu Ile Arg Ala Leu Pro Glu Lys Gln Arg
            820                 825                 830

Ser Val Leu Pro Leu Leu Tyr Pro Val Gly Ile Pro Phe Ala Val Gln
            835                 840                 845

Ala Ile Gly Glu Asp Ile Pro His Leu Ser Leu Ile Lys Tyr Val Ser
850                 855                 860

Leu Leu Leu Leu Leu
865
```

<210> SEQ ID NO 37
<211> LENGTH: 4600
<212> TYPE: DNA
<213> ORGANISM: Nocardia

<400> SEQUENCE: 37

| | | | | | |
|---|---|---|---|---|---|
| ggtaccggca | atacctggat | aagcggtcgg | atcctgggcc | gctgcggtgg | agtggccgcc | 60 |
| gttccggccc | gatgtggcca | agaccactcg | agtcaccgcc | gcgtatcacc | ttcccggaag | 120 |
| tatttactta | ggctaacgtg | ttttacgggt | tgcagggctt | ttcctactta | tgacaaggga | 180 |
| ggcttgccat | ggcggtggat | tcaccggatg | agcggctaca | gcgccgcatt | gcgcagttgt | 240 |
| ttgcagaaga | tgagcaggtc | aaggccgcac | gtccgctcga | agcggtgagc | gcggcggtga | 300 |
| gcgcgcccgg | tatgcggctg | gcgcagatcg | ccgccactgt | tatggcgggt | tacgccgacc | 360 |
| gcccggccgc | cgggcagcgt | gcgttcgaac | tgaacaccga | cgacgcgacg | ggccgcacct | 420 |
| cgctgcggtt | acttccccga | ttcgagacca | tcacctatcg | cgaactgtgg | cagcgagtcg | 480 |
| gcgaggttgc | cgcggcctgg | catcatgatc | ccgagaaccc | cttgcgcgca | ggtgattttcg | 540 |
| tcgccctgct | cggcttcacc | agcatcgact | acgccaccct | cgacctggcc | gatatccacc | 600 |
| tcggcgcggt | taccgtgccg | ttgcaggcca | gcgcggcggt | gtcccagctg | atcgctatcc | 660 |
| tcaccgagac | ttcgccgcgg | ctgctcgcct | cgaccccgga | gcacctcgat | gcggcggtcg | 720 |
| agtgcctact | cgcgggcacc | acaccggaac | gactggtggt | cttcgactac | cacccccgagg | 780 |
| acgacgacca | gcgtgcggcc | ttcgaatccg | cccgccgccg | ccttgccgac | gcgggcagct | 840 |
| cggtgatcgt | cgaaacgctc | gatgccgtgc | gtgcccgggg | ccgcgactta | ccggccgcgc | 900 |
| cactgttcgt | tcccgacacc | gacgacgacc | cgctggccct | gctgatctac | acctccggca | 960 |
| gcaccggaac | gccgaagggc | gcgatgtaca | ccaatcggtt | ggccgccacg | atgtggcagg | 1020 |
| ggaactcgat | gctgcagggg | aactcgcaac | gggtcggat | caatctcaac | tacatgccga | 1080 |
| tgagccacat | cgccggtcgc | atatcgctgt | tcggcgtgct | cgctcgcggt | ggcaccgcat | 1140 |
| acttcgcggc | caagagcgac | atgtcgacac | tgttcgaaga | catcggcttg | gtacgtccca | 1200 |
| ccgagatctt | cttcgtcccg | cgcgtgtgcg | acatggtctt | ccagcgctat | cagagcgagc | 1260 |
| tggaccggcg | ctcggtggcg | ggcgccgacc | tggacacgct | cgatcgggaa | gtgaaagccg | 1320 |
| acctccggca | gaactacctc | ggtgggcgct | tcctggtggc | ggtcgtcggc | agcgcgccgc | 1380 |
| tggccgcgga | gatgaagacg | ttcatggagt | ccgtcctcga | tctgccactg | cacgacgggt | 1440 |
| acgggtcgac | cgaggcgggc | gcaagcgtgc | tgctcgacaa | ccagatccag | cggccgccgg | 1500 |
| tgctcgatta | caagctcgtc | gacgtgcccg | aactgggtta | cttccgcacc | gaccggccgc | 1560 |
| atccgcgcgg | tgagctgttg | ttgaaggcgg | agaccacgat | tccgggctac | tacaagcggc | 1620 |
| ccgaggtcac | cgcggagatc | ttcgacgagg | acggcttcta | caagaccggc | gatatcgtgg | 1680 |
| ccgagctcga | gcacgatcgg | ctggtctatg | tcgaccgtcg | caacaatgtg | ctcaaactgt | 1740 |
| cgcagggcga | gttcgtgacc | gtcgcccatc | tcgaggccgt | gttcgccagc | agcccgctga | 1800 |
| tccggcagat | cttcatctac | ggcagcagcg | aacgttccta | tctgctcgcg | gtgatcgtcc | 1860 |
| ccaccgacga | cgcgctgcgc | ggccgcgaca | ccgccacctt | gaaatcggca | ctggccgaat | 1920 |
| cgattcagcg | catcgccaag | gacgcgaacc | tgcagcccta | cgagattccg | cgcgatttcc | 1980 |
| tgatcgagac | cgagccgttc | accatcgcca | acgactgcct | ctccggcatc | gcgaagctgc | 2040 |
| tgcgccccaa | tctgaaggaa | cgctacggcg | ctcagctgga | gcagatgtac | accgatctcg | 2100 |

```
cgacaggcca ggccgatgag ctgctcgccc tgcgccgcga agccgccgac ctgccggtgc    2160
tcgaaaccgt cagccgggca gcgaaagcga tgctcggcgt cgcctccgcc gatatgcgtc    2220
ccgacgcgca cttcaccgac ctgggcggcg attcccttc cgcgctgtcg ttctcgaacc    2280
tgctgcacga gatcttcggg gtcgaggtgc cggtgggtgt cgtcgtcagc ccggcgaacg    2340
agctgcgcga tctggcgaat tacattgagg cggaacgcaa ctcgggcgcg aagcgtccca    2400
ccttcacctc ggtgcacggc ggcggttccg agatccgcgc cgccgatctg accctcgaca    2460
agttcatcga tgcccgcacc ctggccgccg ccgacagcat tccgcacgcg ccggtgccag    2520
cgcagacggt gctgctgacc ggcgcgaacg gctacctcgg ccggttcctg tgcctggaat    2580
ggctggagcg gctggacaag acgggtggca cgctgatctg cgtcgtgcgc ggtagtgacg    2640
cggccgcggc ccgtaaacgg ctggactcgg cgttcgacag cggcgatccc ggcctgctcg    2700
agcactacca gcaactggcc gcacggaccc tggaagtcct cgccggtgat atcggcgacc    2760
cgaatctcgg tctggacgac gcgacttggc agccggttgg cgaaaccgtc gacctgatcg    2820
tccatcccgc cgcgttggtc aaccacgtcc ttccctacac ccagctgttc ggccccaatg    2880
tcgtcggcac cgccgaaatc gtccggttgg cgatcacggc gcggcgcaag ccggtcacct    2940
acctgtcgac cgtcggagtg gccgaccagg tcgacccggc ggagtatcag gaggacagcg    3000
acgtccgcga gatgagcgcg gtgcgcgtcg tgcgcgagag ttacgccaac ggctacggca    3060
acagcaagtg ggcgggggag gtcctgctgc gcgaagcaca cgatctgtgt ggcttgccgg    3120
tcgcggtgtt ccgttcggac atgatcctgg cgcacagccg gtacgcgggt cagctcaacg    3180
tccaggacgt gttcacccgg ctgatcctca gcctggtcgc caccggcatc gcgccgtact    3240
cgttctaccg aaccgacgcg gacggcaacc ggcagcgggc ccactacgac ggtctgcccg    3300
ccgatttcac ggcggcggcg atcaccgcgc tcggcatcca agccaccgaa ggcttccgga    3360
cctacgacgt gctcaatccg tacgacgatg gcatctccct cgatgaattc gtcgactggc    3420
tcgtcgaatc cggccacccg atccagcgca tcaccgacta cagcgactgg ttccaccgtt    3480
tcgagacggc gatccgcgcg ctgccggaaa gcaacgccca ggcctcggtg ctgccgttgc    3540
tggacgccta ccgcaacccc tgcccggcgg tccgcggcgc gatactcccg gccaaggagt    3600
tccaagcggc ggtgcaaaca gccaaaatcg gtccggaaca ggacatcccg catttgtccg    3660
cgccactgat cgataagtac gtcagcgatc tggaactgct tcagctgctc tgacggatat    3720
caggccgccg cgcgcacctc gtcggtgcgt tcggcgcctt cgcgccggag gcgaaacagg    3780
aataccgccg agccacccag gacagcggcg tagacgatga cgaagctgtt gatcaggacc    3840
tgggcgaccg gccaccacgg cgggaacagg aacagcccga cgacaacgta gtccgggctg    3900
tattcccacg tccacgcgcc gatcgagacg aagagcgcgg ccgaggcaag ccaccaccac    3960
ggctgcgact gcgccctgtg cagtagatag acgaacaggg gaacgaacca cacccagtgg    4020
tggtcccagg agaacggcga gaccgcgcag gcggtgaggc cggcgagggt gaccgcgagg    4080
agctgttcgc cacgccgata caggccgatg gtgacggcca gactcgccag cgcgacggag    4140
cccgcgatga gcagccacag ccacaccggc gccgggtgat gggtcaggtg cgcgatggcg    4200
ccgcggatgg attgattgga cgggtgcata tcgtccgcga tccgattgga ctggaagaac    4260
gtcgaggtcc agtactgccg ggaatcggcg ggcagcacga tccaggcgag gacgatggac    4320
gcgatgaaca ccgccacggc ggtgcacgcg gaccgccact gccgcaacgc gaggaattgc    4380
acgacgaagt agccagggac gagcttgatg cccgccgcca ccccgacgcc gaggccgcgc    4440
agcttgctgc ggtcgggccg ggagaagtcc cacagcacca gcagcatcag catcaggttg    4500
```

```
atctggccgt agaacagcgt tgtccggacg ggctcgatga acgcgcaggt gagcgccagt    4560
agggcgctga cgacggccag tctggcgttg atccggtacc                          4600

<210> SEQ ID NO 38
<211> LENGTH: 4600
<212> TYPE: DNA
<213> ORGANISM: Nocardia

<400> SEQUENCE: 38
ggtaccggca atacctggat aagcggtcgg atcctgggcc gctgcggtgg agtggccgcc      60
gttccggccc gatgtggcca agaccactcg agtcaccgcc gcgtatcacc ttcccggaag    120
tatttactta ggctaacgtg ttttacgggt tgcagggctt ttcctactta tgacaaggga    180
ggcttgccat ggcagtggat agtccggatg agcggctaca gcgccgcatt gcacagttgt    240
ttgcagaaga tgagcaggtc aaggccgcac gtccgctcga agcggtgagc gcggcggtga    300
gcgcgcccgg tatgcggctg gcgcagatcg ccgccactgt tatggcgggt tacgccgacc    360
gcccggccgc cgggcagcgt gcgttcgaac tgaacaccga cgacgcgacg ggccgcacct    420
cgctgcggtt acttccccga ttcgagacca tcacctatcg cgaactgtgg cagcgagtcg    480
gcgaggttgc cgcggcctgg catcatgatc ccgagaaccc cttgcgcgca ggtgatttcg    540
tcgccctgct cggcttcacc agcatcgact acgccaccct cgacctggcc gatatccacc    600
tcggcgcggt taccgtgccg ttgcaggcca gcgcggcggt gtcccagctg atcgctatcc    660
tcaccgagac ttcgccgcgg ctgctcgcct cgaccccgga gcacctcgat gcggcggtcg    720
agtgcctact cgcgggcacc acaccggaac gactggtggt cttcgactac cacccgagg    780 acgacgacca gcgtgcggcc ttcgaatccc ccgccgccg ccttgccgac gcgggcagct    840
cggtgatcgt cgaaacgctc gatgccgtgc gtgcccgggg ccgcgactta ccggccgcgc    900
cactgttcgt tcccgacacc gacgacgacc cgctggccct gctgatctac acctccggca    960
gcaccggaac gccgaagggc gcgatgtaca ccaatcggtt ggccgccacg atgtggcagg   1020
ggaactcgat gctgcagggg aactcgcaac gggtcgggat caatctcaac tacatgccga   1080
tgagccacat cgccggtcgc atatcgctgt tcggcgtgct cgctcgcggt ggcaccgcat   1140
acttcgcggc caagagcgac atgtcgcacac tgttcgaaga catcggcttg gtacgtccca   1200
ccgagatctt cttcgtcccg cgcgtgtgcg acatggtctt ccagcgctat cagagcgagc   1260
tggaccggcg ctcggtggcg ggcgccgacc tggacacgct cgatcgggaa gtgaaagccg   1320
acctccggca gaactacctc ggtgggcgct tcctggtggc ggtcgtcggc agcgcgccgc   1380
tggccgcgga gatgaagacg ttcatggagt ccgtcctcga tctgccactg cacgacgggt   1440
acgggtcgac cgaggcgggc gcaagcgtgc tgctcgacaa ccagatccag cggccgccgg   1500
tgctcgatta caagctcgtc gacgtgcccg aactgggtta cttccgcacc gaccggccgc   1560
atccgcgcgg tgagctgttg ttgaaggcgg agaccacgat tccgggctac tacaagcggc   1620
ccgaggtcac cgcggagatc ttcgacgagg acggcttcta caagaccggc gatatcgtgg   1680
ccgagctcga gcacgatcgg ctggtctatg tcgaccgtcg caacaatgtg ctcaaactgt   1740
cgcagggcga gttcgtgacc gtcgcccatc tcgaggccgt gttcgccagc agcccgctga   1800
tccggcagat cttcatctac ggcagcagcg aacgttccta tctgctcgcg gtgatcgtcc   1860
ccaccgacga cgcgctgcgc ggccgcgaca ccgccacctt gaaatcggca ctggccgaat   1920
cgattcagcg catcgccaag gacgcgaacc tgcagcccta cgagattccg cgcgattcc   1980
```

```
tgatcgagac cgagccgttc accatcgcca acggactgct ctccggcatc gcgaagctgc    2040
tgcgccccaa tctgaaggaa cgctacggcg ctcagctgga gcagatgtac accgatctcg    2100
cgacaggcca ggccgatgag ctgctcgccc tgcgccgcga agccgccgac ctgccggtgc    2160
tcgaaaccgt cagccgggca gcgaaagcga tgctcggcgt cgcctccgcc gatatgcgtc    2220
ccgacgcgca cttcaccgac ctgggcggcg attcccttt  cgcgctgtcg ttctcgaacc    2280
tgctgcacga gatcttcggg gtcgaggtgc cggtgggtgt cgtcgtcagc ccggcgaacg    2340
agctgcgcga tctggcgaat tacattgagg cggaacgcaa ctcgggcgcg aagcgtccca    2400
ccttcacctc ggtgcacggc ggcggttccg agatccgcgc cgccgatctg accctcgaca    2460
agttcatcga tgcccgcacc ctggccgccg ccgacagcat tccgcacgcg ccggtgccag    2520
cgcagacggt gctgctgacc ggcgcgaacg gctacctcgg ccggttcctg tgcctggaat    2580
ggctggagcg gctggacaag acgggtggca cgctgatctg cgtcgtgcgc ggtagtgacg    2640
cggccgcggc ccgtaaacgg ctggactcgg cgttcgacag cggcgatccc ggcctgctcg    2700
agcactacca gcaactggcc gcacggaccc tggaagtcct cgccggtgat atcggcgacc    2760
cgaatctcgg tctggacgac gcgacttggc agcggttggc cgaaaccgtc gacctgatcg    2820
tccatcccgc cgcgttggtc aaccacgtcc ttccctacac ccagctgttc ggccccaatg    2880
tcgtcggcac cgccgaaatc gtccggttgg cgatcacggc gcggcgcaag ccggtcacct    2940
acctgtcgac cgtcggagtg gccgaccagg tcgacccggc ggagtatcag gaggacagcg    3000
acgtccgcga gatgagcgcg gtgcgcgtcg tgcgcgagag ttacgccaac ggctacggca    3060
acagcaagtg ggcgggggag gtcctgctgc gcgaagcaca cgatctgtgt ggcttgccgg    3120
tcgcggtgtt ccgttcggac atgatcctgg cgcacagccg gtacgcgggt cagctcaacg    3180
tccaggacgt gttcacccgg ctgatcctca gcctggtcgc caccggcatc gcgccgtact    3240
cgttctaccg aaccgacgcg gacggcaacc ggcagcgggc ccactacgac ggtctgcccg    3300
ccgatttcac ggcggcggcg atcaccgcgc tcggcatcca agccaccgaa ggcttccgga    3360
cctacgacgt gctcaatccg tacgacgatg gcatctccct cgatgaattc gtcgactggc    3420
tcgtcgaatc cggccacccg atccagcgca tcaccgacta cagcgactgg ttccaccgtt    3480
tcgagacggc gatccgcgcg ctgccggaaa agcaacgcca ggcctcggtg ctgccgttgc    3540
tggacgccta ccgcaacccc tgcccggcgg tccgcggcgc gatactcccg gccaaggagt    3600
tccaagcggc ggtgcaaaca gccaaaatcg gtccggaaca ggacatcccg catttgtccg    3660
cgccactgat cgataagtac gtcagcgatc tggaactgct tcagctgctc tgacggatat    3720
caggccgccg cgcgcacctc gtcggtgcgt tcggcgcctt cgcgccggag gcgaaacagg    3780
aataccgccg agccacccag gacagcggcg tagacgatga cgaagctgtt gatcaggacc    3840
tgggcgaccg gccaccacgg cgggaacagg aacagcccga cgacaacgta gtccgggctg    3900
tattcccacg tccacgcgcc gatcgagacg aagagcgcgg ccgaggcaag ccaccaccac    3960
ggctgcgact gcgccctgtg cagtagatag acgaacaggg gaacgaacca cacccagtgg    4020
tggtcccagg agaacggcga gaccgcgcag gcggtgaggc cggcgagggt gaccgcgagg    4080
agctgttcgc cacgccgata caggccgatg gtgacggcca gactcgccag cgcgacggag    4140
cccgcgatga gcagccacag ccacaccggc gccgggtgat gggtcaggtg cgcgatggcg    4200
ccgcggatgg attgattgga cgggtgcata tcgtccgcga tccgattgga ctggaagaac    4260
gtcgaggtcc agtactgccg ggaatcggcg ggcagcacga tccaggcgag gacgatggac    4320
gcgatgaaca ccgccacggc ggtgcacgcg gaccgccact gccgcaacgc gaggaattgc    4380
```

```
acgacgaagt agccagggac gagcttgatg cccgccgcca ccccgacgcc gaggccgcgc    4440
agcttgctgc ggtcgggccg ggagaagtcc cacagcacca gcagcatcag catcaggttg    4500
atctggccgt agaacagcgt tgtccggacg ggctcgatga acgcgcaggt gagcgccagt    4560
agggcgctga cgacggccag tctggcgttg atccggtacc                          4600
```

<210> SEQ ID NO 39
<211> LENGTH: 1174
<212> TYPE: PRT
<213> ORGANISM: Nocardia

<400> SEQUENCE: 39

```
Met Ala Val Asp Ala Pro Asp Glu Arg Leu Gln Arg Arg Ile Ala Gln
1               5                   10                  15

Leu Phe Ala Glu Asp Glu Gln Val Lys Ala Ala Arg Pro Leu Glu Ala
            20                  25                  30

Val Ser Ala Ala Val Ser Ala Pro Gly Met Arg Leu Ala Gln Ile Ala
        35                  40                  45

Ala Thr Val Met Ala Gly Tyr Ala Asp Arg Pro Ala Ala Gly Gln Arg
    50                  55                  60

Ala Phe Glu Leu Asn Thr Asp Asp Ala Thr Gly Arg Thr Ser Leu Arg
65                  70                  75                  80

Leu Leu Pro Arg Phe Glu Thr Ile Thr Tyr Arg Glu Leu Trp Gln Arg
                85                  90                  95

Val Gly Glu Val Ala Ala Ala Trp His His Asp Pro Glu Asn Pro Leu
            100                 105                 110

Arg Ala Gly Asp Phe Val Ala Leu Leu Gly Phe Thr Ser Ile Asp Tyr
        115                 120                 125

Ala Thr Leu Asp Leu Ala Asp Ile His Leu Gly Ala Val Thr Val Pro
    130                 135                 140

Leu Gln Ala Ser Ala Ala Val Ser Gln Leu Ile Ala Ile Leu Thr Glu
145                 150                 155                 160

Thr Ser Pro Arg Leu Leu Ala Ser Thr Pro Glu His Leu Asp Ala Ala
                165                 170                 175

Val Glu Cys Leu Leu Ala Gly Thr Thr Pro Glu Arg Leu Val Val Phe
            180                 185                 190

Asp Tyr His Pro Glu Asp Asp Gln Arg Ala Ala Phe Glu Ser Ala
        195                 200                 205

Arg Arg Arg Leu Ala Asp Ala Gly Ser Ser Val Ile Val Glu Thr Leu
    210                 215                 220

Asp Ala Val Arg Ala Arg Gly Arg Asp Leu Pro Ala Ala Pro Leu Phe
225                 230                 235                 240

Val Pro Asp Thr Asp Asp Asp Pro Leu Ala Leu Leu Ile Tyr Thr Ser
                245                 250                 255

Gly Ser Thr Gly Thr Pro Lys Gly Ala Met Tyr Thr Asn Arg Leu Ala
            260                 265                 270

Ala Thr Met Trp Gln Gly Asn Ser Met Leu Gln Gly Asn Ser Gln Arg
        275                 280                 285

Val Gly Ile Asn Leu Asn Tyr Met Pro Met Ser His Ile Ala Gly Arg
    290                 295                 300

Ile Ser Leu Phe Gly Val Leu Ala Arg Gly Gly Thr Ala Tyr Phe Ala
305                 310                 315                 320

Ala Lys Ser Asp Met Ser Thr Leu Phe Glu Asp Ile Gly Leu Val Arg
                325                 330                 335
```

```
Pro Thr Glu Ile Phe Phe Val Pro Arg Val Cys Asp Met Val Phe Gln
        340                 345                 350
Arg Tyr Gln Ser Glu Leu Asp Arg Arg Ser Val Ala Gly Ala Asp Leu
            355                 360                 365
Asp Thr Leu Asp Arg Glu Val Lys Ala Asp Leu Arg Gln Asn Tyr Leu
        370                 375                 380
Gly Gly Arg Phe Leu Val Ala Val Val Gly Ser Ala Pro Leu Ala Ala
385                 390                 395                 400
Glu Met Lys Thr Phe Met Glu Ser Val Leu Asp Leu Pro Leu His Asp
            405                 410                 415
Gly Tyr Gly Ser Thr Glu Ala Gly Ala Ser Val Leu Leu Asp Asn Gln
        420                 425                 430
Ile Gln Arg Pro Pro Val Leu Asp Tyr Lys Leu Val Asp Val Pro Glu
            435                 440                 445
Leu Gly Tyr Phe Arg Thr Asp Arg Pro His Pro Arg Gly Glu Leu Leu
        450                 455                 460
Leu Lys Ala Glu Thr Thr Ile Pro Gly Tyr Tyr Lys Arg Pro Glu Val
465                 470                 475                 480
Thr Ala Glu Ile Phe Asp Glu Asp Gly Phe Tyr Lys Thr Gly Asp Ile
                485                 490                 495
Val Ala Glu Leu Glu His Asp Arg Leu Val Tyr Val Asp Arg Arg Asn
            500                 505                 510
Asn Val Leu Lys Leu Ser Gln Gly Glu Phe Val Thr Val Ala His Leu
        515                 520                 525
Glu Ala Val Phe Ala Ser Ser Pro Leu Ile Arg Gln Ile Phe Ile Tyr
    530                 535                 540
Gly Ser Ser Glu Arg Ser Tyr Leu Leu Ala Val Ile Val Pro Thr Asp
545                 550                 555                 560
Asp Ala Leu Arg Gly Arg Asp Thr Ala Thr Leu Lys Ser Ala Leu Ala
                565                 570                 575
Glu Ser Ile Gln Arg Ile Ala Lys Asp Ala Asn Leu Gln Pro Tyr Glu
            580                 585                 590
Ile Pro Arg Asp Phe Leu Ile Glu Thr Glu Pro Phe Thr Ile Ala Asn
        595                 600                 605
Gly Leu Leu Ser Gly Ile Ala Lys Leu Leu Arg Pro Asn Leu Lys Glu
610                 615                 620
Arg Tyr Gly Ala Gln Leu Glu Gln Met Tyr Thr Asp Leu Ala Thr Gly
625                 630                 635                 640
Gln Ala Asp Glu Leu Leu Ala Leu Arg Glu Ala Ala Asp Leu Pro
                645                 650                 655
Val Leu Glu Thr Val Ser Arg Ala Ala Lys Ala Met Leu Gly Val Ala
            660                 665                 670
Ser Ala Asp Met Arg Pro Asp Ala His Phe Thr Asp Leu Gly Gly Asp
        675                 680                 685
Ser Leu Ser Ala Leu Ser Phe Ser Asn Leu Leu His Glu Ile Phe Gly
    690                 695                 700
Val Glu Val Pro Val Gly Val Val Ser Pro Ala Asn Glu Leu Arg
705                 710                 715                 720
Asp Leu Ala Asn Tyr Ile Glu Ala Glu Arg Asn Ser Gly Ala Lys Arg
                725                 730                 735
Pro Thr Phe Thr Ser Val His Gly Gly Gly Ser Glu Ile Arg Ala Ala
            740                 745                 750
```

```
Asp Leu Thr Leu Asp Lys Phe Ile Asp Ala Arg Thr Leu Ala Ala Ala
            755                 760                 765

Asp Ser Ile Pro His Ala Pro Val Pro Ala Gln Thr Val Leu Leu Thr
        770                 775                 780

Gly Ala Asn Gly Tyr Leu Gly Arg Phe Leu Cys Leu Glu Trp Leu Glu
785                 790                 795                 800

Arg Leu Asp Lys Thr Gly Gly Thr Leu Ile Cys Val Val Arg Gly Ser
                805                 810                 815

Asp Ala Ala Ala Arg Lys Arg Leu Asp Ser Ala Phe Asp Ser Gly
            820                 825                 830

Asp Pro Gly Leu Leu Glu His Tyr Gln Gln Leu Ala Ala Arg Thr Leu
            835                 840                 845

Glu Val Leu Ala Gly Asp Ile Gly Asp Pro Asn Leu Gly Leu Asp Asp
850                 855                 860

Ala Thr Trp Gln Arg Leu Ala Glu Thr Val Asp Leu Ile Val His Pro
865                 870                 875                 880

Ala Ala Leu Val Asn His Val Leu Pro Tyr Thr Gln Leu Phe Gly Pro
                885                 890                 895

Asn Val Val Gly Thr Ala Glu Ile Val Arg Leu Ala Ile Thr Ala Arg
            900                 905                 910

Arg Lys Pro Val Thr Tyr Leu Ser Thr Val Gly Val Ala Asp Gln Val
            915                 920                 925

Asp Pro Ala Glu Tyr Gln Glu Asp Ser Asp Val Arg Glu Met Ser Ala
            930                 935                 940

Val Arg Val Arg Glu Ser Tyr Ala Asn Gly Tyr Gly Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Ser Asp Met Ile Leu Ala His Ser Arg Tyr
            980                 985                 990

Ala Gly Gln Leu Asn Val Gln Asp Val Phe Thr Arg Leu Ile Leu Ser
            995                 1000                1005

Leu Val Ala Thr Gly Ile Ala Pro Tyr Ser Phe Tyr Arg Thr Asp
        1010                1015                1020

Ala Asp Gly Asn Arg Gln Arg Ala His Tyr Asp Gly Leu Pro Ala
    1025                1030                1035

Asp Phe Thr Ala Ala Ala Ile Thr Ala Leu Gly Ile Gln Ala Thr
    1040                1045                1050

Glu Gly Phe Arg Thr Tyr Asp Val Leu Asn Pro Tyr Asp Asp Gly
    1055                1060                1065

Ile Ser Leu Asp Glu Phe Val Asp Trp Leu Val Glu Ser Gly His
    1070                1075                1080

Pro Ile Gln Arg Ile Thr Asp Tyr Ser Asp Trp Phe His Arg Phe
    1085                1090                1095

Glu Thr Ala Ile Arg Ala Leu Pro Glu Lys Gln Arg Gln Ala Ser
    1100                1105                1110

Val Leu Pro Leu Leu Asp Ala Tyr Arg Asn Pro Cys Pro Ala Val
    1115                1120                1125

Arg Gly Ala Ile Leu Pro Ala Lys Glu Phe Gln Ala Ala Val Gln
    1130                1135                1140

Thr Ala Lys Ile Gly Pro Glu Gln Asp Ile Pro His Leu Ser Ala
    1145                1150                1155

Pro Leu Ile Asp Lys Tyr Val Ser Asp Leu Glu Leu Leu Gln Leu
```

```
                        1160                 1165                 1170
Leu

<210> SEQ ID NO 40
<211> LENGTH: 16
<212> TYPE: PRT
<213> ORGANISM: Nicordia

<400> SEQUENCE: 40

Leu Ile Tyr Thr Ser Gly Ser Thr Gly Thr Pro Lys Gly Ala Met Tyr
1               5                  10                  15

<210> SEQ ID NO 41
<211> LENGTH: 16
<212> TYPE: PRT
<213> ORGANISM: M. tuberculosis

<400> SEQUENCE: 41

Leu Ile Tyr Thr Ser Gly Ser Thr Gly Ala Pro Lys Gly Ala Met Tyr
1               5                  10                  15

<210> SEQ ID NO 42
<211> LENGTH: 16
<212> TYPE: PRT
<213> ORGANISM: Saccharomyces

<400> SEQUENCE: 42

Leu Ser Phe Thr Ser Gly Ser Glu Gly Ile Pro Lys Gly Val Leu Gly
1               5                  10                  15

<210> SEQ ID NO 43
<211> LENGTH: 10
<212> TYPE: PRT
<213> ORGANISM: hypothetical

<400> SEQUENCE: 43

Thr Ser Gly Ser Glu Gly Arg Pro Lys Gly
1               5                  10

<210> SEQ ID NO 44
<211> LENGTH: 11
<212> TYPE: PRT
<213> ORGANISM: hypothetical

<400> SEQUENCE: 44

Leu Tyr Thr Ser Gly Ser Gly Pro Lys Gly Met
1               5                  10

<210> SEQ ID NO 45
<211> LENGTH: 14
<212> TYPE: PRT
<213> ORGANISM: Nicordia

<400> SEQUENCE: 45

Asp Leu Pro Leu His Asp Gly Tyr Gly Ser Thr Glu Ala Gly
1               5                  10

<210> SEQ ID NO 46
<211> LENGTH: 14
<212> TYPE: PRT
<213> ORGANISM: M. tuberculosis

<400> SEQUENCE: 46

Asp Val His Leu Val Glu Gly Tyr Gly Ser Thr Glu Ala Gly
```

```
<210> SEQ ID NO 47
<211> LENGTH: 14
<212> TYPE: PRT
<213> ORGANISM: Saccharomyces

<400> SEQUENCE: 47

Asn Cys Arg Ile Val Asn Met Tyr Gly Thr Thr Glu Thr Gln
1               5                   10

<210> SEQ ID NO 48
<211> LENGTH: 8
<212> TYPE: PRT
<213> ORGANISM: hypothetical

<400> SEQUENCE: 48

Ile Val Asn Met Tyr Gly Thr Thr
1               5

<210> SEQ ID NO 49
<211> LENGTH: 7
<212> TYPE: PRT
<213> ORGANISM: hypothetical

<400> SEQUENCE: 49

Leu Val Tyr Gly Ser Thr Glu
1               5

<210> SEQ ID NO 50
<211> LENGTH: 14
<212> TYPE: PRT
<213> ORGANISM: Nicordia

<400> SEQUENCE: 50

Asp Glu Asp Gly Phe Tyr Lys Thr Gly Asp Ile Val Ala Glu
1               5                   10

<210> SEQ ID NO 51
<211> LENGTH: 14
<212> TYPE: PRT
<213> ORGANISM: M. tuberculosis

<400> SEQUENCE: 51

Asp Pro Asp Gly Phe Tyr Arg Thr Gly Asp Ile Met Ala Lys
1               5                   10

<210> SEQ ID NO 52
<211> LENGTH: 14
<212> TYPE: PRT
<213> ORGANISM: Saccharomyces

<400> SEQUENCE: 52

Pro Arg Asp Arg Leu Tyr Arg Thr Gly Asp Leu Gly Arg Tyr
1               5                   10

<210> SEQ ID NO 53
<211> LENGTH: 8
<212> TYPE: PRT
<213> ORGANISM: hypothetical

<400> SEQUENCE: 53

Arg Leu Tyr Arg Ser Gly Asp Leu
1               5
```

<210> SEQ ID NO 54
<211> LENGTH: 7
<212> TYPE: PRT
<213> ORGANISM: hypothetical

<400> SEQUENCE: 54

Asp Tyr Arg Thr Gly Asp Leu
1               5

<210> SEQ ID NO 55
<211> LENGTH: 13
<212> TYPE: PRT
<213> ORGANISM: Nicordia

<400> SEQUENCE: 55

Asp Ala Asn Leu Gln Pro Tyr Glu Ile Pro Arg Asp Phe
1               5                   10

<210> SEQ ID NO 56
<211> LENGTH: 13
<212> TYPE: PRT
<213> ORGANISM: M. tuberculosis

<400> SEQUENCE: 56

Ala Ala Gly Leu Gln Ser Tyr Glu Ile Pro Arg Asp Phe
1               5                   10

<210> SEQ ID NO 57
<211> LENGTH: 13
<212> TYPE: PRT
<213> ORGANISM: Saccharomyces

<400> SEQUENCE: 57

Glu Pro Thr Leu Ile Thr Phe Met Val Pro Arg Phe Asp
1               5                   10

<210> SEQ ID NO 58
<211> LENGTH: 7
<212> TYPE: PRT
<213> ORGANISM: hypothetical

<400> SEQUENCE: 58

Leu Val Ser Tyr Phe Val Pro
1               5

<210> SEQ ID NO 59
<211> LENGTH: 7
<212> TYPE: PRT
<213> ORGANISM: hypothetical

<400> SEQUENCE: 59

Leu Ser Tyr Ile Pro Arg Phe
1               5

<210> SEQ ID NO 60
<211> LENGTH: 18
<212> TYPE: PRT
<213> ORGANISM: Nicordia

<400> SEQUENCE: 60

Asn Gly Leu Leu Ser Gly Ile Ala Lys Leu Leu Arg Pro Asn Leu Lys
1               5                   10                  15

Glu Arg

```
<210> SEQ ID NO 61
<211> LENGTH: 18
<212> TYPE: PRT
<213> ORGANISM: M. tuberculosis

<400> SEQUENCE: 61

Asn Gly Leu Leu Thr Gly Ile Arg Lys Leu Ala Arg Pro Gln Leu Lys
1               5                   10                  15

Lys Phe

<210> SEQ ID NO 62
<211> LENGTH: 18
<212> TYPE: PRT
<213> ORGANISM: Saccharomyces

<400> SEQUENCE: 62

Lys Leu Pro Leu Asn Pro Asn Gly Lys Val Asp Lys Pro Lys Leu Gln
1               5                   10                  15

Phe Pro

<210> SEQ ID NO 63
<211> LENGTH: 12
<212> TYPE: PRT
<213> ORGANISM: hypothetical

<400> SEQUENCE: 63

Leu Asn Pro Asn Gly Lys Ile Asp Lys Pro Ala Leu
1               5                   10

<210> SEQ ID NO 64
<211> LENGTH: 7
<212> TYPE: PRT
<213> ORGANISM: hypothetical

<400> SEQUENCE: 64

Leu Gly Lys Val Lys Pro Leu
1               5

<210> SEQ ID NO 65
<211> LENGTH: 14
<212> TYPE: PRT
<213> ORGANISM: Nicordia

<400> SEQUENCE: 65

Phe Thr Asp Leu Gly Gly Asp Ser Leu Ser Ala Leu Ser Phe
1               5                   10

<210> SEQ ID NO 66
<211> LENGTH: 14
<212> TYPE: PRT
<213> ORGANISM: M. tuberculosis

<400> SEQUENCE: 66

Phe Ala Asp Leu Gly Gly Asp Ser Leu Ser Ala Leu Ser Leu
1               5                   10

<210> SEQ ID NO 67
<211> LENGTH: 14
<212> TYPE: PRT
<213> ORGANISM: Saccharomyces

<400> SEQUENCE: 67

Phe Phe Asp Leu Gly Gly His Ser Ile Leu Ala Thr Lys Met
```

```
1               5              10

<210> SEQ ID NO 68
<211> LENGTH: 9
<212> TYPE: PRT
<213> ORGANISM: hypothetical

<400> SEQUENCE: 68

Leu Gly Gly His Ser Ile Leu Ala Gln
1               5

<210> SEQ ID NO 69
<211> LENGTH: 8
<212> TYPE: PRT
<213> ORGANISM: hypothetical

<400> SEQUENCE: 69

Phe Asp Leu Gly Gly Ser Ile Ala
1               5

<210> SEQ ID NO 70
<211> LENGTH: 13
<212> TYPE: PRT
<213> ORGANISM: Nicordia

<400> SEQUENCE: 70

Leu Leu Thr Gly Ala Asn Gly Tyr Leu Gly Arg Phe Leu
1               5                   10

<210> SEQ ID NO 71
<211> LENGTH: 13
<212> TYPE: PRT
<213> ORGANISM: M. tuberculosis

<400> SEQUENCE: 71

Leu Leu Thr Gly Ala Thr Gly Phe Leu Gly Arg Tyr Leu
1               5                   10

<210> SEQ ID NO 72
<211> LENGTH: 13
<212> TYPE: PRT
<213> ORGANISM: Saccharomyces

<400> SEQUENCE: 72

Phe Val Thr Gly Val Thr Gly Phe Leu Gly Ser Tyr Ile
1               5                   10

<210> SEQ ID NO 73
<211> LENGTH: 10
<212> TYPE: PRT
<213> ORGANISM: hypothetical

<400> SEQUENCE: 73

Gly Ala Thr Gly Phe Leu Gly Ala His Ile
1               5                   10

<210> SEQ ID NO 74
<211> LENGTH: 11
<212> TYPE: PRT
<213> ORGANISM: hypothetical

<400> SEQUENCE: 74

Val Thr Gly Ala Thr Gly Phe Leu Gly Tyr Ile
1               5                   10
```

```
<210> SEQ ID NO 75
<211> LENGTH: 13
<212> TYPE: PRT
<213> ORGANISM: Nicordia

<400> SEQUENCE: 75

Tyr Ala Asn Gly Tyr Gly Asn Ser Lys Trp Ala Gly Glu
1               5                   10

<210> SEQ ID NO 76
<211> LENGTH: 13
<212> TYPE: PRT
<213> ORGANISM: M. tuberculosis

<400> SEQUENCE: 76

Tyr Ala Asn Gly Tyr Ala Asn Ser Lys Trp Ala Gly Glu
1               5                   10

<210> SEQ ID NO 77
<211> LENGTH: 13
<212> TYPE: PRT
<213> ORGANISM: Saccharomyces

<400> SEQUENCE: 77

Leu Thr Gly Gly Tyr Gly Gln Ser Lys Trp Ala Ala Glu
1               5                   10

<210> SEQ ID NO 78
<211> LENGTH: 7
<212> TYPE: PRT
<213> ORGANISM: hypothetical

<400> SEQUENCE: 78

Gly Tyr Gly Gln Ser Lys Trp
1               5

<210> SEQ ID NO 79
<211> LENGTH: 10
<212> TYPE: PRT
<213> ORGANISM: hypothetical

<400> SEQUENCE: 79

Gly Tyr Gly Gln Ser Lys Trp Ala Ala Glu
1               5                   10

<210> SEQ ID NO 80
<211> LENGTH: 1391
<212> TYPE: PRT
<213> ORGANISM: Saccharomyces

<400> SEQUENCE: 80

Thr Asn Glu Lys Val Trp Ile Glu Lys Leu Asp Asn Pro Thr Leu Ser
1               5                   10                  15

Val Leu Pro His Asp Phe Leu Arg Pro Gln Gln Glu Pro Tyr Thr Lys
                20                  25                  30

Gln Ala Thr Tyr Ser Leu Gln Leu Pro Gln Leu Asp Val Pro His Asp
            35                  40                  45

Ser Phe Ser Asn Lys Tyr Ala Val Ala Leu Ser Val Trp Ala Ala Leu
        50                  55                  60

Ile Tyr Arg Val Thr Gly Asp Asp Ile Val Leu Tyr Ile Ala Asn
65                  70                  75                  80

Asn Lys Ile Leu Arg Phe Asn Ile Gln Pro Thr Trp Ser Phe Asn Glu
```

-continued

```
                    85                  90                  95
Leu Tyr Ser Thr Ile Asn Asn Glu Leu Asn Lys Leu Asn Ser Ile Glu
                100                 105                 110

Ala Asn Phe Ser Phe Asp Glu Leu Ala Glu Lys Ile Gln Ser Cys Gln
                115                 120                 125

Asp Leu Glu Arg Thr Pro Gln Leu Phe Arg Leu Ala Phe Leu Glu Asn
            130                 135                 140

Gln Asp Phe Lys Leu Asp Glu Phe Lys His His Leu Val Asp Phe Ala
145                 150                 155                 160

Leu Asn Leu Asp Thr Ser Asn Asn Ala His Val Leu Asn Leu Ile Tyr
                165                 170                 175

Asn Ser Leu Leu Tyr Ser Asn Glu Arg Val Thr Ile Val Ala Asp Gln
            180                 185                 190

Phe Thr Gln Tyr Leu Thr Ala Ala Leu Ser Asp Pro Ser Asn Cys Ile
        195                 200                 205

Thr Lys Ile Ser Leu Ile Thr Ala Ser Ser Lys Asp Ser Leu Pro Asp
    210                 215                 220

Pro Thr Lys Asn Leu Gly Trp Cys Asp Phe Val Gly Cys Ile His Asp
225                 230                 235                 240

Ile Phe Gln Asp Asn Ala Glu Ala Phe Pro Glu Arg Thr Cys Val Val
                245                 250                 255

Glu Thr Pro Thr Leu Asn Ser Asp Lys Ser Arg Ser Phe Thr Tyr Arg
            260                 265                 270

Asp Ile Asn Arg Thr Ser Asn Ile Val Ala His Tyr Leu Ile Lys Thr
        275                 280                 285

Gly Ile Lys Arg Gly Asp Val Val Met Ile Tyr Ser Ser Arg Gly Val
    290                 295                 300

Asp Leu Met Val Cys Val Met Gly Val Leu Lys Ala Gly Ala Thr Phe
305                 310                 315                 320

Ser Val Ile Asp Pro Ala Tyr Pro Pro Ala Arg Gln Thr Ile Tyr Leu
                325                 330                 335

Gly Val Ala Lys Pro Arg Gly Leu Ile Val Ile Arg Ala Ala Gly Gln
            340                 345                 350

Leu Asp Gln Leu Val Glu Asp Tyr Ile Asn Asp Glu Leu Glu Ile Val
        355                 360                 365

Ser Arg Ile Asn Ser Ile Ala Ile Gln Glu Asn Gly Thr Ile Glu Gly
    370                 375                 380

Gly Lys Leu Asp Asn Gly Glu Asp Val Leu Ala Pro Tyr Asp His Tyr
385                 390                 395                 400

Lys Asp Thr Arg Thr Gly Val Val Val Gly Pro Asp Ser Asn Pro Thr
                405                 410                 415

Leu Ser Phe Thr Ser Gly Ser Glu Gly Ile Pro Lys Gly Val Leu Gly
            420                 425                 430

Arg His Phe Ser Leu Ala Tyr Tyr Phe Asn Trp Met Ser Lys Arg Phe
        435                 440                 445

Asn Leu Thr Glu Asn Asp Lys Phe Thr Met Leu Ser Gly Ile Ala His
    450                 455                 460

Asp Pro Ile Gln Arg Asp Met Phe Thr Pro Leu Phe Leu Gly Ala Gln
465                 470                 475                 480

Leu Tyr Val Pro Thr Gln Asp Asp Ile Gly Thr Pro Gly Arg Leu Ala
                485                 490                 495

Glu Trp Met Ser Lys Tyr Gly Cys Thr Val Thr His Leu Thr Pro Ala
            500                 505                 510
```

-continued

```
Met Gly Gln Leu Leu Thr Ala Gln Ala Thr Thr Pro Phe Pro Lys Leu
            515                 520                 525
His His Ala Phe Phe Val Gly Asp Ile Leu Thr Lys Arg Asp Cys Leu
    530                 535                 540
Arg Leu Gln Thr Leu Ala Glu Asn Cys Arg Ile Val Asn Met Tyr Gly
545                 550                 555                 560
Thr Thr Glu Thr Gln Arg Ala Val Ser Tyr Phe Glu Val Lys Ser Lys
                565                 570                 575
Asn Asp Asp Pro Asn Phe Leu Lys Lys Leu Lys Asp Val Met Pro Ala
            580                 585                 590
Gly Lys Gly Met Leu Asn Val Gln Leu Leu Val Val Asn Arg Asn Asp
        595                 600                 605
Arg Thr Gln Ile Cys Gly Ile Gly Glu Ile Gly Glu Ile Tyr Val Arg
    610                 615                 620
Ala Gly Gly Leu Ala Glu Gly Tyr Arg Gly Leu Pro Glu Leu Asn Lys
625                 630                 635                 640
Glu Lys Phe Val Asn Asn Trp Phe Val Glu Lys Asp His Trp Asn Tyr
                645                 650                 655
Leu Asp Lys Asp Asn Gly Glu Pro Trp Arg Gln Phe Trp Leu Gly Pro
            660                 665                 670
Arg Asp Arg Leu Tyr Arg Thr Gly Asp Leu Gly Arg Tyr Leu Pro Asn
        675                 680                 685
Gly Asp Cys Glu Cys Gly Arg Ala Asp Asp Gln Val Lys Ile Arg
    690                 695                 700
Gly Phe Arg Ile Glu Leu Gly Glu Ile Asp Thr His Ile Ser Gln His
705                 710                 715                 720
Pro Leu Val Arg Glu Asn Ile Thr Leu Val Arg Lys Asn Ala Asp Asn
                725                 730                 735
Glu Pro Thr Leu Ile Thr Phe Met Val Pro Arg Phe Asp Lys Pro Asp
            740                 745                 750
Asp Leu Ser Lys Phe Gln Ser Asp Val Pro Lys Glu Val Glu Thr Asp
        755                 760                 765
Pro Ile Val Lys Gly Leu Ile Gly Tyr His Leu Leu Ser Lys Asp Ile
    770                 775                 780
Arg Thr Phe Leu Lys Lys Arg Leu Ala Ser Tyr Ala Met Pro Ser Leu
785                 790                 795                 800
Ile Val Val Met Asp Lys Leu Pro Leu Asn Pro Asn Gly Lys Val Asp
                805                 810                 815
Lys Pro Lys Leu Gln Phe Pro Thr Pro Lys Gln Leu Asn Leu Val Ala
            820                 825                 830
Glu Asn Thr Val Ser Glu Thr Asp Ser Gln Phe Thr Asn Val Glu
        835                 840                 845
Arg Glu Val Arg Asp Leu Trp Leu Ser Ile Leu Pro Thr Lys Pro Ala
    850                 855                 860
Ser Val Ser Pro Asp Asp Ser Phe Phe Asp Leu Gly His Ser Ile
865                 870                 875                 880
Leu Ala Thr Lys Met Ile Phe Thr Leu Lys Lys Lys Leu Gln Val Asp
                885                 890                 895
Leu Pro Leu Gly Thr Ile Phe Lys Tyr Pro Thr Ile Lys Ala Phe Ala
            900                 905                 910
Ala Glu Ile Asp Arg Ile Lys Ser Ser Gly Gly Ser Ser Gln Gly Glu
        915                 920                 925
```

```
Val Val Glu Asn Val Thr Ala Asn Tyr Ala Glu Asp Ala Lys Lys Leu
    930                 935                 940

Val Glu Thr Leu Pro Ser Ser Tyr Pro Ser Arg Glu Tyr Phe Val Glu
945                 950                 955                 960

Pro Asn Ser Ala Glu Gly Lys Thr Thr Ile Asn Val Phe Val Thr Gly
                965                 970                 975

Val Thr Gly Phe Leu Gly Ser Tyr Ile Leu Ala Asp Leu Leu Gly Arg
            980                 985                 990

Ser Pro Lys Asn Tyr Ser Phe Lys  Val Phe Ala His Val  Arg Ala Lys
        995                 1000                 1005

Asp Glu  Glu Ala Ala  Phe Ala  Arg Leu Gln Lys Ala  Gly Ile Thr
    1010             1015                 1020

Tyr Gly  Thr Trp Asn Glu Lys  Phe Ala Ser Asn Ile  Lys Val Val
    1025                 1030                 1035

Leu Gly  Asp Leu Ser Lys Ser  Gln Phe Gly Leu Ser  Asp Glu Lys
    1040                 1045                 1050

Trp Met  Asp Leu Ala Asn Thr  Val Asp Ile Ile Ile  His Asn Gly
    1055                 1060                 1065

Ala Leu  Val His Trp Val Tyr  Pro Tyr Ala Lys Leu  Arg Asp Pro
    1070                 1075                 1080

Asn Val  Ile Ser Thr Ile Asn  Val Met Ser Leu Ala  Ala Val Gly
    1085                 1090                 1095

Lys Pro  Lys Phe Phe Asp Phe  Val Ser Ser Thr Ser  Thr Leu Asp
    1100                 1105                 1110

Thr Glu  Tyr Tyr Phe Asn Leu  Ser Asp Lys Leu Val  Ser Glu Gly
    1115                 1120                 1125

Lys Pro  Gly Ile Leu Glu Ser  Asp Asp Leu Met Asn  Ser Ala Ser
    1130                 1135                 1140

Gly Leu  Thr Gly Gly Tyr Gly  Gln Ser Lys Trp Ala  Ala Glu Tyr
    1145                 1150                 1155

Ile Ile  Arg Arg Ala Gly Glu  Arg Gly Leu Arg Gly  Cys Ile Val
    1160                 1165                 1170

Arg Pro  Gly Tyr Val Thr Gly  Ala Ser Ala Asn Gly  Ser Ser Asn
    1175                 1180                 1185

Thr Asp  Asp Phe Leu Leu Arg  Phe Leu Lys Gly Ser  Val Gln Leu
    1190                 1195                 1200

Gly Lys  Ile Pro Asp Ile Glu  Asn Ser Val Asn Met  Val Pro Val
    1205                 1210                 1215

Asp His  Val Ala Arg Val Val  Val Ala Thr Ser Leu  Asn Pro Pro
    1220                 1225                 1230

Lys Glu  Asn Glu Leu Ala Val  Ala Gln Val Thr Gly  His Pro Arg
    1235                 1240                 1245

Ile Leu  Phe Lys Asp Tyr Leu  Tyr Thr Leu His Asp  Tyr Gly Tyr
    1250                 1255                 1260

Asp Val  Glu Ile Glu Ser Tyr  Ser Lys Trp Lys Lys  Ser Leu Glu
    1265                 1270                 1275

Ala Ser  Val Ile Asp Arg Asn  Glu Glu Asn Ala Leu  Tyr Pro Leu
    1280                 1285                 1290

Leu His  Met Val Leu Asp Asn  Leu Pro Glu Ser Thr  Lys Ala Pro
    1295                 1300                 1305

Glu Leu  Asp Asp Arg Asn Ala  Val Ala Ser Leu Lys  Lys Asp Thr
    1310                 1315                 1320

Ala Trp  Thr Gly Val Asp Trp  Ser Asn Gly Ile Gly  Val Thr Pro
```

-continued

```
             1325                1330                1335
Glu Glu Val Gly Ile Tyr Ile Ala Phe Leu Asn Lys Val Gly Phe
         1340                1345                1350

Leu Pro Pro Pro Thr His Asn Asp Lys Leu Pro Leu Pro Ser Ile
         1355                1360                1365

Glu Leu Thr Gln Ala Gln Ile Ser Leu Val Ala Ser Gly Ala Gly
         1370                1375                1380

Ala Arg Gly Ser Ser Ala Ala Ala
         1385                1390
```

CARBOXYLIC ACID REDUCTASE POLYPEPTIDE, NUCLEOTIDE SEQUENCE ENCODING SAME AND METHODS OF USE

CROSS-REFERENCE TO RELATED APPLICATIONS

This is a Continuation Application of U.S. patent application Ser. No. 10/386,329 filed Mar. 11, 2003, now U.S. Pat. No. 7,056,714, which application is hereby incorporated by reference in its entirety.

BACKGROUND OF THE INVENTION

Microorganism-produced enzymes are widely used as a class of biocatalytic reagents in production of synthetic, aromatic, aliphatic and alicyclic aldehydes and alcohols are useful chemical intermediates in chemical, agrochemical, pharmaceutical and food industries. These enzymes are useful in a wide variety of reactions including, e.g., oxidations, reductions, hydrolyses, and carbon—carbon bond ligations.

Biocatalysts are valued for their intrinsic abilities to bind organic substrates and to catalyze highly specific and selective reactions under the mildest of reaction conditions. These selectivities and specificities are realized because of highly rigid interactions occurring between the enzyme active site and the substrate molecule. Biocatalytic reactions are particularly useful when they may be used to overcome difficulties encountered in catalysis achieved by the use of traditional chemical approaches.

Carboxylic acid reductases are complex, multicomponent enzyme systems, requiring the initial activation of carboxylic acids via formation of AMP and often coenzyme A intermediates (see, e.g., Hempel et al., Protein Sci. 2:1890-1900 (1993). Chemical methods for carboxylic acid reductions are generally poor usually requiring prior derivatization and product deblocking with multifunctional reactants.

An enzymatic reaction offers significant advantages over existing methods used in chemical reductions of carboxylic acids, or their derivatives. Unlike many substrates subjected to biocatalytic reactions, carboxylic acids are generally water soluble, rendering them of potentially broad application to this class of enzyme. The carboxylic acid reduction reaction appears to bear the usual desirable features of functional group specificity. It also functions well under mild reaction conditions and produces a high yield of product. The reduction of the activated carboxylic acid intermediate occurs stepwise to give aldehyde products (Gross et al., Eur. J. Biochem. 8:413-419; 420-425 (1969); Gross, Eur. J. Biochem. 31:585-592 (1972)).

The reduction of carboxylic acids by microorganisms is a relatively new biocatalytic reaction that has not yet been widely examined or exploited. Jezo and Zemek reported the reduction of aromatic acids to their corresponding benzaldehyde derivatives by Actinomycetes in Chem. Papers 40(2): 279-281 (1986). Kato et al. reported the reduction of benzoate to benzyl alcohol by *Nocardia asteroides* JCM 3016 (Agric. Biol. Chem. 52(7):1885-1886 (1988)), and Tsuda et al. described the reduction of 2-aryloxyacetic acids (Agric. Biol. Chem. 48(5): 1373-1374 (1984)) and arylpropionates (Chem. Pharm. Bull. 33(11):4657-4661 (1985)) by species of *Glomerella* and *Gloeosporium*. Microbial reductions of aromatic carboxylic acids, typically to their corresponding alcohols, have also been observed with whole cell biotransformations by *Clostridium thermoaceticum* (White et al., Eur. J. Biochem. 184:89-96 (1989)), and by *Neurospora* (Bachman et al., Arch. Biochem. Biophys. 91:326 (1960)). More recently, carboxylic acid reduction reactions have reportedly been catalyzed by whole cell preparations of *Aspergillus niger*, *Corynespora melonis* and *Coriolus* (Arfmann et al., Z. Naturforsch 48c:52-57 (1993); cf., Raman et al., J. Bacterial 84:1340-1341 (1962)), and by *Nocardia asteriodes* (Chen and Rosazza,. Appl. Environ. Microbiol. 60(4):1292-1296 (1994)).

Biocatalytic reductions of carboxylic acids are attractive to traditional chemical catalysis because the substrates are water soluble, blocking chemistry is not necessary, reductions are enantioselective (7), and the scope of the reaction is very broad (23, 32).

Aldehyde oxidoreductases are also known as carboxylic acid reductases (CAR), require ATP, $Mg^{2+}$, and NADPH as cofactors during carboxylic acid reduction (15, 16, 20, 23). The reduction reaction is a stepwise process involving initial binding of both ATP and the carboxylic acid to the enzyme, to form mixed 5'-adenylic acid-carbonyl anhydride intermediates (8, 14, 24, 26, 40) that are subsequently reduced by hydride delivery from NADPH to form the aldehyde product (15, 24).

Aromatic carboxylic acid reductases have been purified to homogeneity only from *Neurospora* (16) and *Nocardia* (20, 23). Although details of N— and internal amino acid sequences have been reported for the *Nocardia asteriodes* enzyme (23), complete gene sequences for these or any other carboxylic acid reductases are unknown.

It is an object of the present invention to provide a purified and isolated bacterial carboxylic acid reductase (CAR) gene and the protein encoded thereby.

It is yet another object of the invention to provide homologous nucleotide sequences and/or amino acid sequences which encode CAR.

It is yet another object of the invention to provide recombinant DNA using expression constructs, vectors, and recombinant cells using the sequences of the invention for production of recombinant CAR.

It is yet another object of the invention to provide for large scale production of and recovery of recombinant CAR, for use in production of synthetic, aromatic, aliphatic and alicyclic aldehydes and alcohols.

It is yet another embodiment of the invention to provide methods of synthesis of chemical compounds such as those for biocatalytically reducing a carboxylic acid, or a derivative thereof, to its corresponding aldehyde product(s), to provide a method of biocatalytically reducing a carboxylic acid, or a derivative thereof, to its corresponding intermediary by-product(s), as exemplified by acyl-AMP analogs, or to provide a method of biocatalytically reducing vanillic acid, or a precursor or derivative thereof, to vanillin, all using recombinant CAR as described the invention disclosed herein.

Additional objects, advantages and novel features of the invention will be set forth in part in the description which follows, and in part will become apparent to those skilled in the art on examination of the following, or may be learned by practice of the invention.

BRIEF SUMMARY OF THE INVENTION

The present invention provides polynucleotides, related polypeptides and all conservatively modified variants of purified and isolated CAR. The nucleotide sequence of CAR comprises the sequence found in SEQ ID NO: 1, 3, and 5. Sequences 3 and 5 provide examples of conservatively modified polynucleotides of SEQ ID NO: 1 and sequences 7, and 9, 11, are examples of sequences with 80, 90, and 95% sequence identity to SEQ ID NO:1 as also described herein.

Therefore, in one aspect, the present invention relates to an isolated nucleic acid comprising an isolated polynucleotide sequence encoding a CAR enzyme. In a further aspect, the present invention includes a nucleic acid selected from: (a) an isolated polynucleotide encoding a polypeptide of the present invention; (b) a polynucleotide having at least 80%, 90% or 95% identity to a polynucleotide of the present invention; (c) a polynucleotide comprising at least 25 nucleotides in length which hybridizes under high stringency conditions to a polynucleotide of the present invention; (d) a polynucleotide comprising a polynucleotide of the present invention; and (e) a polynucleotide which is complementary to the polynucleotide of (a) to (d).

In another aspect, the present invention relates to a recombinant expression cassette comprising a nucleic acid as described, supra. Additionally, the present invention relates to a vector containing the recombinant expression cassette. Further, the vector containing the recombinant expression cassette can facilitate the transcription and translation of the nucleic acid in a host cell. The present invention also relates to host cells able to express the polynucleotide of the present invention. A number of host cells could be used, such as but not limited to, microbial, mammalian, plant, or insect. In a preferred embodiment the host cell is a bacterial cell. In a more preferred embodiment the bacterial host cell is $E.\ Coli$. Thus the invention is also directed to transgenic cells, containing the nucleic acids of the present invention as well as cells, strains and lines derived therefrom.

This invention also provides an isolated polypeptide comprising (a) a polypeptide comprising at least 80%, 90% or 95% sequence identity to a polypeptide of the present invention (SEQ ID NO:2); (b) a polypeptide encoded by a nucleic acid of the present invention; and (c) a polypeptide comprising CAR activity and modeled and designed after SEQ ID NO:1.

Another embodiment of the subject invention comprises a methods for biocatalytically reducing a carboxylic acid, or a derivative thereof, to its corresponding aldehyde product(s), to provide a method of biocatalytically reducing a carboxylic acid, or a derivative thereof, to its corresponding intermediary by-product(s), as exemplified by acyl-AMP analogs, or to provide a method of biocatalytically reducing vanillic acid, or a precursor or derivative thereof, to vanillin, all using recombinant cells, extracts, CAR protein purified therefrom or derivatives and modifications of this CAR protein.

Yet another embodiment of the invention comprises a method of making a polypeptide of a recombinant gene comprising:
  a) providing a population of these host cells; and
  b) growing the population of cells under conditions whereby the polypeptide encoded by the coding sequence of the expression cassette is expressed;
  c) isolating the resulting polypeptide.

A number of expression systems using the said host cells could be used, such as but not limited to, microbial, mammalian, plant, or insect.

BRIEF DESCRIPTION OF THE DRAWINGS

FIGS. 1A-1C are alignments of the deduced amino acid sequence of $Nocardia$ CAR with a representative sample of putative homologous molecules from other organisms. Identical amino acids are highlighted in black, and similar amino acids are highlighted in gray. The Clustal W program was used to align the above sequences, and Boxshade (0.7 setting) was used to determine the degree of residue shading. The corresponding nucleotide sequence encoding $Nocardia$ CAR has been deposited in the GenBank/EMBL database. Accession numbers for the other protein sequences above are: MtfadD, $M.\ tuberculosis$ (Z77724), Mlacl, $M.\ leprae$ (NP_301424), Msmeg, $M.\ smegmatis$ (Contig 3313), MBCG, $M.\ bovis$ BCG (unnamed hypothetical protein at bases 2,885, 319-2,888,822).

FIGS. 2$a$ and $b$ are SDS-PAGE (a) and Western blot (b) analysis of $Nocardia$ CAR expression in $E.\ coli$ carrying pHAT10 based vectors. Samples taken from the lysates of $E.\ coli$ cells carrying different vectors were separated in duplicate by 10% SDS-PAGE and either stained with 0.1% Coomassie blue R-250 (A) or subjected to Western blotting using a HAT-specific antibody (B). Lane assignments for panels A and B: 1, molecular weight markers: myosin (209 kDa), beta-galactosidase (124 kDa), BSA (80 kDa), ovalbumin (49.1 kDa), carbonic anhydrase (34.8 kDa), soybean trypsin inhibitor (21.5 kDa) and lysozyme (20.6 kDa), aprotinin (7.1 kDa); 2, $E.\ coli$ cells BL21-CodonPlus®(DE3)-RP carrying PHAT-DHFR; 3, $E.\ coli$ BL21(DE3) cells carrying pHAT-305; 4, $E.\ coli$ BL21-CodonPlus®(DE3)-RP cells carrying pHAT-305 (uninduced); 5, purified HAT-CAR; 6, $E.\ coli$ CodonPlus® (DE3)-RP cells carrying pHAT10.

FIG. 3 depicts the alpha-Aminoadipate reductase motifs that were described by Casqueiro at al. and Hijarrubia et al. that are present in Car. Red letters indicate identical amino acids and blue letters indicate similar amino acids. Bold letters are matches within the motif.

FIG. 4 depicts the location of motifs within Car.

FIG. 5 depicts the location of motifs within FadD9.

FIG. 6 depicts the location of motifs in Aar: yeast AAR.

DETAILED DESCRIPTION OF THE PREFERRED EMBODIMENT

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., $The\ Microbial\ World$, (1986) 5th Ed., Prentice-Hall; O. D. Dhringra and J. B. Sinclair, $Basic\ Plant\ Pathology\ Methods$, (1985) CRC Press; Maniatis, Fritsch & Sambrook, $Molecular\ Cloning:\ A\ Laboratory\ Manual$ (1982); $DNA\ Cloning$, Vols. I and II (D. N. Glover ed. 1985); $Oligonucleotide\ Synthesis$ (M. J. Gait ed. 1984); $Nucleic\ Acid\ Hybridization$ (B. D. Hames & S. J. Higgins eds. 1984); and the series $Methods\ in\ Enzymology$ (S. Colowick and N. Kaplan, eds., Academic Press, Inc.).

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present invention, the following terms will be employed, and are intended to be defined as indicated below.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine, one exception is Micrococcus rubens, for which GTG is the methionine codon (Ishizuka, et al., *J. Gen'l Microbiol*, 139:425-432 (1993)) can be modified to yield a functionally identical molecule. Accordingly, each nucleic acid disclosed herein also includes each silent variation of the nucleic acid, which encodes a polypeptide of the present invention. It is implicit in each described polypeptide sequence and incorporated herein by reference. Examples of conservatively modified variants with silent mutations are SEQ ID NO:37 (where some gca codons have been replaced with gcg condons both of which code for Alanine) and 38 (where a tca codon has been replaced with an agt codon both of which code for serine).

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 80%, or 95%, preferably 80-95% of the native protein for it's native substrate. Conservative substitution tables providing functionally similar amino acids are well known in the art. Sequence ID no 39 is a protein sequence with a conservative substitution of A for S.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Natl. Acad Sci.* (*USA*), 82: 2306-2309 (1985)), or the ciliate Macronucleus, may be used when the nucleic acid is expressed using these organisms.

When the nucleic acid is prepared or altered synthetically, advantage can be taken of known codon preferences of the intended host where the nucleic acid is to be expressed. As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell, which contains a vector and supports the replication and/or expression of the expression vector. Host cells may be prokaryotic cells such as *E. coli*, or eukaryotic cells such as yeast, insect, plant, amphibian, or mammalian cells. Preferably, host cells are bacterial cells to provide for production of the enzyme in large quantities. A particularly preferred bacterial host cell is an *E. coli* host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids.

Unless otherwise stated, the term "CAR nucleic acid" means a nucleic acid, including all conservatively modified variants, encoding an CAR polypeptide. The term CAR, unless otherwise stated encompasses CAR and its functional, conservatively modified variants.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1-3 (1989); and *Current Protocols in Molecular Biology*, F. M. Ausubel et al., Eds., Current Protocols, a joint venture between Greene Publishing Associates, Inc. and John Wiley & Sons, Inc. (1994 Supplement).

As used herein "operably linked" includes reference to a functional linkage between a first sequence, such as a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art.

The term polynucleotide as it is employed herein embraces such chemically, enzymatically or metabolically modified forms of polynucleotides, as well as the chemical forms of DNA and RNA characteristic of viruses and cells, including inter alia, simple and complex cells. The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. An "inducible" or "regulatable" promoter is a promoter, which is under environmental control. Examples of environmental conditions that may effect transcription by inducible promoters include anaerobic conditions or the presence of light. Another type of promoter is a developmentally regulated or tissue specific promoter. Tissue preferred, cell type specific, developmentally regulated, and inducible promoters constitute the class of "non-constitutive" promoters. A "constitutive" promoter is a promoter, which is active under most environmental conditions.

The term "CAR polypeptide" refers to one or more amino acid sequences. The term is also inclusive of conservatively modified variants, fragments, homologs, alleles or precursors (e.g., preproproteins or proproteins) thereof. A "CAR protein" comprises a CAR polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267-284 (1984): $T_m$=81.5° C.+16.6 (log M)+0.41 (%GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, N.Y. (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

"Transgenic" is used herein to include any cell, cell line, or tissue, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides or polypeptides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (Best Fit) of Smith and Waterman, Adv. Appl. Math may conduct optimal alignment of sequences for comparison. 2: 482 (1981); by the homology alignment algorithm (GAP) of Needleman and Wunsch, *J. Mol. Biol.* 48: 443 (1970); by the search for similarity method (Tfasta and Fasta) of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237-244 (1988); Higgins and Sharp, *CABIOS* 5: 151-153 (1989); Corpet, et al., *Nucleic Acids Research* 16: 10881-90 (1988); Huang, et al., *Computer Applications in the*

*Biosciences* 8: 155-65 (1992), and Pearson, et al., *Methods in Molecular Biology* 24: 307-331 (1994). The preferred program to use for optimal global alignment of multiple sequences is PileUp (Feng and Doolittle, *Journal of Molecular Evolution*, 25:351-360 (1987) which is similar to the method described by Higgins and Sharp, *CABIOS*, 5:151-153 (1989) and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, N.Y. (1995).

GAP uses the algorithm of Needleman and Wunsch (J. Mol. Biol. 48: 443-453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50, or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) *Proc. Natl. Acad. Sci. USA* 89:10915).

Unless otherwise stated, sequence identity/similarity values provided herein refer to the value obtained using the BLAST 2.0 suite of programs using default parameters. Altschul et al., *Nucleic Acids Res.* 25:3389-3402 (1997).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149-163 (1993)) and XNU (Claverie and States, *Comput. Chem.*, 17:191-201 (1993)) low-complexity filters can be employed alone or in combination.

(c) As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4: 11-17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has between 50-100% sequence identity, preferably at least 50% sequence identity, preferably at least 60% sequence identity, preferably at least 87%, more preferably at least 90%, more preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 75%, preferably at least 80%, more preferably at least 90%, and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

(e) (ii) The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, *J. Mol. Biol.* 48: 443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

Carboxylic acid reductase (CAR) catalyzes the first and rate limiting step in the reduction of carboxylic acids to aldehydes, and later alcohols. According to the invention, analysis of a cloned 6.9 Kb sequence revealed that the entire open reading frame of *Nocardia* CAR and its 5' and 3' flanking regions had been cloned. ATG was identified as the translation start codon by matching the N-terminal amino acid sequence from purified *Nocardia* CAR (23) with an amino acid sequence deduced from the DNA sequence. The assignment of ATG as the start codon is supported by 5' flank region analysis: 6 bp upstream from the start codon ATG lies a conserved *Streptomyces* ribosomal binding site (GGGAGG) (27, 35). The 2.5 Kb sequence upstream of CAR showed fair homology to a putative transmembrane efflux protein (33% identity) in *S. avermitilis*, and a putative efflux protein (32% identity) in *M. tuberculosis*. The sequence downstream of *Nocardia car* showed 40%, 35%, 34% and 28% identities to putative membrane proteins in *Corynebacterium efficiens, M. tuberculosis, M. leprae*, and *S. coelicolor*, respectively. Although the CAR gene was flanked by genes encoding membrane proteins, the actual function of CAR in *Nocardia* remains unknown at this time.

BLAST analysis also showed that CAR contained two major domains and a possible phosphopantetheine attachment site. The N-terminal domain (aa 90-544) showed high homology to AMP-binding proteins. The C-terminal showed high homology to NADPH binding proteins. If a 4'-phosphopantetheine prosthetic group exists in active CAR, it likely acts as a "swinging arm" for transferring acyl-AMP intermediates to the C-terminal reductase domain. This arrangement of the CAR protein would reflect its sequential catalytic mechanism wherein the N-terminal domain catalyzes substrate activation by formation of an initial acyl-AMP intermediate, while the C-terminal portion then catalyzes the reduction of acyl-AMP by cofactor NADPH to finish a catalytic cycle. The existence of a possible 4'-phosphopantetheine prosthetic group for the catalytic process remains to be shown.

By BLAST analysis, the deduced amino acid sequence of *Nocardia* CAR showed high similarity to those of the putative enzymes in *M. tuberculosis* (fadD9, 61% identity), *M. leprae* (acyl-CoA synthetase, 57% identity), *M. smegmatis* (unnamed hypothetical protein on contig:3313, 61.8% identity), *M. bovis* strain BCG (unnamed hypothetical protein at bases 2,885,319-2,888.822, 60.3% identity), suggesting that possible functions of these proteins may relate to carboxylic acid reduction.

The present invention provides, inter alia, isolated nucleic acids of RNA, DNA, and analogs and/or chimeras thereof, comprising a CAR nucleic acid.

The present invention also includes polynucleotides optimized for expression in different organisms. For example, for expression of the polynucleotide in a maize plant, the sequence can be altered to account for specific codon preferences and to alter GC content as according to Murray et al, supra. Maize codon usage for 28 genes from maize plants is listed in Table 4 of Murray, et al., supra.

The CAR nucleic acids of the present invention comprise isolated CAR nucleic acid sequences which, are inclusive of:

(a) an isolated polynucleotide encoding a polypeptide of the present invention; (b) a polynucleotide having at least 80%, 90% or 95% identity to a polynucleotide of the present invention; (c) a polynucleotide comprising at least 25 nucleotides in length which hybridizes under high stringency conditions to a polynucleotide of the present invention; (d) a polynucleotide comprising a polynucleotide of the present invention; and (e) a polynucleotide which is complementary to the polynucleotide of (a) to (d).

The following description sets forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1999) (hereinafter "Ausubel et al." are used.

A. Preparation of CAR, Antibodies Specific for CAR and Nucleic Acid Molecules Encoding CAR 1. Proteins and Antibodies CAR may be prepared in a variety of ways, according to a variety of methods that have been developed for purifying CAR from bacteria which are detailed in the materials incorporated herein by reference. Alternatively, the availability of amino acid sequence information, such as (SEQ ID NO: 2), enables the isolation of nucleic acid molecules encoding CAR. This may be accomplished using anti-CAR antibodies to screen a cDNA expression library from a selected species, according to methods well known in the art. Alternatively, a series of degenerate oligonucleotide probes encoding parts or all of (SEQ ID NO: 1) FIG. 2 may be used to screen cDNA or genomic libraries, as described in greater detail below.

Once obtained, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md. The pCITE in vitro translation system (Novagen) also may be utilized.

According to a preferred embodiment, larger quantities of the proteins may be produced by expression in a suitable procaryotic or eucaryotic system. This is particularly beneficial for CAR as *Nocardia* sp. are difficult to propagate and maintain in culture. For example, part or all of a CAR-encoding DNA molecule may be inserted into a vector adapted for expression in a bacterial cell (such as *E. coli*) or a yeast cell (such as *Saccharomyces cerevisiae*), or a mammalian cell. Such vectors comprise the regulatory elements necessary for expression of the DNA in the host cell, positioned in such a manner as to permit expression of the DNA in the host cell. Such regulatory elements required for expression include operably linked promoter sequences, transcription initiation sequences and, optionally, enhancer sequences.

CAR produced by gene expression in a recombinant procaryotic or eukaryotic system may be purified according to methods known in the art and incorporated herein. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or with expression/secretion systems (e.g. a C-terminal tag on a secreted protein). Such methods are commonly used by skilled practitioners.

The present invention also provides antibodies capable of binding to CAR from one or more selected species. Polyclonal or monoclonal antibodies directed toward part or all of a selected CAR may be prepared according to standard methods. Monoclonal antibodies may be prepared according to general methods of Kohler and Milstein, following standard protocols. In a preferred embodiment, antibodies are prepared, which react immunospecifically with selected epitopes of CAR distinguishing it from other enzymes.

2. Nucleic Acid Molecules

Once sequence information is obtained, nucleic acid molecules encoding CAR may be prepared by two general methods: (1) they may be synthesized from appropriate nucleotide triphosphates, or (2) they may be isolated from biological sources. Both methods utilize protocols well known in the art.

The availability of nucleotide sequence information enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

Nucleic acid molecules encoding CAR also may be isolated from microorganisms of interest using methods well known in the art. Nucleic acid molecules from a selected species may be isolated by screening cDNA or genomic libraries with oligonucleotides designed to match a nucleic acid sequence specific to a CAR-encoding gene. If the gene from a species is desired, the genomic library is screened. Alternatively, if the protein coding sequence is of particular interest, the cDNA library is screened. In positions of degeneracy, where more than one nucleic acid residue could be used to encode the appropriate amino acid residue, all the appropriate nucleic acids residues may be incorporated to create a mixed oligonucleotide population, or a neutral base such as inosine may be used. The strategy of oligonucleotide design is well known in the art (see also Sambrook et al., *Molecular Cloning*, 1989, Cold Spring Harbor Press, Cold Spring Harbor N.Y.).

Alternatively, PCR (polymerase chain reaction) primers may be designed by the above method to encode a portion of CAR protein, and these primers used to amplify nucleic acids from isolated cDNA or genomic DNA. In a preferred embodiment, the oligonucleotides used to isolate CAR-encoding nucleic acids are designed to encode sequences unique to CAR, as opposed to other homologous proteins.

In accordance with the present invention, nucleic acids having the appropriate sequence homology with a CAR-encoding nucleic acid molecule may be identified by using hybridization and washing conditions of appropriate stringency. For example, hybridizations may be performed, according to the method of Sambrook et al. (1989, supra), using a hybridization solution comprising: 5×SSC, 5× Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° in 1×SSC and 1% SDS, changing the solution every 30 minutes.

Nucleic acids of the present invention may be maintained as DNA in any convenient cloning vector. In a preferred embodiment, clones are maintained in plasmid cloning/expression vector, such as pGEM-T (Promega Biotech, Madison, Wis.) or pBluescript (Stratagene, La Jolla, Calif.), either of which is propagated in a suitable *E. coli* host cell.

CAR-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting CAR-encoding genes or mRNA in test samples, e.g. by PCR amplification.

B. Uses of CAR Protein

CAR can reduce many types of carboxylic acids. Previous work by the inventors(23, 32) showed that CAR from *Nocardia* has wide ranging substrate capabilities and that the enzyme is enantioselective versus racemic carboxylic acid substrates such as ibuprofen (7). Recombinant CAR shown in the examples herein indicate that CAR effectively reduced benzoic acid, vanillic acid and ferulic acid in preparative scale reactions. However, CAR is different than coniferyl aldehyde dehydrogenase, which uses $NAD^+$ as the cofactor to catalyze the oxidation of aldehydes to acids, which does not use ATP, and which has no homology with CAR (1). ATP-dependent CAR catalyzes the energetically unfavorable reduction of acids to aldehdyes by using ATP as an energy source to drive the reaction forward. It can also catalyze the oxidation of aldehyde to acid without ATP, but the cofactor for CAR is NADP(H) instead of NAD(H). From the gene sequence, we know that CAR (3.5 kb) is much larger than aldehyde dehydrogenases (1.5 kb) (1). The enzyme also differs from fatty acid reductases in luminescent bacteria which contains three polypeptide components (31).

1. Proteins and Antibodies

Purified CAR, or fragments thereof, may be used to produce polyclonal or monoclonal antibodies which may serve as sensitive detection reagents for the presence and accumulation of the proteins in cultured cells or tissues and in intact organisms. Recombinant techniques enable expression of fusion proteins containing part or all of a selected CAR. The full length protein or fragments of the protein may be used to advantage to generate an array of monoclonal or polyclonal antibodies specific for various epitopes of the protein, thereby providing even greater sensitivity for detection of the protein. In a preferred embodiment, fragments of CAR that distinguish CAR from serum SAAs are utilized for generating epitope-specific antibodies.

Polyclonal or monoclonal antibodies immunologically specific for CAR may be used in a variety of assays designed to detect and quantitative the proteins. Such assays include, but are not limited to, (1) immunoprecipitation followed by protein quantification; (2) immunoblot analysis (e.g., dot blot, Western blot) (3) radioimmune assays, (4) nephelometry, turbidometric or immunochromatographic (lateral flow) assays, and (5) enzyme-coupled assays, including ELISA and a variety of qualitative rapid tests (e.g., dip-stick and similar tests).

Polyclonal or monoclonal antibodies that immunospecifically interact with CAR can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules.

2. Nucleic Acids

CAR-encoding nucleic acids may be used for a variety of purposes in accordance with the present invention The DNA, RNA, or fragments thereof may be used as probes to detect the presence of and/or expression of the genes. Methods in which CAR-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR) and reverse transcriptase-PCR (RT-PCR).

The exemplified CAR-encoding nucleic acids of the invention (e.g., cow, sheep, horse) may also be utilized as probes to identify related genes from other species, including s. As is well known in the art and described above, hybridization stringencies may be adjusted to allow hybridization of nucleic acid probes with complementary sequences of varying degrees of homology.

In addition to the aforementioned uses of CAR-encoding nucleic acids, they are expected to be of utility in the creation of transgenic cells, tissues and organisms.

The present invention provides novel purified and isolated nucleic acid sequences encoding CAR protein. In presently preferred forms, the DNA sequences comprise cDNA sequences encoding the novel CAR, or its conservatively modified variants, which are expressed in Nocardia cells. In a more preferred embodiment the nucleic acid sequence comprises at least about 80% identity to (SEQ ID NO:1) or 80% identity of the encoded amino acid sequence. Specifically, the sequence isolated is depicted in (SEQ ID NO:1). Alternate DNA forms such as genomic DNA, and DNA prepared by partial or total chemical synthesis from nucleotides as well as DNA with deletions or mutations, is also within the contemplated scope of the invention.

Association of DNA sequences provided by the invention with homologous or heterologous species expression control DNA sequences such as promoters, operators, regulators, and the like, allows in vivo and in vitro transcription to make mRNA which, in turn, is susceptible to translation to provide the proteins of the invention, and related poly- and oligopeptides in large quantities. In a presently preferred DNA expression system of the invention CAR encoding DNA is operatively linked to a regulatory promoter DNA sequence allowing for in vitro transcription and translation of the protein.

Incorporation of DNA sequences into prokaryotic and eucaryotic host cells by standard transformation and transfection processes, potentially involving suitable viral and circular DNA plasmid vectors, is also within the contemplation of the invention and is expected to provide useful proteins in quantities heretofore unavailable from natural sources.

Most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

Hosts and Control Sequences

Both prokaryotic and eucaryotic systems may be used to express CAR encoding sequences; prokaryotic hosts are, of course, the most convenient for cloning procedures. Prokaryotes most frequently are represented by various strains of *E. coli*; however, other microbial strains may also be used. Plasmid vectors which contain replication sites, selectable markers and control sequences derived from a species compatible with the host are used; for example, *E. coli* is typically transformed using derivatives of pBR322, a plasmid derived from an *E. coli* species by Bolivar, et al, Gene (1977) 2:95. pBR322 contains genes for ampicillin and tetracycline resistance, and thus provides multiple selectable markers which can be either retained or destroyed in constructing the desired vector. Commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al, Nature (1977) 198:1056) and the tryptophan (trp) promoter system (Goeddel, et al, Nucleic Acids Res (1980) 8:4057) and the lambda derived $P_L$ promoter and N-gene ribosome binding site (Shimatake, et al, Nature (1981) 292:128).

In addition to bacteria, eucaryotic microbes, such as yeast, may also be used as hosts. Laboratory strains of *Saccharomyces cerevisiae*, Baker's yeast, are most used although a number of other strains or species are commonly available. Vectors employing, for example, the 2µ origin of replication of Broach, J. R., Meth Enz (1983) 101:307, or other yeast compatible origins of replication (see, for example, Stinchcomb, et al, Nature (1979) 282:39, Tschumper, G., et al, Gene (1980) 10:157 and Clarke, L, et al, Meth Enx (1983) 101:300) may be used. Control sequences for yeast vectors include promoters for the synthesis of glycolytic enzymes (Hess, et al, *J Adv Enzyme Reg* (1968) 7:149; Holland, et al, *Biochemistry* (1978) 17:4900). Additional promoters known in the art include the promoter for 3-phosphoglycerate kinase (Hitzeman, et al *J Biol Chem* (1980) 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeast-derived genes.

It is also, of course, possible to express genes encoding polypeptides in eucaryotic host cell cultures derived from multicellular organisms. See, for example, Axel, et al, U.S. Pat. No. 4,399,216. These systems have the additional advantage of the ability to splice out introns and thus can be used directly to express genomic fragments. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al, *Nature* (1978) 273:113), or other viral promoters such as those derived from polyoma, Adenovirus 2, bovine papilloma virus, or avian sarcoma viruses. The controllable promoter, hMT1I (Karin, M., et al, *Nature* (1982) 299:797-802) may also be used. General aspects of mammalian cell host system transformations have been described by Axel (supra). It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes.

Transformations

Depending on the host cell used, transformation is done using standard techniques appropriate to such cells. The calcium treatment employing calcium chloride, as described by Cohen, S. N., *Proc Natl Acad Sci (USA)* 1972) 69:2110, or the rbCl2 method described in Maniatis, et al, *Molecular Cloning: A Laboratory Manual* (1982) Cold Spring Harbor Press, p. 254 and Hanahan, D., *J Mol Biol* (1983) 166:557-580 may be used for prokaryotes or other cells which contain substantial cell wall barriers. For mammalian cells without such cell walls, the calcium phosphate precipitation method of Graham and van der Eb, *Virology* (1978) 52:546, optionally as modified by Wigler, M., et al, *Cell* (1979) 16:777-785 may be used. Transformations into yeast may be carried out according to the method of Beggs, J. D. *Nature* (1978) 275:104-109 or of Hinnen, A., et al, *Proc Natl Acad Sci (USA)* (1978) 75:1929.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and relegated in the form desired.

The DNA sequences which form the vectors are available from a number of sources. Backbone vectors and control systems are generally found on available "host" vectors which are used for the bulk of the sequences in construction. Typical sequences have been set forth above. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleoside derivatives. The entire sequence for genes or cDNA's of sizable length, e.g., 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al, *Science* (1984) 223:1299; Jay, Ernest, *J Biol Chem* (1984) 259:6311.

Synthetic oligonucleotides are prepared by either the phosphotriester method as described by Edge, et al, Nature (supra) and Duckworth, et al, *Nucleic Acids Res* (1981) 9:1691 or the phosphoramidite method as described by Beaucage, S. L., and Caruthers, M. H., *Tet Letts* (1981) 22:1859 and Matteucci, M. D., and Caruthers, M. H., *J Am Chem Soc* (1981) 103:3185 and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1-2 mM ATP, 1.75y pmoles $\gamma 32P$-ATP (2.9 mCi/mmole), 0.1 mM spermidine, 0.1 mM EDTA.

Once the components of the desired vectors are thus available, they can be excised and ligated using standard restriction and ligation procedures.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 µg of plasmid or DNA sequence is cleaved by one unit of enzyme in about 20 µl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6mM MgCl2, 6 mM DTT and 0.1-1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are performed in 15-50 μl volumes under the following standard conditions and temperatures: for example, 20 mM Tris-Cl pH 7.5, 10 mM MgCl$_2$, 10 mM DTT, 33 μg/ml BSA, 10 mM-50 mM NaCl, and either 40 μM ATP, 0.01-0.02 (Weiss) units T4 DNA ligase at 0 C (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 μg/ml total DNA concentrations (5-100 nM total end concentration). Intermolecular blunt end ligations are performed at 1 μM total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent self-ligation of the vector. Digestions are conducted at pH 8 in approximately 10 mM Tris-HCl, 1 mM EDTA using about 1 unit of BAP or CIP per μg of vector at 60° for about one hour. In order to recover the nucleic acid fragments, the preparation is extracted with phenol/chloroform and ethanol precipitated. Alternatively, re-ligation can be prevented in vectors which have been double digested by additional restriction enzyme digestion and/or separation of the unwanted fragments.

For portions of vectors derived from cDNA or genomic DNA which require sequence modifications, site specific primer directed mutagenesis may be used (Zoller, M. J., and Smith, M. *Nucleic Acids Res* (1982) 10:6487-6500 and Adelman, J. P., et al, DNA (1983) 2:183-193). This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting partially or fully double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are washed after hybridization with kinased synthetic primer at a wash temperature which permits binding of an exact match, but at which the mismatches with the original strand are sufficient to prevent binding. Plaques which hybridize with the probe are then picked, cultured, and the DNA recovered.

Verification of Construction

Correct ligations for plasmid construction can be confirmed by first transforming *E. coli* strain MC1061 obtained from Dr. M. Casadaban (Casadaban, M., et al, *J Mol Biol* (1980) 138:179-207) or other suitable host with the ligation mixture. Successful transformants are selected by ampicillin, tetracycline or other antibiotic resistance by using other markers depending on the mode of plasmid construction, as is understood in the art. Plasmids from the transformants are then prepared according to the method of Clewell, D. B., et al, *Proc Natl Acad Sci (USA)* (1969) 62:1159, optionally following chloramphenicol amplification (Clewell, D. B., *J Bacteriol* (1972) 110:667). Several mini DNA preps are commonly used, e.g., Holmes, D. S., et al, *Anal Biochem Acids Res* (1979) 7:1513-1523. The isolated DNA is analyzed by restriction and/or sequenced by the dideoxy nucleotide method of Sanger, F., et al, *Proc Natl Acad Sci (USA)* (1977) 74:5463 as further described by Messing, et al, *Nucleic Acids Res* (1981) 9:309, o4 by the method of Maxam, et al, *Methods in Enzymology* (1980) 65:499.

Hosts Exemplified

Host strains used in cloning and prokaryotic expression herein are as follows:

For cloning and sequencing, and for expression of construction under control of most bacterial promoters, *E. coli* strains such as MC1061, DH1, RR1, C600hfl, K803, HB101, JA221, and JM101 can be used.

It can therefore be seen that the above invention accomplishes at least all of its stated objectives. All references cited herein are hereby expressly incorporated herein in their entirety by reference.

EXAMPLES

Materials and enzymes. Restriction enzymes, T4 DNA ligase and shrimp alkaline phosphatase were purchased from New England Biolabs (Beverly, Mass.); pGEM-T easy vector kit from Promega (Madison, Wis.); *Escherichia coli* BL21 (DE3) and BL21-CodonPlus®(DE3)-RP competent cells from Stratagene (La Jolla, Calif.); Polyclonal rabbit anti-HAT antibody, pHAT10 vector and Talon® resin from Clontech (Palo Alto, Calif.); goat anti-rabbit IgG-conjugated alkaline phosphatase and Immun-Star Chemiluminescent Substrate Kit from Bio-Rad (Hercules, Calif.); Qiaprep Spin Miniprep kit and Qiaquick kit from Qiagen Inc. (Chatsworth, Calif.). All other chemicals were from Sigma (St Louis, Mo.) unless specified.

Bacterial strains, plasmids, media and growth conditions. The bacteria and plasmids used in this study are given in Table 1. *Nocardia* sp. NRRL 5646 (9), maintained in the University of Iowa College of Pharmacy culture collection on slants of Sabouraud-Dextrose agar or sporulation agar (ATCC no. 5 medium), was grown in Luria-Bertani (LB) medium containing 0.05% Tween 80 (vol/vol, liquid medium only). With *E. coli* (JM109, BL21 (DE3), or BL21-CodonPlus®(DE3)-RP) as the recombinant host for pHAT based vectors, cells were grown at 37° C. on solid or in liquid LB medium. Ampicillin (100 μg/ml) was incorporated into LB medium to select for recombinants. In addition, isopropyl-β-D-thiogalactopyranoside (IPTG, 1 mM) and/or 5-bromo-4-chloro-3-indolyl-β-D-galactopyranoside (X-Gal, 80 μg/ml) were included for recombinant selection and identification.

Molecular biology techniques. All DNA manipulations used for this study were performed by standard protocols (33). *Nocardia* sp. NRRL 5646 chromosomal DNA (gDNA) was purified as described by Pelicic et al. (29) with modifications. Briefly, ampicillin (0.2 mg/ml) and glycine (1.5%, vol/vol) were added into 100 ml stationary phase cultures, two hrs before harvest by centrifugation at 4,000×g for 15 min and 4° C. Cells (1.5 g, wet weight) were resuspended in 5 ml of lysis solution 1 (25% sucrose in 50 mM Tris-HCl, pH 8.0 containing 50 mM EDTA and 12 mg/ml lysozyme), and incubated at 37° C. with shaking at 50 rpm for 1.5 hrs. Lysis solution II (3 ml of 100 mM Tris-HCl, pH 8.0 containing 1% SDS and 700 □g/ml proteinase K) was then added, and the sample was incubated at 55° C. for 4 hrs. Then 45 □l Rnase (500 □g/ml) was added into the lysate, and incubated with shaking at 50 rpm and 37° C. for 1 h. The lysate was then extracted with phenol-chloroform-isoamyl alcohol (25:24:1, vol/vol/vol, Invitrogen Life Technologies), and gDNA was concentrated by ethanol precipitation, yielding a total of 90 μg gDNA. Recombinant plasmids from *E. coli* were purified by using a Qiaprep spin miniprep kit, and Qiaquick kits were used for PCR cleanup and gel extractions with vector constructs as instructed by the manufacturer. All PCR cloning amplification was done with either Platinum Taq DNA polymerase or Platinum Pfx DNA polymerase (Invitrogen).

Restriction enzymes and DNA-modification enzymes were used according to the manufacturer's protocols. Sequencing was conducted using an Applied Biosystem 373A DNA sequencer.

PCR and cloning of PCR product. In order to obtain a portion of *Nocardia car*, oligonucleotides were constructed corresponding to N-terminal and internal amino acid sequences, which were determined with purified CAR (23). Forward primers (Noc-1 and Noc-2) were based on the N-terminal amino acid sequence AVDSPDERLQRRIAQL (SEQ ID NO:6), and reverse primers (Noc-3 and Noc-4) were based on the complementary strand sequence encoding the internal amino acid sequence KLSQGEFVTVAHLEAV (SEQ ID NO:7) (Table 2). Degeneracy of all four primers was minimized by taking advantage of the reported *Nocardia* codon preferences (10). A typical 50 μl reaction in 1×PCR buffer contained 500 ng *Nocardia* DNA, 5 mM $Mg^{++}$, 500 μM of each dNTP, 0.5 μM of each primer, 1% DMSO (vol/vol) and 3.5 units of Taq DNA polymerase. The reaction mixtures were subjected to the following cycles: one cycle at 94° C. for 4 min, thirty cycles at 94° C. for 45 s, 56° C. for 45 s, and 72° C. for 2 min, and finally one cycle at 72° C. for 10 min. PCR products were separated on 1% agarose gel. The desired band was excised and extracted with a Qiagen gel extraction kit. The resulting PCR product was ligated into pGEM-T by T4 ligase. The ligation mixture was mixed with *E. coli* JM109 cells and chilled on ice for 30 min. Cells were transformed by heat shock, then placed immediately on ice. Transformed *E. coli* JM 109 cells were mixed with 800 μl SOC medium and incubated at 37° C. for 1.5 hrs on a rotary shaker at 170 rpm. Plasmid transformants were spreadplated onto LB/X-Gal agar supplemented with 100 μg/ml ampicillin. Ampicillin resistant colonies were picked and used to inoculate 5 ml LB broth supplemented with 100 μg/ml ampicillin and incubated overnight at 37° C. on a rotary shaker operating at 170 rpm. Cultures were harvested by centrifugation and subjected to a plasmid miniprep procedure (Qiagen). The resulting recombinant plasmid was sequenced in both directions with sequencing primers (Table 2).

Inverse PCR. Inverse PCR was used to obtain the entire *Nocardia asteriodes car* gene sequence. To prepare the template for Inverse PCR analysis, 1 μg of *Nocardia asteriodes* gDNA was completely digested with 20 U SalI or Acc65I at 37° C. Digested gDNA was diluted five fold and then circularized with T4 DNA ligase. PCR primers CA-5 (Forward) and CA-7 (Reverse) were designed based on part of the *Nocardia asteriodes car* sequence obtained above. Inverse PCR was performed using Taq DNA polymerase for a total of 30 cycles with the following cycling pattern: melting at 94° C. for 45 s, annealing at 57° C. for 45 s, and polymerization at 72° C. for 2 min. The amplified PCR product was cloned in pGEM-T, and transformed into *E. coli* JM109 cells by heat shock treatment as described above. Plasmid preparations from independent clones were sequenced in both directions. The resulting sequence combined with the above part of *Nocardia asteriodes car* gave a 4.6 Kb sequence which contained the entire *Nocardia asteriodes car* gene (with Acc65I digested and then religated gDNA as the template). A sequence of 2.5 Kb upstream car was obtained with SalI digested and religated gDNA as the template for PCR.

Construction of expression vectors. To express recombinant *Nocardia asteriodes car* in *E. coli*, a DNA fragment containing *Nocardia asteriodes car* was generated by PCR using the primers car-F and car-R with *Nocardia asteriodes* gDNA as the template. For cloning purposes, those two primers incorporated a BamHI site at the 5' end and an KpnI site at the 3' end of the *Nocardia* gene insert. PCR was performed using Platinum Pfx DNA polymerase for a total of 30 cycles with the following cycling pattern: melting at 94° C. for 18 s, annealing at 59° C. for 30 s, and polymerization at 72° C. for 4 min. PCR products were sequentially digested with BamHI and KpnI was separated on a 1% agarose gel and purified using a Qiagen gel extraction kit, and then subcloned into the corresponding sites of pHAT10 to result in pHAT-305. One round of sequencing confirmed that *Nocardia car* had been correctly cloned into the pHAT vector by using sequence primers.

Expression of *Nocardia car* in *E. coli*. A 100 ml culture of *E. coli* cells (BL21(DE3) or BL21-CodonPlus®(DE3)-RP) harboring pHAT-305 were grown overnight in LB medium containing 100 μg/ml ampicillin at 37° C. Overnight broth cultures were diluted 20 fold in fresh LB medium containing 100 μg/mL ampicillin, and then incubated at 170 rpm in a rotary shaker at 37° C. to an optical density at 600 nm of 0.6, followed by addition of 1 mM IPTG and further incubation for 4.5 h. The cells were harvested by centrifugation (10 min, 5,000×g), and then stored at −65° C. before use.

Enzyme assay. The standard reaction mixture contained 1 mM ATP, 0.15 mM NADPH, 5 mM sodium benzoate, 10 mM $MgCl_2$ and enzyme in 0.05 M Tris buffer (pH 7.5) containing 1 mM EDTA, 1 mM DTT and 10% glycerol (vol/vol), in a final volume of 1.4 ml. The reference cuvette contained all components except benzoate. Reactions were initiated by adding enzyme, and were monitored by recording the absorption decrease at 340 nm at 25° C. with a Shimadzu UV-2010PC scanning spectrophotometer. One unit of the enzyme was defined as the amount of enzyme that catalyzed the reduction of 1 μmol of benzoate to benzaldehyde.$min^{-1}$ under standard assay condition. Protein concentrations were measured by the Bradford protein microassay (4) with bovine serum albumin as the standard.

Purification of overexpressed HAT-CAR fusion protein. *E. coli* BL21-CodonPlus®(DE3)-RP cells (4.3 g wet weight) transformed with pHAT-305 were suspended in 26 ml of 0.05 M $K_2HPO_4$ (pH 7.5) buffer containing 0.3 M NaCl, 10% (vol/vol) glycerol, 0.2 mM PMSF and 3 mM P-mercaptoethanol. The cells were disrupted by passing through a French Press cell at 12,000 psi twice. The cell debris was removed by centrifugation for 60 min at 25,000×g and 4° C. The resulting supernatant (27 ml) was referred to as cell-free extract (CFE) and used for HAT-CAR purification. 24 ml of CFE was loaded on a 6 ml bed volume column of Talon resin (A cobalt complexed resin made by Clontech that specifically binds the HAT tag.) equilibrated with 0.05 M $K_2HPO_4$ buffer pH 7.5 containing 0.3 M NaCl, 10% (vol/vol) glycerol, at a flow rate of 0.4 ml/min. After the column was washed with 35 ml 0.05 M $K_2HPO_4$ buffer pH 7.5 containing 0.3 M NaCl, 10% (vol/vol) glycerol, the HAT-CAR was eluted sequentially by 16 ml of 5 mM, 7.5 mM, 10 mM, and 20 mM of Imidazole in 0.05 M $K_2HPO_4$ buffer pH 7.5 containing 0.3 M NaCl, 10% (vol/vol) glycerol. Active fractions were pooled and then concentrated by ultrafiltration in an Amicon concentrator (PM-10 membrane) and then diluted with 100 ml of 50 mM Tris buffer (pH 7.5) containing 1 mM EDTA, 1 mM DTT, and 10% glycerol. The resulting enzyme preparation was loaded on a DEAE Sepharose column (1.5 by 20 cm with a bed volume of 24 ml) equilibrated with 50 mM Tris buffer (pH 7.5) containing 1 mM EDTA, 1 mM DTT, and 10% glycerol. The column was washed with 30 ml of starting buffer and eluted with a 0 to 0.5 M NaCl linear gradient (total 100 ml). The active fractions (29 to 34) were combined for subsequent analysis (Table 3).

SDS-PAGE and Western blot analysis. Proteins were separated by SDS-PAGE as described by Laemmli (22). For Western blot analysis, protein samples were subjected to SDS-PAGE and then transferred to a polyvinylidene difluoride (PVDF) membrane. To identify proteins containing the HAT tag, the PVDF membrane was first incubated with 2% fat-free milk in TBS, then with a polyclonal anti-HAT antibody (diluted 1:20,000) that recognizes epitopes throughout the HAT tag, and finally with a polyclonal goat anti-rabbit IgG conjugated to alkaline phosphatase (diluted 1:20,000), which was used with the Bio-Rad Immuno-Star Chemoluminescent Substrate. Proteins containing the HAT tag were identified with Kodak BioMax MR photographic film after 2 min exposures. *E. coli* JM109 carrying an expression vector coding for HAT-tagged dihydrofolate reductase (DHFR, Clontech) was used as a positive control for each Western blot analysis, and *E. coli* BL21-CodonPlus® (DE3)-RP carrying the pHAT10 vector was used as a negative control.

In vitro and in vivo transformations of benzoate, vanillic acid, and ferulic acid. In vitro enzyme reactions were carried out in a reaction mixture of 50 ml of 50 mM Tris-HCl buffer (pH 7.5) containing 0.1 mmol of substrate, 12.5 mg of NADPH, 55 mg ATP, 101 mg MgCl$_2$, 33.6 mg glucose-6-phosphate, and 3 U of glucose-6-phosphate dehydrogenase, and 1 mg purified HAT-CAR (0.1 U). Reaction mixtures were incubated at 30° C. with gentle shaking at 50 rpm for 24 h.

In vivo whole cell reactions were typically conducted with 100 ml cultures of *E. coli* BL21-CodonPlus®(DE3)-RP carrying pHAT-305. Cultures were induced by 1 mM IPTG for 4 hrs before receiving 1 mg/ml of benzoic acid, vanillic acid, or ferulic acid.

Samples of approximately 2 mL were removed at various time intervals, sample pH was adjusted to pH 2.0 with 6N HCl, and samples were extracted with 1 ml ethyl acetate, and centrifuged for 2 min at 1,000×g. Organic phases were removed and used to spot silica gel GF$_{254}$ TLC plates for analysis, and comparison with authentic standards of benzaldehyde, vanillin and coniferaldehyde. For metabolite isolation, reactions were stopped by adjustment of mixtures to pH 2.0 with 6N HCl, and extracted three times with half-volumes of ethyl acetate. After removal of solvent by rotary evaporation, reduction products were purified by preparative TLC for analysis and comparison with authentic standards.

Four degenerate primers (two forward, CA-1 and CA-2; and two reverse, CA-3 and CA-4) incorporating *Nocardia* codon preferences (10) were initially designed to identify part of *Nocardia car*, based on the known N-terminal amino acid sequence and internal amino acid sequences (Li and Rosazza, 1997). PCR products were cloned into a pGEM-T vector and sequenced to give a 1.6 Kb sequence.

Gene sequence specific primers (CA-5 and CA-6) based on this identified fragment were synthesized for inverse PCR to clone the entire *Nocardia car* gene. The sequence derived from two inverse PCR experiments and the above-obtained sequence gave a total of 6.9 Kb of data, which included the entire *Nocardia car* gene and its flanking regions. The DNA sequence and the deduced amino acid sequence of *Nocardia car* will be deposited in the GenBank upon filing of a patent. *Nocardia car* consisted of 3525 bp, corresponding to 1174 amino acid residues with a calculated molecular mass of 128.3 kDa and an isoelectric point (pI) of 4.74. The N-terminal amino acid sequence of purified *Nocardia* CAR exactly matched the deduced amino acid sequence of the N-terminus, with Ala as the first amino acid. Met, encoded by the start codon ATG in *Nocardia car*, is apparently removed by post-translational modification in the mature form of the protein produced in wild type *Nocardia* cells.

Comparative sequence analysis. When the *Nocardia car* sequence was compared by BLAST analysis with DNA sequences in the NCBI database, the BestFit analysis of two nucleotide sequences showed that the *Nocardia* CAR was 60% and 57% identical to the putative polyketide synthetase fadD9 of *M. tuberculosis* and putative acyl-CoA synthetase of *M. leprae* respectively. Putative proteins in *M. smegmatis* and *M. bovis* strain BCG were 61.8% and 60.3% identical to *Nocardia* CAR. The Clustal W program (35) was used to align CAR with these closely-related putative proteins from different species (FIG. 1).

Heterologous expression of *Nocardia car*. For expression of *Nocardia* CAR, the *Nocardia car* gene was successfully cloned in frame into pHAT10 to form the expression vector pHAT-305. Constructed vectors were found by complete sequencing to have a car that was 100% identical to the original *Nocardia car* sequence, proving that no errors were introduced by Pfx DNA polymerase cloning. Lysate from *E. coli* BL21(DE3) cells carrying pHAT-305 had moderate carboxylic acid reductase activity (0.003 U/mg of protein) versus that of *Nocardia* wild type cells (0.03 U/mg of protein) (23). However, the expression of pHAT-305 was much improved when it was transformed into *E. coli* CodonPlus® (DE3)-RP cells, where a crude extract specific activity of 0.009 U/mg of protein was observed. When these cultures were examined by SDS-PAGE, the Coomassie blue-stained band with an apparent molecular size of 132.4 kDa were confirmed to be the HAT-CAR by activity assay and Western blot analysis (FIG. 2). Also, the DHFR-positive control (lysate of *E. coli* carrying the DHFR gene cloned into the same pHAT 10 vector) and negative control (lysate of *E. coli* BL21-CodonPlus®(DE3)-RP cells carrying the pHAT10 vector) showed the absence of a 132.4 kDa band by SDS-PAGE and Western blot analyses.

The HAT-CAR protein from *E. coli* was purified to homogeneity on SDS-PAGE by Talon® resin affinity chromatography and DEAE sepharose column with a overall recovery of 85%. Western blot analysis showed that there were some HAT-tag positive smear bands with lower molecular weight than that of HAT-CAR. The purified HAT-CAR showed a specific CAR activity of 0.11 µmol.min$^{-1}$.mg.$^{-1}$ protein, which was less than that of CAR purified from *Nocardia* cells (5.89 U/mg of protein) (23). Kinetic constants were determined by fitting experimental data with Cleland's kinetics program (9). Km values for benzoate, ATP and NADPH were determined to be 852±82 mM, 69±6.6 µM, and 57±3.6 µM, respectively. These are similar to the Km values of the natural protein. Vmax was determined to be 0.135±0.004 µmol. min$^{-1}$.mg$^{-1}$ protein, which is lower than that of the natural protein at 0.902±0.04 µmol.min$^{-1}$.mg$^{-1}$ protein (23).

In vitro transformations showed that pure HAT-CAR could reduce various carboxylic acids to their corresponding aldehydes in reactions that were not optimized. Benzoic acid was converted to benzaldehyde (96% yield), vanillic acid to vanillin (49% yield), and ferulic acid to coniferyl aldehyde (22% yield). In vivo studies on the transformation of the same substrates showed that benzoate was quickly converted to benzyl alcohol, while vanillin and coniferyl aldehyde converted to their corresponding alcohols.

Recombinant CAR bound weakly to Talon® affinity matrix, being eluted from columns by 10 mM imidazole, rather than the 100 mM imidazole usually required for HAT-tagged proteins elution. HAT-CAR can be easily purified to near homogeneity (SDS-PAGE) with Talon® matrix chromatography. Minor impurities in enzyme preparations after the affinity step were not completely removed by DEAE sepharose column chromatography. Although trace impurities were not detected by SDS-PAGE, they were detected by Western blot analysis (FIG. 2). These trace impurities were HAT-tag containing proteins that are likely hydrolyzed fragments of HAT-CAR cleaved by metal proteases. Metal protease inhibitors were not used to prevent protease cleavage during cell disruption because they would be incompatible with Talon® matrix chromatography.

CAR was only moderately expressed in *E. coli* BL21 (DE3) cells carrying pHAT-305. It was thought that low expression was mainly due to the codon bias that can cause early termination and misincorporation of amino acids since the G+C content of the sequence is 66%. In searching for new hosts to overcome the codon bias, the expression of pHAT-305 was much improved when it was carried out in *E. coli* CodonPlus®(DE3)-RP cells. The protein bands were clearly seen on the SDS-PAGE (FIG. 2) with the CFE enzyme preparation. Although CAR of the correct molecular mass accumulates in cells, the specific activity of the crude extract was only improved about 3 fold. The specific activity of CAR in *E. coli* BL21 (DE3) may be higher than in *E. coli* CodonPlus® (DE3)-RP cells. We have shown that approximately 50 mg pure HAT-CAR can be obtained from a 1 liter culture of *E. coli* CodonPlus®(DE3)-RP cells.

Comparing relative protein expression and differing specific activities of CAR in these two different hosts, we speculate that two forms of the enzyme may exist in *E. coli* cells: one active, while the other is an inactive variant. It is possible that the conversion of an inactive form of the enzyme (pre-CAR) to the catalytically active form of the enzyme (CAR) may occur by posttranslational modification. One such modification that has precedence in the type of reaction catalyzed by CAR would be phosphopantetheinylation (12). In this type of model, inactive pre-CAR would be converted to active CAR by attachment of phosphopantetheine prosthetic group possibly attached to Ser688 to function as a Swinging arm. In the active enzyme, CAR, the SH of the phosphopantetheine prosthetic group would react with acyl-AMP to form an acyl-S-pantotheine-CAR intermediate. The C-terminal reductase domain finishes the catalytic cycle by delivering hydride from NADPH to the acyl-S-pantotheine-CAR intermediate freeing an aldehyde product. α-Aminoadipate reductase is well studied, and motifs responsible for adenylation of α-aminoadipate, reduction, NADPH binding and attachment of a phosphopantetheinyl group used in the reaction have been identified (5, 18). While traditional blast analysis does not reveal the expected common motifs in the N-terminal portion of car, they do appear in the C-terminal portion. A P-pantotheine attachment site, domain J, is clearly present in CAR (LGGxSxxA) (SEQ ID NO:8), as are the reduction domain (GYxxSKW) (SEQ ID NO:9) and the NADP binding domain (GxxGxLG) (SEQ ID NO:10). These motifs are fully conserved in the *Mycobactrium* CAR homologs (FIG. 1). Whether benzoate induction (23) increases the expression of CAR, or catalyzes the conversion of inactive form enzyme to active form by a posttranslational modification remains to be established.

Biotransformation reactions using IPTG-induced whole growing cells of *E. coli* CodonPlus®(DE3)-RP cells carrying pHAT-305 were simple to conduct, and they smoothly converted carboxylic acids to aldehydes—and subsequently to alcohols. With whole cells, expensive cofactors are not needed (25), and the relatively slow reduction of aldehyde products formed by CAR to alcohols by an endogenous *E. coli* alcohol dehydrogenase similar to that in *Nocardia* (25) may be obviated by judicious biochemical engineering approaches with the recombinant organism.

The unique car sequence car for the carboxylic acid reductase enzyme, CAR, may be used to produce recombinant cultures such as *E. coli* for direct use in whole cell biocatalytic conversions of an enormous number of synthetic or natural carboxylic acids (23, 32) including aromatic, aliphatic, alicyclic and others. Alternatively, this gene sequence, or homologs of this gene sequence may be incorporated into the genomes of multiply recombinant strains through pathway engineering to be used as a part of a biosynthetic or biodegradative pathway leading to useful compounds.

TABLE 1

Strains and plasmids used in this study

| Strains or plasmids | Relevant properties | Reference or source |
|---|---|---|
| *Nocardia* sp. NRRL 5646 | Wild type | 8 |
| *E. coli* JM 109 | RecA⁻, recombinant vector host strain | Promega |
| *E. coli* BL21 (DE3) | Inducible T7 RNA polymerase, Amp$^r$ | Stratagene |
| *E. coli* BL21-CodonPlus ® (DE3)-RP | having argU and proL tRNA genes | Stratagene |
| pGEM-T easy | T/A PCR cloning vector, Amp$^r$ | Promega |
| pHAT10 | Cloning vector for addition of HAT-tag to the N-terminus, Amp$^r$ | Clontech |
| pHAT-305 | pHAT-10 with car insert | This study |
| pHAT-DHFR | Positive control expression vector with dihydrofolate reductase gene tagged with HAT at the N-terminus | Clontech |

TABLE 2

Oligonucleotides used in this study

| Oligonucleotides | Sequence (from 5' to 3')[a] | Source |
|---|---|---|
| Cloning primers | | |
| CA-1 | GTSGATTCACCSGATGAG | herein (SEQ ID NO:11) |
| CA-2 | CCSGATGARCGSCTACAG | herein (SEQ ID NO:12) |
| CA-3 | TGSGCSACSGTSACGAAC | herein (SEQ ID NO:13) |
| CA-4 | SACGAAYTCSCCCTGSGAC | herein (SEQ ID NO:14) |
| CA-5 | GGTCGGGATCAATCTCAACTACATG | herein (SEQ ID NO:15) |
| CA-6 | CTTCAGCTGCTCTGACGGATATCAG | herein (SEQ ID NO:16) |
| CA-7 | CCTGCTCATCTTCTGCAAACAACTG | herein (SEQ ID NO:17) |
| carF | CGC<u>GGATCC</u>GCAGTGGATTCACCGGATGAGC | herein (SEQ ID NO:18) |
| carR | CGG<u>GGTACC</u>CCTGATATCCGTCAGAGCAGCTG | herein (SEQ ID NO:19) |

TABLE 2-continued

Oligonucleotides used in this study

| Oligonucleotides | Sequence (from 5' to 3')[a] | Source |
|---|---|---|
| Sequencing primers | | |
| T7 | TAATACGACTCACTATAGGG | Sigma-Genosys (SEQ ID NO:20) |
| SP6 | CATACGATTTAGGTGACACTATAG | Sigma-Genosys (SEQ ID NO:21) |
| M13 reverse | CAGGAAACAGCTATGACC | Sigma-Genosys (SEQ ID NO:22) |
| Scar-1 | CTCGACCTGGCCGATATCCAC | herein (SEQ ID NO:23) |
| Scar-2 | GAGGACGGCTTCTACAAGAC | herein (SEQ ID NO:24) |
| Scar-3 | GACGCGCACTTCACCGACCTG | herein (SEQ ID NO:25) |
| Scar-4 | GTCGACCTGATCGTCCATCC | herein (SEQ ID NO:26) |
| Sacr-5 | ACCTACGACGTGCTCAATC | herein (SEQ ID NO:27) |
| Scar-6 | CGTACGACGATGGCATCTC | herein (SEQ ID NO:28) |
| Scar-7 | GTGGATATCGGCCAGGTCGAG | herein (SEQ ID NO:29) |
| He-32 | GGTGGCAGGATGGAATCGG | herein (SEQ ID NO:30) |
| He-33 | CGTCGATTCGCGATTCCCTG | herein (SEQ ID NO:31) |

[a]Restriction cleavage sites are underlined; R=A or G , Y=C or T, S=G or C.

TABLE 3

Purification of recombinant HAT-CAR from Nocardia.

| Step | Total protein (mg) | Total activity (U)[1] | Specific activity (U/mg) | Yield (%) | Purification |
|---|---|---|---|---|---|
| Crude extract | 600 | 5.21 | 0.009 | 100 | 1 |
| Talon Matrix | 69.1 | 4.57 | 0.066 | 87.7 | 7.62 |
| DEAE Sepharose | 49 | 4.43 | 0.09 | 85 | 10 |

[1]One unit of the enzyme is defined as the amount of the enzyme that catalyzed the reduction of 1 μmol of benzoate to benzaldehyde per min at 25° C.

Homology

In conducting BLAST analysis the database proteins most similar to CAR are proteins of unknown function in mycobacteria. The most similar known enzymes are Alpha aminoadipate reducatase and peptide synthetases, but it is unlikely that Car is either of these. Nonetheless, it is likely that the mechanism of benzoate reduction is similar to alpha-aminoadipate reduction. Piperideine-6-carboxylate dehydrogenase has no sequence similarity to CAR, and its mechanism is unlikely to be related to that of Car.

CAR shows very unique catalytic properties. It is very tolerant, taking carboxylic acids with different structures, as long as they are hydrophobic. In addition, when CAR was tested with alpha amino acids, none of them were reduced. If the alpha amino group is protected with a hydrophobic group, such as Boc, all were reduced with good efficiencies. Therefore, CAR is most likely different from alpha-amino adipate reductase despite the similar motifs.

CAR is most homologous to a set of proteins of similar large size, thus far found only among the mycobacteria. The best hit is with the *Mycobacterium tuberculosis* protein identified as a 'putative substrate-CoA ligase' (in Mtb CDC1551) or 'putative acyl CoA ligase' (FadD9; Rv2590, in Mtb H37Rv). These proteins give a score of 1336, E value of 0, and are 60% identical and 75% positive. The next best hit is with a 'putative acyl-CoA synthetase' from *Mycobacterium leprae*. Another strong hit is also obtained with the *Mycobacterium smegmatis* database.

A conserved domain search shows that the protein consists of two main domains, plus a small third domain. The N-terminal portion has homology with a variety of acyl-CoA synthetases and AMP-binding proteins, polyketide synthase, and peptide synthetase modules. Between the N-terminal and C-terminal regions is a short section similar to phosphopantetheine attachment sites (aa 650-725). The C-terminal portion has homology with a variety of dehydrogenases and NAD(P)-dependent enzymes. The 740 N-terminal amino acids and the 482 C-terminal amino acids were blasted giving a bit of overlap. Tables 1 and 2 describe most of the best blast hits. Most protein homologues listed do not have known functions. It appears that the N-terminal and C-terminal Blast hits of CAR with *Streptomyces* are not with the same proteins, but this is not yet clear, since the *S. coelicolor* database is not yet fully annotated. The closest hits to known proteins are with alpha-aminoadipate reductase and a non-ribosomal peptide synthetase (for both N-terminal and C-terminal portions). These hits with known proteins are not very strong. alpha-Aminoadipate semialdehyde is in chemical equilibrium with 1-piperideine-6-carboxylate. It is of interest that there is some similarity in structure between the 1-piperideine-6-carboxylate and benzoic acid. This might suggest some evolutionary relationship between the benzoate reductase and the aminoadipate enzyme. However, given the low level of identity, it is unlikely that the benzoate reductase is actually an alpha-aminoadipate semialdehyde dehydrogenase. Furthermore, the *Mycobacterium* homologues would not be Aar because these organisms make lysine via the diaminopimelic acid path rather than the aminoadipate path.

Bacterial means for converting piperideine-6-carboxylate (α-aminoadipate semialdehyde) into a-aminoadipate exists in *Nocardia, Streptomyces, Flavobacterium* and *Pseudomonas*, by use of 1-piperideine-6-carboxylate dehydrogenase. The gene for this enzyme has been identified in *Flavobacterium* and *Streptomyces clavuligerus*, and it has good homology with AldB (Rv3293 in *M. tuberculosis*). However, it has no homology with Car, despite the similarity of the piperideine-6-carboxylate dehydrogenase with the Car reaction. This makes sense, since this reaction does not involve ATP and NAD is used instead of NADP. Alpha-Aminoadipate reductase has been well studied. Motifs responsible for adenylation of alpha-aminoadipate, reduction, NADP(H) binding, and attachment of the P-pantetheinyl group used in the reaction have been identified. Given the similar overall sizes of Aar proteins and Car, and at least weak blast hits with both the N-terminal and C-terminal portions of the Car sequence, it might be reasonable to postulate a great similarity in mechanism between the two enzymes. However, traditional blast analysis does not reveal the expected common motifs in the N-terminal portion of car, although they appear in the C-terminal portion. Nonetheless, when the motifs are searched for "visually", many of them are found, as shown in FIG. 3. FIG. 4, FIG. 5, and FIG. 6 show the locations of these motifs within Car, the *M. tuberculosis* homologue FadD9, and a yeast Aar. "Adenylation domain" motifs C, D, F, H and I are found in Car, although A, B, E, and G are not. The P-pantetheine attachment site, domain J, is clearly present, as are the reduction (R) domain and the NADP-binding domain.

TABLE 1

Comparison of amino acid sequence of N-terminal 740 aa of Car to database sequences using Blast analysis

| Organism | Sequence ID | Sequence function | Blast score | E value | % ID | % Positive |
| --- | --- | --- | --- | --- | --- | --- |
| *M. tuberculosis* | FadD9 | Putative acyl-CoA synthetase | 764 | 0 | 57 | 72 |
| *M. bovis* BCG | 2.885331 | Not annotated | "2074" | $2.4 \times 10^{-213}$ | 57 | 72 |
| *M. leprae* | ML0484 | Putative acyl-CoA ligase | 769 | 0 | 54 | 70 |
| *M. smegmatis* | 3.09264 | Not annotated | "3528" | 0 | 61 | 75 |
| *S. coelicolor* | SC02561 | Putative fatty acid-CoA ligase | 251 | $3.5 \times 10^{-29}$ | 29 | 50 |
| *S. coelicolor* | SC04383 | Putative 4-coumarate:CoA ligase | 221 | $6.8 \times 10^{-18}$ | 28 | 42 |
| *Drosophila* | CG3961-PA | Hypothetical protein | 211 | $4 \times 10^{-53}$ | 31 | 49 |
| *Mus* | AAH31544 | Similar to fatty acid Co-A ligase | 202 | $2 \times 10^{-50}$ | 27 | 46 |
| *T. fusca* | Scaf 1 | Not annotated | 121 | $3 \times 10^{-28}$ | 25 | 41 |
| *Stigmatella aurantica* | MxaA | Non-ribosomal peptide synthetase (in myxalamid biosynthesis) | 39 | $7 \times 10^{-5}$ | 26 | 41 |
| *Schizosaccharomyces pombe* | P40976 | □-Aminoadipate reductase | 25 | 0.14 | 23 | 43 |
| *Candida albicans* | AAC02241 | □-Aminoadipate reductase | 25 | 0.18 | 22 | 40 |

Bold letters indicate genes known to make a particular enzyme.

TABLE 2

Comparison of amino acid sequence of C-terminal 482 aa of Car to database sequences using Blast analysis

| Organism | Sequence ID | Sequence function | Blast score | E value | % ID | % Positive |
| --- | --- | --- | --- | --- | --- | --- |
| *M. tuberculosis* | FadD9 | Putative acyl-CoA synthetase | 583 | $10^{-165}$ | 61 | 74 |
| *M. bovis* BCG | 2.887365 | Not annotated | "1531" | $3 \times 10^{-155}$ | 60 | 74 |
| *M. leprae* | ML0484 | Putative acyl-CoA ligase | 555 | $1 \times 10^{-157}$ | 58 | 74 |
| *M. smegmatis* | 3.11301 | Not annotated | "1597" | $4.8 \times 10^{-164}$ | 62 | 77 |
| *S. coelicolor* | SCO6273 | Putative polyketide synthase | 323 | $1.6 \times 10^{-27}$ | 35 | 51 |
| *S. coelicolor* | SCO1273 | Putative reductase | 248 | $4.7 \times 10^{-28}$ | 39 | 52 |
| *Stigmatella aurantica* | MxaA | Non-ribosomal peptide synthetase (in myxalamid biosynthesis) | 148 | $2 \times 10^{-34}$ | 33 | 46 |
| *Schizosaccharomyces pombe* | P40976 | □-Aminoadipate reductase | 116 | $9 \times 10^{-25}$ | 27 | 46 |
| *Pichia farinosa* | CAB97252 | □-Aminoadipate reductase | 108 | $2 \times 10^{-22}$ | 25 | 42 |
| *T. fusca* | | No Hits | | | | |

Bold letters indicate genes known to make a particular enzyme.

What is claimed is:

1. An isolated carboxylic acid reductase polypeptide having carboxylic acid reductase activity, said polypeptide selected from the group consisting of:
   (a) an isolated polypeptide having at least 95% sequence identity to SEQ ID NO:2; and
   (b) an isolated polypeptide encoded by the nucleic acid of SEQ ID NO:1.

2. The isolated carboxylic acid reductase polypeptide of claim 1 wherein said polypeptide comprises the amino acid sequence of SEQ ID NO: 2.

3. A method of reducing a carboxylic acid substrate to an aldehyde product comprising:
   a) obtaining the carboxylic acid reductase of claim 1; and
   b) exposing said carboxylic acid substrate to said recombinant carboxylic reductase, thereby reducing said acid substrate to an aldehyde product, wherein said substrate is a vanillic acid, benzoic acid or ferulic acid.

* * * * *